United States Patent
Dicks et al.

(10) Patent No.: US 9,760,363 B2
(45) Date of Patent: Sep. 12, 2017

(54) SYSTEMS FOR REMOTE PROVISIONING OF ELECTRONIC DEVICES

(71) Applicant: Medapps, Inc., Scottsdale, AZ (US)

(72) Inventors: Kent E. Dicks, Scottsdale, AZ (US); Thomas Crosley, Gilbert, AZ (US); Chuck Waterbury, Phoenix, AZ (US)

(*) Notice: Subject to any disclaimer, the term of this patent is extended or adjusted under 35 U.S.C. 154(b) by 0 days.

(21) Appl. No.: 14/629,451

(22) Filed: Feb. 23, 2015

(65) Prior Publication Data
US 2015/0169314 A1 Jun. 18, 2015

Related U.S. Application Data

(63) Continuation of application No. 12/940,944, filed on Nov. 5, 2010, now Pat. No. 8,966,235.

(51) Int. Cl.
| | |
|---|---|
| G06F 9/00 | (2006.01) |
| G06F 15/177 | (2006.01) |
| G06F 9/445 | (2006.01) |
| G06F 9/44 | (2006.01) |
| G06F 19/00 | (2011.01) |

(52) U.S. Cl.
CPC .......... *G06F 8/65* (2013.01); *G06F 8/61* (2013.01); *G06F 9/44* (2013.01); *G06F 19/3412* (2013.01); *G06F 19/3418* (2013.01); *G06F 19/345* (2013.01)

(58) Field of Classification Search
CPC ..... G06F 8/65; G06F 8/61; G06F 9/44; G06F 19/3412; G06F 19/3418; G06F 19/345
USPC .......................................................... 713/2
See application file for complete search history.

(56) References Cited

U.S. PATENT DOCUMENTS

| | | | |
|---|---|---|---|
| 8,954,719 B2* | 2/2015 | Dicks | A61B 5/1112 713/2 |
| 8,966,235 B2* | 2/2015 | Dicks | G06F 8/61 713/2 |
| 2005/0114852 A1* | 5/2005 | Chen | G06F 11/1433 717/168 |
| 2006/0174238 A1* | 8/2006 | Henseler | G06F 8/63 717/168 |
| 2007/0022328 A1* | 1/2007 | Tarra | G06F 11/1433 714/100 |
| 2008/0256348 A1* | 10/2008 | Prasad | G06F 15/16 713/1 |

* cited by examiner

*Primary Examiner* — Robert Cassity
(74) *Attorney, Agent, or Firm* — Gregory J Gonsalves

(57) ABSTRACT

There is provided a method and system to automatically provide software and/or firmware updates to the electronic devices, particularly mobile devices used by consumers such as portable health-care data interchange devices. There is also provided a method and system of updating software in electronic devices without requiring a wired data interface to affect changes. There is also provided a method and system for tracking the configuration of electronic devices that are sold to and configured by particular consumers, especially consumers/patients using electronic devices related to health care. Further, there are also provided a methods and systems for integrating the purchase, and ordering, and software configuration of electronic devices.

12 Claims, 42 Drawing Sheets

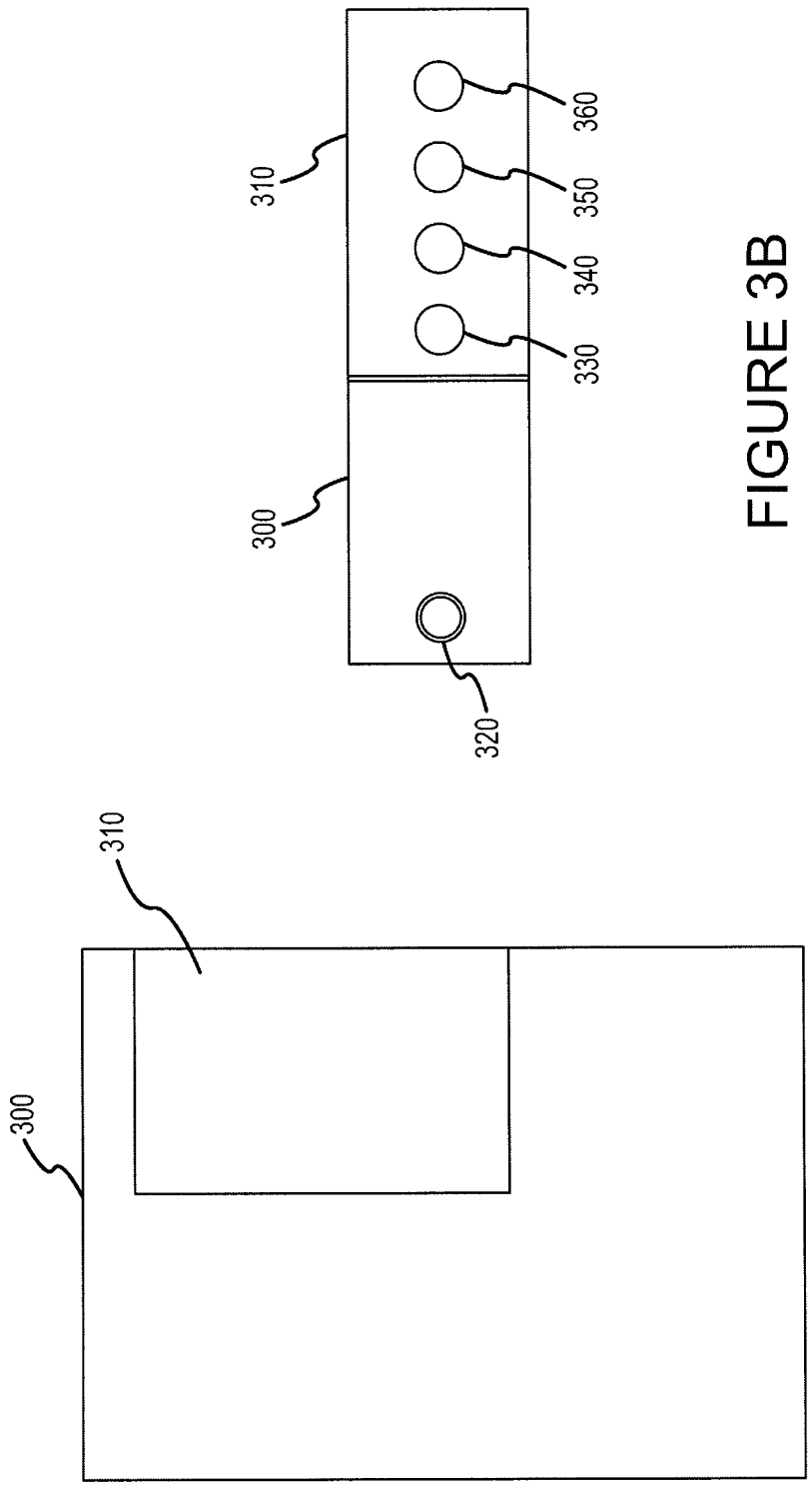

| Bit | | | | | | | | # of Bytes |
|---|---|---|---|---|---|---|---|---|
| 7 | 6 | 5 | 4 | 3 | 2 | 1 | 0 | |
| Protocol Version = 254 / 255 | | | | | | | | 1 |
| Enfora ID | | | | | | | | 8 |
| Length, not including Protocol Version or CRC (= 28) | | | | | | | | 2 |
| Number of Readings (= 1 to download, 0 to disconnect) | | | | | | | | 1 |
| Device Type (= 4 i.e. HealthPAL) | | | | | | | | 1 |
| Device Name (= 1 i.e. MA105) | | | | | | | | 2 |
| Firmware version, e.g. 1.0.7.0 | | | | | | | | 4 |
| Hardware Version (e.g. 1.0.2.0) | | | | | | | | 4 |
| Length of Packet to Send (e.g. 1024) | | | | | | | | 2 |
| Offset Within File | | | | | | | | 4 |
| CRC-16 checksum | | | | | | | | 2 |
| Total | | | | | | | | 31 |

Fig. 254

| Field | Data Range | # of bits |
|---|---|---|
| Protocol Version | 0-255 | 8 |
| Enfora ID | 15 digits | 64 |
| Length | 0-65535 | 16 |
| Number of Readings | 0-255 | 8 |
| Device Type | 0-255 | 8 |
| Device Name | 0-65535 | 16 |
| Firmware Version | 4 bytes, e.g. version 1.0.7.0 would be 1070 | 32 |
| Hardware Version | 4 bytes, e.g. version 1.0.2.0 would be 1020 | 32 |
| Length of Packet to Send | 0-65535 | 16 |
| Offset Within File | 0-4294967295 | 32 |
| CRC-16 Checksum | 16 bit checksum | 16 |
| | Total | 248 |

| Response Code '0' |
| Length (2 bytes) |
| Offset (4 bytes) |
| binary data (typically 1024 bytes) |
| CRC-16 (2 bytes) |

SYSTEMS FOR REMOTE PROVISIONING OF ELECTRONIC DEVICES

CROSS-REFERENCE TO RELATED APPLICATION

The present application is a continuation application of application Ser. No. 12/940,944 ("the '944 application"), The '944 application claims priority to U.S. Provisional Patent Application Ser. No. 60/862,743, filed Oct. 24, 2006; and claims priority to and is a continuation in part of U.S. Patent Publication No. 20080097908 filed as U.S. Utility patent application Ser. No. 11/876,689 on Oct. 22, 2007; U.S. Patent Publication No. 20080097909 filed as U.S. Utility patent application Ser. No. 11/876,695 on Oct. 22, 2007; U.S. Patent Publication No. 20080097551 filed as U.S. Utility patent application Ser. No. 11/876,708 on Oct. 22, 2007; U.S. Patent Publication No, 20080103554 filed as U.S. Utility patent application Ser. No. 11/876,711 on Oct. 22, 2007; U.S. Patent Publication No. 20080103370 filed as. U.S. Utility patent application Ser. No. 11/876,713 on Oct. 22, 2007; U.S. Patent Publication No. 20080097910 filed as U.S. Utility patent application Ser. No. 11/876,719 on Oct. 22, 2007; U.S. Patent Publication No. 20080215360 filed as U.S. Utility patent application Ser. No. 111876,725 on Oct. 22, 2007; U.S. Patent Publication No. 20080097911 filed as U.S. Utility patent application Ser. No. 11/876,744 on Oct. 22, 2007; U.S. Patent Publication No. 20080097552 filed as U.S. Utility patent application Ser. No. 11/876,732 on Oct. 22, 2007; U.S. patent application Ser. No. 20080097917 filed as U.S. Utility patent application Ser. No. 11/877,525 on Oct. 23, 2007; U.S. Patent Publication No. 20080103555 filed as U.S. Utility patent application Ser. No. 11/877,541 on Oct. 23, 2007; U.S. Patent Publication No. 20080218376 filed as U.S. Utility patent application Ser. No. 11/877,550 on Oct. 23, 2007; U.S. Patent Publication No. 20080224852 filed as U.S. Utility patent application Ser. No. 11/877,582 on Oct. 23, 2007; U.S. Patent Publication No. 20080097550 filed as U.S. Utility patent application Ser. No. 11/877,930 on Oct. 24, 2007; U.S. Patent Publication No. 20080183502 filed as U.S. Utility patent application Ser. No. 111877,946 on Oct. 24, 2007; U.S. Patent Publication No, 20090234672 filed as U.S. Utility patent application Ser. No. 111877,966 on Oct. 24, 2007; U.S. Patent Publication No. 20080097793 filed as U.S. Utility patent application Ser. No. 111877,994 on Oct. 24, 2007; and U.S. Patent Publication No. 20090112769 filed as U.S. Utility patent application Ser. No. 111923,013 on Oct. 24, 2007; the disclosures of which are incorporated by reference in their entirety for all purposes.

STATEMENT REGARDING FEDERALLY SPONSORED RESEARCH OR DEVELOPMENT

Not applicable.

NOTICE OF INCLUDED COPYRIGHTED MATERIAL

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. All trademarks and service marks identified herein are owned by the applicant.

DESCRIPTION OF THE INVENTION

Field of the Invention

The present invention relates to the provisioning and tracking of software installed in mobile devices. More particularly, the present invention relates to the automatic download and installation of software and/or firmware in mobile devices, and for the tracking, ordering, and configuration of electronic devices.

Background of the Invention

Historically, patient medical care was often provided for in the patient's home or some other environment apart from a clinical setting. Physicians, midwives, or other healthcare providers would make house calls, observe patient symptoms, formulate diagnoses, and provide treatment. As the state of the art of health care evolved over time, the number of house calls made by healthcare professionals diminished. In large part, health care providers conducted fewer and fewer house calls because it became impractical to bring bulky medical diagnosis and test equipment to the patient. Likewise, it was not cost effective or intellectually feasible for patients to purchase and operate the complicated and expensive medical machines in a home setting. Therefore, the health care model changed dramatically, emphasizing patient visits to health care facilities where an assortment of state-of-the-art test equipment would be available to assist doctors in more accurately assessing and treating patients. This meant that patients were now expected to come to the doctor, rather than the other way around.

Innovations in electronics in the last twenty years have made available a large number of more affordable and patient-operable medical devices that obviated, at least in part, the need for the patient to go to a facility each time a medical test or device checkup was required. Size and expense were not the only factors making this possible; since the new devices provided sophisticated processing in smaller form factors, the technical complexity required to operate the devices were reduced to a level that would not overwhelm a layperson's knowledge. Unfortunately, although portable medical devices such as blood glucose meters now allow patients to perform tests outside the context of medical facilities, patients still need to meet with health care providers to discuss the results obtained.

Some medical devices include ports to allow the communication of data to and from the medical device through a cable or other wired connection. Medical devices that communicate through such wired connections allow healthcare providers to monitor the operation of the medical device, as well as to optionally monitor a patient's biological and biometric information, the patient's behavior, and other information pertinent to the treatment of the patient. However, the manner in which medical devices communicate data varies depending on the type and manufacturer of the device, and therefore, proprietary equipment has been designed to communicate with medical devices only using a specific type of wired connection based on the type of medical device being used.

Medical devices can communicate through a wide range of wired connections. In the context of this application, "wired connection" generally refers to any physical connection that a medical device can communicate through. For example, "wired connections" can also refer to a waveguide, such as an optical fiber. Other wired connections that can be used by various medical devices include various sizes of tip and sleeve (TS), tip, ring, and sleeve (TRS), and tip, ring, ring, and sleeve (TRRS) connections. Such connections are also commonly referred to as "RCA plugs," "phone plugs," and "stereo jacks" and commonly include plug diameters of 2.5 mm and 3.5 mm when used with medical devices. Other wired connections, such as serial peripheral interface bus (SPI) connections, universal serial bus (USB) connections, RS-232 serial connections, Firewire (IEEE 1394) and Ethernet connections may also be used. A wired connection can also include any soldered electrical connection, trace on a circuit board, or other physical connection. Each of these connections vary not only in the physical structure of the connection, but also in the communication protocols used to transfer data. It would thus be desirable to have the capability to communicate with a variety of medical devices regardless of the specific wired connection they use.

Some medical devices include wireless transmitters for the communication of data to and from the medical device. For medical devices implanted in a patient, such as a pacemaker, wireless communication allows a healthcare provider to monitor the operation of the medical device, and to optionally monitor a patient's biological and biometric information, the patient's behavior, and other information pertinent to the treatment of the patient. However, the manner in which medical devices communicate data varies depending on the type and manufacturer of the device, and therefore, proprietary equipment has been designed to wirelessly communicate with medical devices only on a specific frequency and using a particular data communication protocol based on the type of medical device being used.

In the United States, medical devices can broadcast on a wide range of frequencies. For example, older implantable devices use frequencies ranging from 32 KHz to 175 KHz. The Federal Communications Commission (FCC) has allocated three frequency bands for use with wireless medical device communication, known as the Wireless Medical Telemetry System (WMTS). The WMTS frequency bands include the frequency ranges of 608-614 MHz, 1395-1400 MHz, and 1427-1432 MHz. Additionally, the FCC has allocated a band specifically for use by implanted medical devices. This band is known as the Medical Implant Communication Service (MICS) and includes the 402-405 MHz frequency band. It would be desirable to have the capability to communicate with medical devices using any of these frequency bands using a wide variety of wireless protocols that might be broadcast by the devices.

To make patient monitoring more convenient, Remote Patient Monitoring (RPM) was developed. Remote Patient Monitoring (RPM) generally refers to monitoring one or more conditions of a patient without requiring the patient to visit a hospital, doctor's office, or other healthcare facility. RPM can increase the efficiency and effectiveness of providing care to patients while reducing costs. RPM can be particularly useful when a patient has a long-term or chronic disease that would otherwise require frequent visits to a healthcare facility and/or where a patient's treatment regimen should be modified based on changed patient conditions that are monitored by one or more medical devices, such as a pacemaker or glucose meter. For example, Type-I Diabetes patients (a lifelong condition) use glucose meters to monitor their blood sugar level to assist in determining when to take insulin—it would be desirable if such information could be quickly, easily, and effectively relayed to a heath care provider for review and analysis.

Conventional RPM generally involves the use of a specific monitoring device installed in a patient's home. The device collects data concerning the patient's condition and relays the data to a healthcare provider. Some conventional systems require a patient to manually enter the data. For example, a diabetes patient using a conventional system for RPM may be required to sample their blood sugar level using a glucose meter, take note of the reading, and then manually enter the level in the conventional system. There are drawbacks with these conventional devices. Because of their complexity and proprietary interfaces, many are very expensive, which reduces the cost-savings benefit of RPM. Additionally, they often require a land-line connection (such as phone or VPN) to transmit data and/or are physically bulky/heavy and therefore difficult to transport. Further-more, conventional systems are often unable to provide data to healthcare providers quickly where data must be manually entered by a patient, which can reduce the level of benefit the patient receives from RPM.

The purchase and configuration of electronic devices often requires consumers to download new software and install the downloaded software on the purchased devices. In one configuration, the operating "firmware" or software installed in a nonvolatile memory used by a processor/controller of the device is periodically updated by the manufacturer, and for consumers to have the most up-to-date versions of the firmware, they are instructed to periodically (especially after initial purchase) download and install updates to the firmware that was initially installed in the electronic devices prior to shipping to sales outlets. This process is commonly known as called "flashing" or "re-flashing" the firmware of an device. However, this process is often tedious, and requires consumers to take the time to periodically apply updates to their purchased devices. Further, many consumers are averse to the somewhat technical steps that may be required to update software or firmware on their electronic devices. In the health-care related industries, having out-of-date software on health-related electronic devices may represent safety concerns, and may prevent the user/patient from having access to the full capabilities of the health-care related electronic device. What is needed is a method and system to automatically provide software updates to the electronic device. What is also needed is a method and system of updating software in electronic devices without requiring a wired data interface to affect changes. What is also needed is a method and system for tracking the configuration of electronic devices that are sold to and configured by particular consumers, especially consumers/patients using electronic devices related to health care. What is also needed is a method and system for integrating the purchase, and ordering, and software configuration of electronic devices.

The present invention addresses these and other issues.

SUMMARY OF THE INVENTION

Methods and systems according to the present invention may operate in conjunction with any wired or wireless connection, including those described herein, and may operate in conjunction with multiple wired or wireless connections. In exemplary embodiments, methods and systems according to the present invention may be configured to receive medical device data transmitted in any format and from any medical device.

An exemplary method according to various aspects of the present invention includes receiving data from a medical device and transmitting a message including at least a portion of the received data to a provided medical data server. This exemplary method further includes receiving a command from the medical data server.

There is provided a method and system to automatically provide software and/or firmware updates to the electronic devices, particularly mobile devices used by consumers such as portable health-care data interchange devices. There is also provided a method and system of updating software in electronic devices without requiring a wired data interface to affect changes. There is also provided a method and system for tracking the configuration of electronic devices that are sold to and configured by particular consumers, especially consumers/patients using electronic devices related to health care. Further, there are also provided a methods and systems for integrating the purchase, and ordering, and software configuration of electronic devices.

In an embodiment there is presented a method for providing a nonvolatile storage medium including a stored application image; providing a memory including at least a shared memory space, a boot portion and an address portion, the boot portion including code that when executed by the processor may modify the application portion, wherein: the boot portion includes a boot startup executable code, a boot main executable code, and a boot interrupt service routine code; and the application portion includes an initial application image comprising application startup executable code, an application main executable code, and an application interrupt service routine code; executing code within the boot main executable code to determine that the initial application image requires updating; retrieving the stored application image from the nonvolatile memory; overlaying the application portion with the retrieved application image; and transferring execution control from the boot main executable code to the overlaid application startup code in the application portion.

Both the foregoing summary and the following detailed description are exemplary and explanatory only and are not restrictive of the invention.

BRIEF DESCRIPTION OF THE DRAWINGS

A more complete understanding of the present invention may be derived by referring to the detailed description and claims when considered in connection with the following illustrative figures.

FIGS. 3A and 3B depict top and rear views, respectively, of an external casing for a medical data interchange device according to various aspects of the present invention.

FIG. 25A is a first part of an illustration of a protocol to request binary (or ".bin") files to be downloaded.

FIG. 25 B is a first part of an illustration of a protocol to request binary (or ".bin") files to be downloaded.

FIG. 26 is an illustration of a downloaded packet format.

DETAILED DESCRIPTION OF EXEMPLARY EMBODIMENTS

Exemplary Method Using Wired Communication

Figure 1:
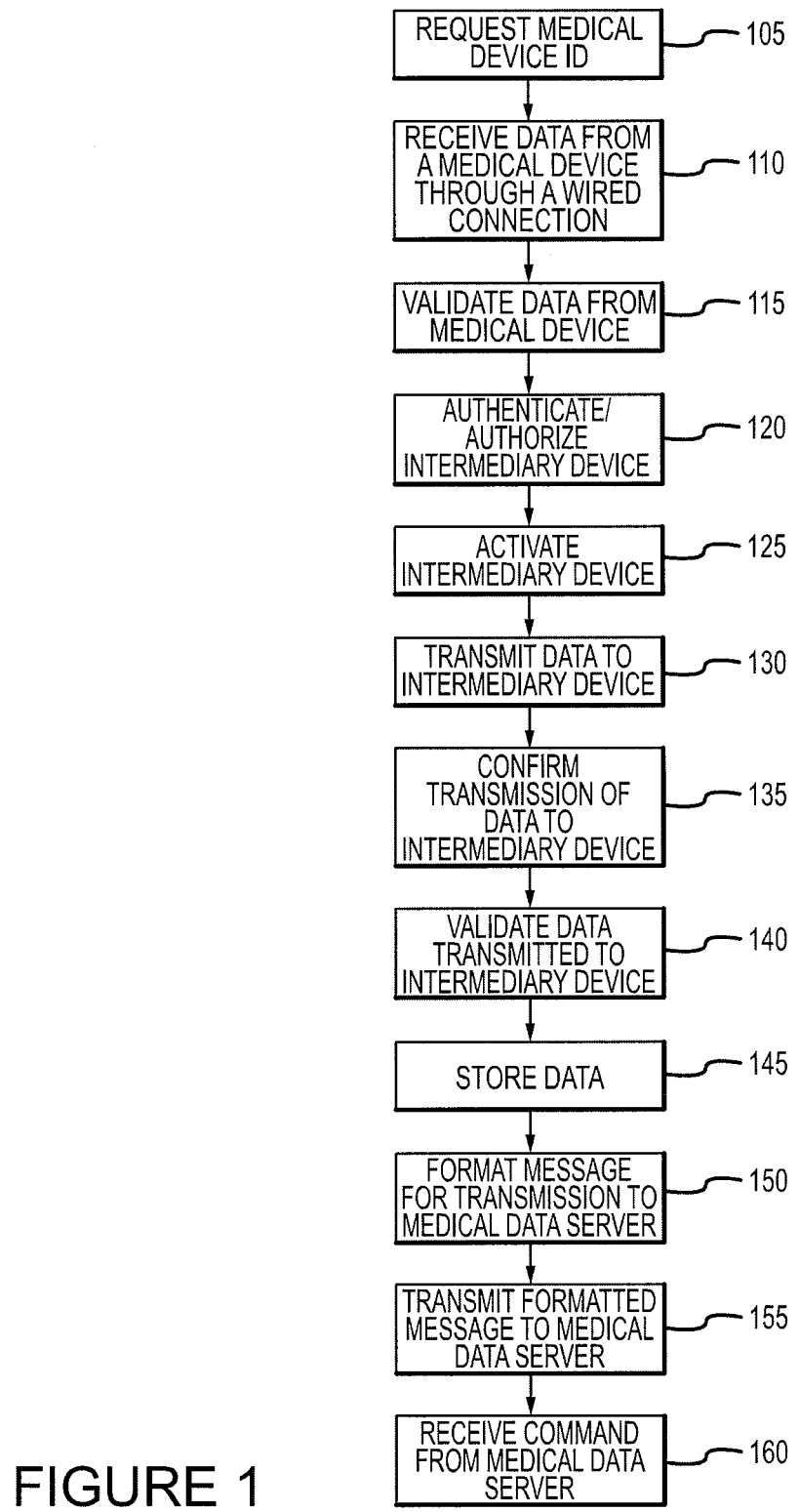
FIG. 1 is a flow diagram depicting an exemplary process for medical data interchange according to various aspects of the present invention.

An exemplary method according to an aspect of the present invention is depicted in FIG. 1. In this method, an identifier is requested from a medical device (105), and data from the medical device is received (110) and validated (115) through a wired connection. An intermediary device such as a mobile phone or personal digital assistant is authenticated (120) and activated (125). The data is transmitted by the medical device to the intermediary device (130) and the transmission to the intermediary device is confirmed (135) and validated (140). The data is stored (145) in the intermediate device. A message is formatted (150) and transmitted to a medical data server (155). Optionally, a command can be received from the medical data server (160) and optionally relayed from the intermediary device. Any combination and/or subset of the elements of the method depicted in FIG. 1 may be practiced in any suitable order and in conjunction with any system, device, and/or process. The method shown in FIG. 1 can be implemented in any suitable manner, such as through software operating on one or more computer systems. Exemplary systems for performing elements of the method shown in FIG. 1 are discussed later in this description.

Request Medical Device ID

In the exemplary process according to aspects of the present invention depicted in FIG. 1, an identifier is requested from a medical device providing the data to be monitored (105). Any suitable identifier may be provided, such as the serial number of the medical device and/or a numeric, alphabetic, alphanumeric, or symbolic identifier. The medical device identifier can be used to determine whether the correct medical device is being monitored. The medical device identifier can also be used to determine the manufacturer, model, type, characteristics, or other information pertinent to the medical device and/or the patient(s) it monitors. The medical device identifier may be received passively, such as from a medical device that automatically includes its identifier as part of its telemetry broadcast. Alternatively, the medical device can be polled to request the medical device identifier. The medical device identifier need not be requested from the medical device each time the medical device is being monitored. For example, the medical device identifier may be stored in a storage medium for future reference.

Receive Data from a Medical Device Through a Wired Connection

In the exemplary method shown in FIG. 1, data is received through a wired connection from the medical device (110). As stated previously, a "wired connection" in the context of this application refers generally to any physical connection that allows communication between two devices. Wired connections thus include, without limitation: tip and sleeve (TS), tip, ring, and sleeve (TRS), and tip, ring, ring, and sleeve (TRRS) connections; serial peripheral interface bus (SPI) connections; universal serial bus (USB) connections; RS-232 serial connections, Ethernet connections, optical fiber connections, and Firewire connections. Data from a medical device may be received using any number and combinations of such connections, as well as any other type of connection. Additionally, medical device may communicate data through a wired connection using any suitable format and communications protocol.

Systems implementing the method depicted in FIG. 1 are preferably small, light, and portable, allowing patients monitored by medical devices to lead active lifestyles without being forced to remain close to a non-portable system receiving the data from the medical device. Data can be received from any medical device, such as a blood glucose meter, a pacemaker, a blood pressure monitor, an insulin pump, a pulse oximeter, a holter monitor, an electrocardiograph, an electroencephalograph, a blood alcohol monitor, an alcohol breathalyzer, an alcohol ignition interlock, a respiration monitor, an accelerometer, a skin galvanometer, a thermometer, a patient geolocation device, a scale, an intravenous flow regulator, patient height measuring device, a biochip assay device, a sphygmomanometer, a hazardous chemical agent monitor; an ionizing radiation sensor; a monitor for biological agents, a loop recorder, a spirometer, an event monitor, a prothrombin time (PT) monitor, an international normalized ratio (INR) monitor, a tremor sensor, a defibrillator, or any other medical device.

A medical device that includes a combination of different medical devices (such as those listed previously) may be monitored in accordance with the present invention. The medical device can be partially or completely implanted in a patient, such as in the case of a pacemaker. Data from the medical device can be received through any number of other relay devices, such as routers, hubs, bridges, switches, and modems. Where the medical device is completely implanted in the patient, such relay devices can receive data from the medical device wirelessly and retransmit the data through a wired connection. The medical device may also be located externally to a patient. The medical device may be connected to a patient (for example, through one or more electrodes), or operate independent of any coupling to a patient, such as a scale. The medical device may also operate in conjunction with a temporary interfacing with a patient, such as the case of the cuff of a blood pressure monitor encompassing the arm of a patient to take a reading.

Figure 2A:
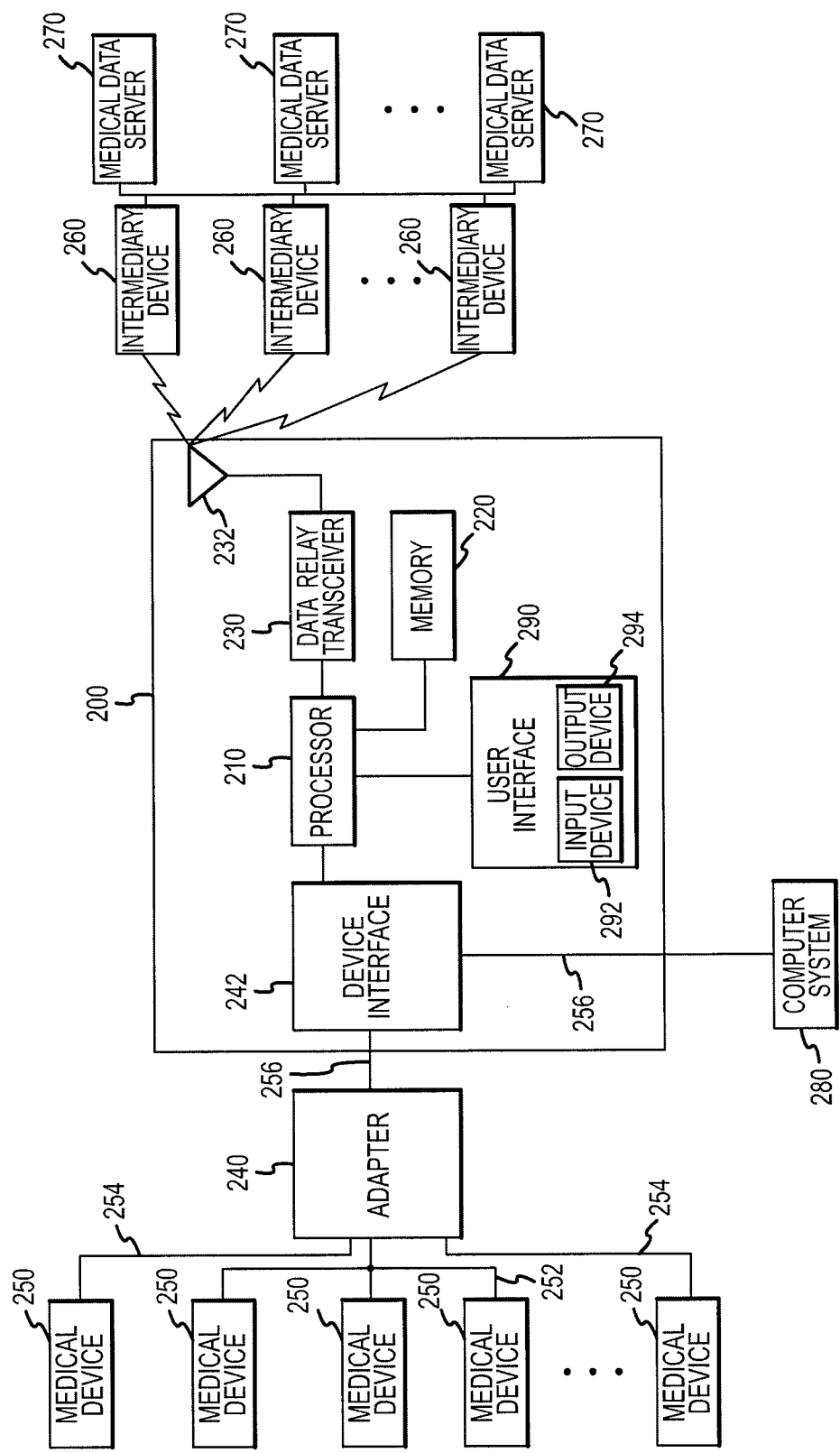
FIG. 2A is a block diagram depicting an exemplary system for medical data interchange according to various aspects of the present invention.
Figure 2B:
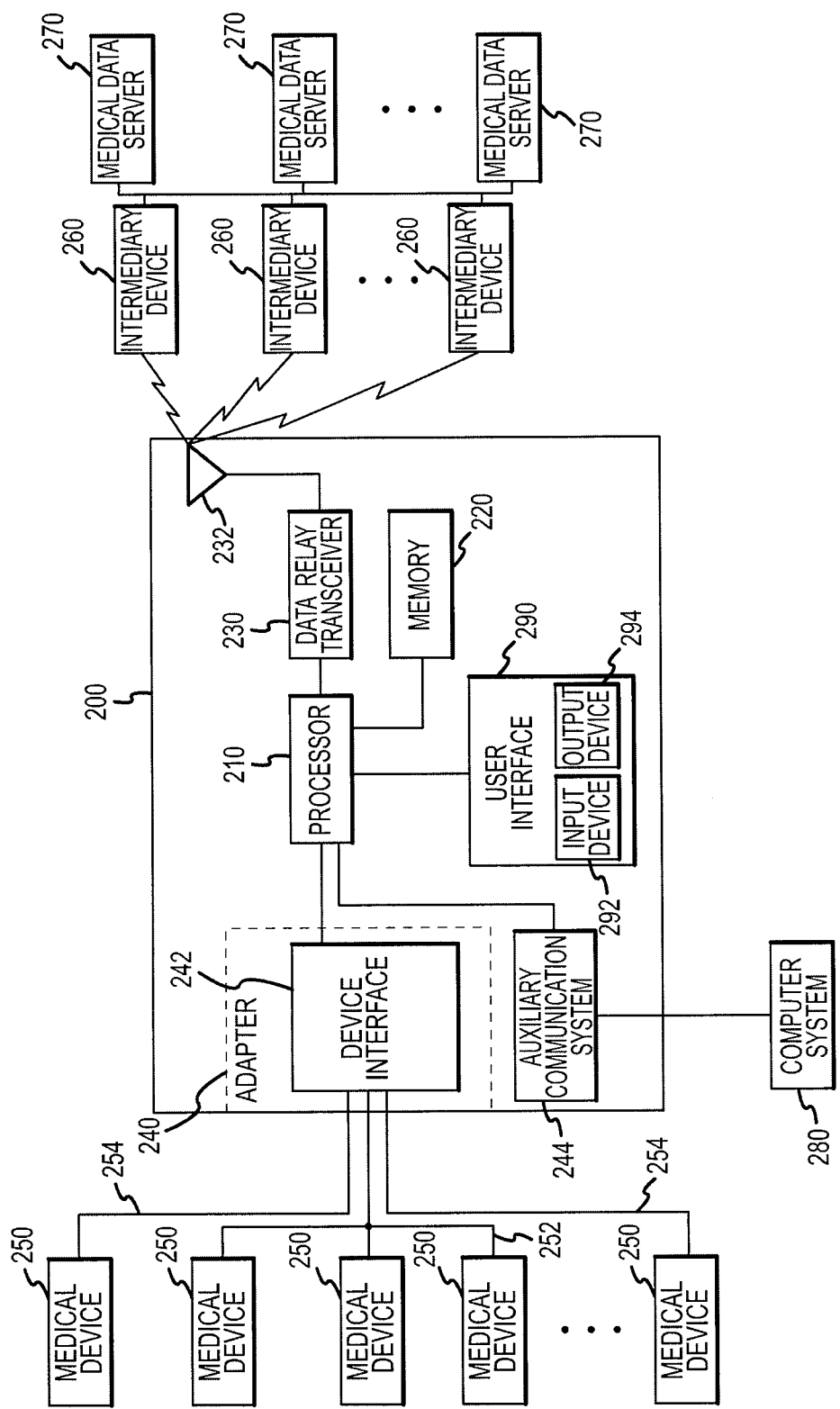
FIG. 2B is a block diagram depicting another exemplary system for medical data interchange according to various aspects of the present invention.
Figure 2C:
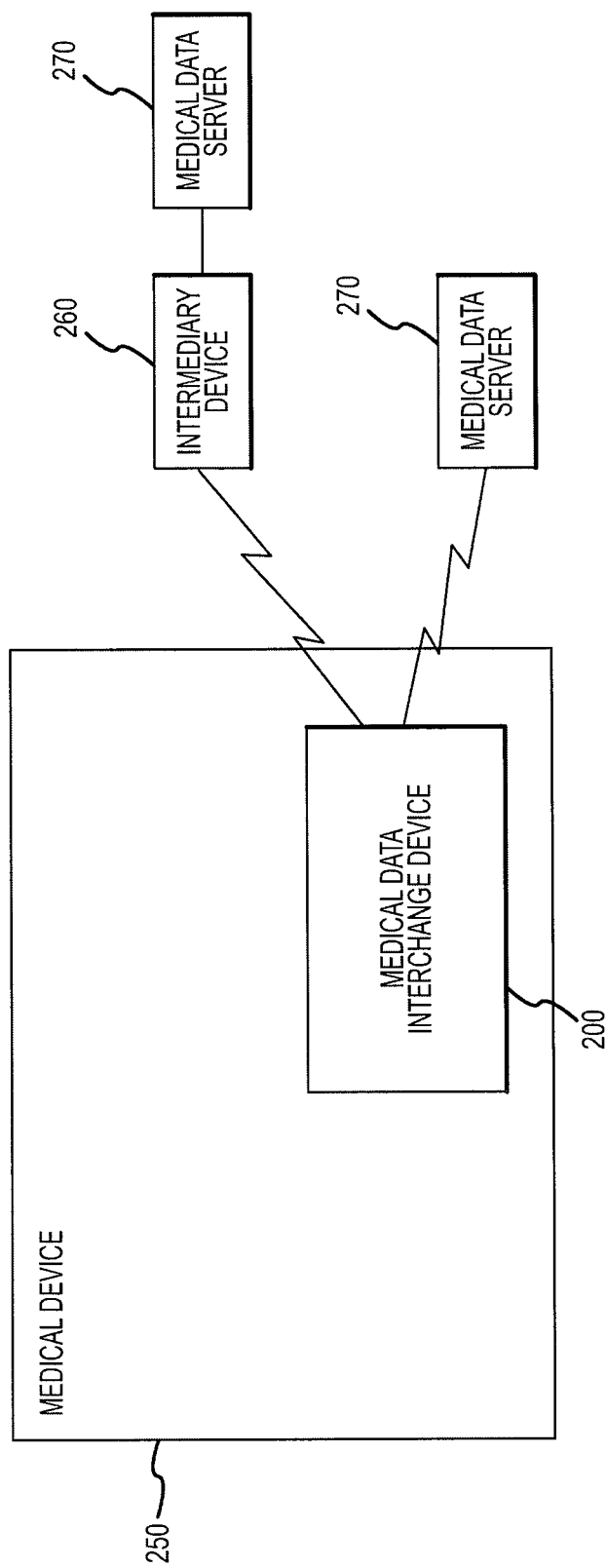
FIG. 2C is a block diagram depicting yet another exemplary system for medical data interchange according to various aspects of the present invention.

The medical device data can be received by any person, system, device, or other suitable recipient. The exemplary method in FIG. 1 may be practiced manually by a human being, automatically by a device, or a combination of the two. Exemplary devices for performing the method illustrated in FIG. 1 are depicted in FIGS. 2A, 2B, and 2C, and are discussed in detail below.

Data can be received directly from a medical device. For example, some medical devices such as glucose meters have ports that allow data to be communicated through a cable. As mentioned previously, a medical device can also provide data using another device, system, or other entity. In one embodiment of the present invention, for example, a medical device provides data through a serial port (a wired connection) to a computing device. The computing device is in turn connected to an Ethernet router or hub. The data can thus be received through an Ethernet connection from the router or hub. In another exemplary embodiment of the present invention, a human patient retrieves data from the medical device and then provides the data through a keypad, microphone, or other suitable input device.

The medical device data can be received from a plurality of different medical devices, where each medical device may perform any combination of functions. For example, data from a glucose meter, blood pressure monitor, and combination scale/height measuring device each transmitting data in different formats and through different wired connections may each be received in accordance with the present invention. In the case where a plurality of medical devices transmits data in response to a request for data, each device in the plurality of devices can be sent such a request separately. Alternatively, a plurality of medical devices automatically transmitting data in the same format, and potentially at the same time (such as in the case of multiple devices of the same type and/or from the same manufacturer) can be received in accordance with the present invention by, for example, using separate wired connections. When data has been received from a plurality of medical devices, in one embodiment, a list of the medical devices may be displayed on a user interface, and optionally, the user may be prompted to select one, all, or none of the plurality medical devices, whose data is desired to be transmitted to the medical data server. The data for the selected set of medical devices is then relayed as described with alternate embodiments as described herein. Any other suitable method for receiving data from a plurality of medical devices may also be used in conjunction with the present invention.

Any type of data may be received from a medical device. For example, the data may include information regarding a patient, such as the patient's biological and biometric information, the patient's behaviors, results of analysis of physical patient parameters, and information regarding the patient's environment. For example, a medical device such as a glucose meter could provide data regarding a patient's current (or last measured) blood glucose level, the date and time the patient last used the glucose meter, and the current temperature or other environmental factors that might affect a glucose test. Other possible environmental parameters that may be included in the data received from a medical device include a battery charge level, a temperature, a barometric pressure, a code relating to an accessory for the medical device, a data validity measurement, an elapsed time since a previous reading by the medical device, a test result parameter, a signal-to-noise parameter, and a quality of service (QoS), and combinations thereof. Data received from a medical device may also include any other suitable information, such as diagnostic information regarding the medical device.

The medical device data may provide data relating to a single patient or multiple patients. In the case where a single medical device provides data regarding multiple patients, the data can be identified with an individual patient either in the data received by medical device (such as by using a patient identifier) or through processing in accordance with the present invention.

The medical device can provide the data in any format. Different medical devices from different manufacturers often use different formats for providing data. For example, data from a glucose meter may be provided in a series of fixed-length data records followed by a terminator indicator (such as a null or other predefined character) and/or a checksum for validating the data. Any type of data may be provided. In the case of a glucose meter, the data may include one or more readings of a patient's blood glucose level and the date and time each reading was taken. The medical device identifier discussed previously may be used to determine a specific data format used by a medical device. Alternatively, a data format may be specified by a user or selected by analyzing the format of the data received and comparing it to a set of known medical device data formats.

Validate Data

In the exemplary process shown in FIG. 1, the data from the medical device is validated (115). The data from the medical device can be validated in any suitable manner to achieve any result. For example, the data from the medical device may be validated to ensure it was transmitted properly and completely. The medical device data may also be validated to ensure it was provided from a specific medical device or particular type of medical device. The data may also be validated to ensure that fields in the data correspond to predetermined values and/or are within certain thresholds or tolerances. Any number, code, value or identifier can be used in conjunction with validating the medical device data. For example, the data can be validated by analyzing a medical device serial number, a medical device identifier, a patient identifier, one or more parity bits, a cyclic redundancy checking code, an error correction code, and/or any other suitable feature.

Authenticate/Authorize Intermediary Device

In the exemplary method depicted in FIG. 1, an intermediary device receiving the data is authenticated (120). In the context of the present invention, the intermediary device includes any type of system or device capable of receiving the medical device data in any manner. Such intermediate devices may include, for example, personal computers, laptops, personal digital assistants, routers, hubs, bridges, switches, modems, and mobile computing devices. The intermediary device may process the data in any manner, and can transmit some or all of the data to another recipient, such as a medical data server. For example, but not by way of limitation, the intermediary device may include a personal computer or a mobile computing device, such as a laptop computer, a mobile wireless telephone, or a personal digital assistant (PDA). In an exemplary embodiment of the present invention, the intermediate device further includes software for receiving the medical device data, formatting a message based on the data, and transmitting the formatted message to a medical data server. Such software can operate on any suitable mobile computing device and with any computer operating system. The intermediary device may also include any number of other systems and devices suitable for receiving data from the medical device, processing the data, and/or transmitting the data to a medical data server. Further discussion regarding exemplary embodiments of intermediary devices is presented later in this description.

The intermediary device can receive the data directly from the medical device, or from one or more other devices. In one exemplary embodiment of the present invention, the intermediary device comprises a mobile computing device and is configured to receive data from one or more medical devices directly through one or more wired connections. In another exemplary embodiment of the present invention, the medical device transmits the data to a first device through a wired connection, which in turn transmits the medical device data to the intermediary device (wirelessly or through a wired connection).

The intermediary device may be authenticated to achieve any result. For example, transmission may be restricted only to authenticated devices operating as part of the present invention. Authentication can also prevent sensitive medical data from being viewed by unintended recipients. The intermediary device may also be authenticated to verify the intermediary device is able to receive, process, and/or transmit the medical device data to a medical data server. During authentication, the authenticated device or devices may also be remotely commanded, and such commands may include steps that configure devices to interoperate with components of the present invention. For example, but not by way of limitation, such steps may include the downloading of software applications, applets, embedded operating code, and/or data.

The intermediary device can be authenticated in any manner. For example, an intermediary device can be authorized to receive data from one or more medical devices using an authorization code. The authorization code can be any number, code, value or identifier to allow the intermediary device to be identified as a valid recipient of the data from the medical device. In one exemplary embodiment of the present invention, an intermediary device stores an authorization code and broadcasts the authorization code in response to a request for authorization. Unless the authorization code matches a code stored by the transmitter of the medical device data (such as the medical device itself or another transmission device), the medical device data is not transmitted to the intermediary device. Transmission of the medical device data to the intermediary device need not necessarily be predicated upon successful authentication of the intermediary device, however. For example, where the medical data is related to a medical emergency, the medical data could be transmitted to any suitable intermediary device within range, whether or not any intermediary device is actually able to be authenticated or authorized to receive the data.

In another exemplary embodiment of the present invention, an intermediary device receiving the medical device data using a wireless network protocol (such as Bluetooth) is authenticated based on whether the intermediary device advertises one or more services. In this context, advertised services reflect functions, utilities, and processes the intermediary device is capable of performing. The intermediary device broadcasts indicators of this functionality, thus "advertising" them to other systems and devices. In the present exemplary embodiment of the invention, unless the intermediary device advertises a service that is identifiable with the operation of the present invention (i.e. a process capable of broadcasting the medical device data to a medical data server, for example), the intermediary device is not authenticated and thus the medical device data is not transmitted to the intermediary device.

Activate Intermediary Device

In the exemplary process depicted in FIG. 1, the intermediary device can be activated (125) prior to transmitting the medical device data to the intermediary device. Many devices, particularly mobile computing devices running on batteries, employ power-saving features to conserve battery life when not in use. In the case where an intermediary device is in a power-saving or standby mode, it may be necessary to activate the intermediary device before it can receive the medical device data. The intermediary device can be activated in any suitable manner. For example, a signal configured to activate the device may be transmitted to prepare the intermediary device to receive the medical device data.

Transmit Data to Intermediary Device

The medical device data is transmitted to the intermediary device (130) in the exemplary process depicted in FIG. 1. The data can be transmitted in any suitable manner. In one exemplary embodiment of the present invention, the medical device data is transmitted to the intermediary device using a wired connection, such as an RS-232 serial cable, USB connector, Firewire connector, or other suitable wired connection. The medical device data can also be transmitted to the intermediary device wirelessly using a wireless transmitter. Any suitable method of wireless communication can be used to transmit the medical device data, such as a Bluetooth connection, infrared radiation, Zigbee protocol, Wibree protocol, IEEE 802.15 protocol, IEEE 802.11 protocol, IEEE 802.16 protocol, and/or ultra-wideband (UWB) protocol. If desired, the medical device data could be transmitted to the intermediary device using both a wired and wireless connection, such as to provide a redundant means of communication, for example.

Any amount of medical device data can be transmitted to the intermediary device in any manner. For example, data from the medical device can be transmitted to the intermediary device in real-time as it is measured, or medical device data can be stored (such as in a memory storage device) for a period of time before being transmitted to the intermediary device. In some cases, for example, it may be more efficient to transmit blocks of medical device data at once rather than initiating communication with an intermediary device each time data is available from the medical device. In other cases, the intermediary device may be out of range or otherwise unavailable to receive the medical device data. The medical device data can also be stored for any desired length of time, and/or until a particular event occurs. For example, the medical device data could be stored until it is verified that the intermediary device and/or the medical data server have received the data, allowing the data to be retransmitted if necessary. Data can also be deleted when a data record exceeds a predetermined storage time, and/or the oldest data record is deleted first after a predetermined storage size limit has been reached.

The medical device data can be transmitted to the intermediary device in any format. For example, the data from the medical device can be transmitted to the intermediary device exactly as it is transmitted from the medical device. This would be the case in embodiments of the present invention where the medical device itself is transmitting the data directly to the intermediary device. Alternatively, in embodiments of the present invention where the data is being received from the medical device and then retransmitted to the intermediary device, the medical device data can be reformatted, modified, combined with other data, or processed in any other suitable manner before being transmitted to the intermediary device. For example, the medical device data can be encrypted prior to transmission to the intermediary device, and this encryption may occur at any stage, for instance in the medical device itself or at a stage after being transmitted by the medical device. In cases where the medical device data is being combined with other data and transmitted to the intermediary device, all of the data may be encrypted or simply the medical device data itself. In an alternate embodiment, a digest of the medical data may be encrypted, to digitally "sign" the data contents to verify its authenticity. For example, but not by way of limitation, this digest may be produced by providing the received medical data to a hashing algorithm such as the MD5 or SHA-1 Secure Hashing Algorithm as specified in National Institute of Standards and Technology Federal Information Processing Standard Publication Number 180-1.

Asymmetric encryption algorithms and techniques are well known in the art. See, for example, RSA & Public Key Cryptography, by Richard A. Mollin, CRC Press, 2002, and U.S. Pat. No. 4,405,829, issued Sep. 20, 1983, the disclosures of which are fully incorporated by reference herein for all purposes. In an illustrative example, if two parties (for example, "Alice" and "Bob") wish to communicate securely using public key cryptography, each party begins by generating a unique key pair, where one of the keys is a private key that is kept in confidence by that party, and the other key is a public key that may be publicly distributed, published only to a message recipient, or made available through a public key infrastructure. The key generation step need be done by a party only once, provided that the party's private key does not become compromised or known by another party. If Alice wants to send a message confidentially to Bob, she may use Bob's public key to encrypt the message, and once sent, only Bob can decrypt and view the message using Bob's private key. But if Alice also wanted Bob to have assurance that the message was in fact coming from her, she could further encrypt the message with her private key before sending, then when Bob's private key and Alice's public key are used to decrypt the message, Bob knows for certain that he was the intended recipient and that Alice was the one who originated the message, and Alice knows that only Bob will be able to decrypt and read her message.

Asymmetric cryptography may be utilized to enhance security of certain implementations of the present invention. In an alternate embodiment, data transmitted by a medical device 250 is encrypted with a private key of the medical device user (or optionally with the private key of a health care provider that is operating the medical device), or with a public key of the intended recipient system such as the medical data server 270, or with both keys. The private and/or public keys may be delivered to the medical data interchange device 200 through a wired or wireless connection, allowing the medical data interchange device 200 to be configured for secure operation. In one embodiment, the system or medical data server 270 may request that the public key of the medical device be forwarded to enable decryption of any medical information encoded with the user's private key. In this manner, the data may be authenticated as coming from the actual patient that is desired to be monitored, and optionally, the patient may also be assured that only the intended recipient system or medical device server 270 is capable of decrypting and gaining access to the patient's medical device data.

In an alternate embodiment, encrypted or unencrypted data can be transmitted through an encrypted transmission protocol, such as the wireless encryption protocols (WEP, WPA and WPA2) associated with the IEEE 802.11 wireless protocols or a Bluetooth encryption protocol associated with IEEE 802.15. Any number of other encryption methods can be used to encrypt the medical device data in conjunction with the present invention. The intermediary device may decrypt the medical device data, to allow processing of the data for example. Alternatively, to protect the data from unauthorized viewing, an intermediary device could simply retransmit the encrypted data to the medical data server.

Confirm Transmission of Data to Intermediary Device

The transmission of the medical device data can be confirmed (135) to verify the transmission was successful. The transmission can be confirmed in any suitable manner. For example, the intermediary device can transmit an acknowledgement once the transmission is received, otherwise the transmission can be rebroadcast.

Validate Data Transmitted to Intermediary Device

In the exemplary process shown in FIG. 1, the data transmitted to the intermediary device is validated (115). The data from the medical device can be validated in any suitable manner to achieve any result. For example, the data from the medical device may be validated to ensure it was transmitted properly and completely. The medical device data may also be validated to ensure it was provided from a specific medical device or particular type of medical device. The data may also be validated to ensure that fields in the data correspond to predetermined values and/or are within certain thresholds or tolerances. Any number, code, value or identifier can be used in conjunction with validating the medical device data. For example, the data can be validated by analyzing a medical device serial number, a medical device identifier, a patient identifier, one or more parity bits, a cyclic redundancy checking code, an error correction code, and/or any other suitable feature.

Store Data

The intermediary device may store the medical device data (145). The intermediary device may store the data in any suitable manner, such as by using a memory storage device. Any portion or amount of medical device data (or other forms of information) received or generated by the intermediary device may be stored for any length of time. The data may be stored for a predefined period of time and/or until an event occurs. For example, in one embodiment of the present invention the data is stored by the intermediary device until the data has been transmitted to the medical data server. In another embodiment, data is stored by the intermediary device until a predetermined data transmission record size has been reached, so as to reduce communication charges that may accrue during transmission. In yet another embodiment, the intermediary device stores the data until an acknowledgment from the medical data server is received, where the acknowledgment indicates that the stored data has been received by the medical data server. The medical data may be stored in any desired file format, as well as in an encrypted or decrypted state.

Format Message for Transmission to Medical Data Server

In the exemplary method according to an aspect of the present invention depicted in FIG. 1, a message is formatted for transmission to the medical data server. The message can originate from any entity operating in conjunction with the present invention. For example, the message may be created by the intermediary device, a device transmitting the medical device data to the intermediary device, or the medical device itself. The message can include some or all of the medical device data, as well as any other information useful to the medical data server. Multiple messages can be formatted to include any desired amount of medical device data. For example, in the case of data from a glucose meter, multiple messages may be formatted to each include a single glucose reading, or a single message could be formatted to include the last ten glucose readings taken by the meter. The message can include any other desired data from any suitable source. For example, real-time data from a medical device may be included in a message along with previously-transmitted data from the stored by the intermediary device creating the message. The message (in whole or in part) may be encrypted to protect the contents of the message from unintended viewers and/or the privacy of the patient being monitored.

The message provides the medical device information to the medical data server in a format the medical data server can recognize and utilize. The message can thus be formatted to only include portions of the medical device data needed by the server and/or additional information about a patient, the medical device, and/or the treatment regimen. The message can be of any desired format. For example, the message can be included in a file having a tokenized format such as standard ASCII text format, or any other suitable standardized file format, such as an MS Word document, MS Excel file, Adobe PDF file, or binary picture file (JPEG, bitmap, etc.). The data within such a file can be ordered in any manner and have any suitable delimiters, notations, or other features. For example, a list of multiple glucose level readings in a text file message could be provided chronologically by when the readings were taken, with comma or tab delimiters to denote the start and end of each reading. The message may also have a unique and/or propriety format.

The format of the message can also be based on the method by which the message is transmitted to the medical data server. For example, where the message is transmitted to the medical data server using a wireless mobile telephone such as a cellular phone, the message can be formatted as an SMS text message. Similarly, the message may be formatted as an XML record, email, and/or facsimile. The message can include multiple formats and/or multiple messages may be formatted having different formats for transmission in a variety of methods or to a variety of recipient medical data servers.

Transmit Formatted Message to Medical Data Server

The message is transmitted to a medical data server (160) to allow the medical device data to be analyzed and processed. The message can be transmitted to a single medical data server, or to a plurality of medical data servers. The medical data server can be any suitable recipient of the medical device data. For example, the medical data server can be a computer system or other device as well as a human recipient (such as a doctor, nurse, or other healthcare provider). The message may be transmitted to the medical data server by any entity operating in conjunction with the present invention, and need not be the same entity that received the medical data or formatted the message. For example, the message may be transmitted to the medical data server by the intermediary device, any device transmitting or receiving the medical device data, or the medical device itself.

The message can be transmitted to the medical data server in any suitable manner. For example, the message can be transmitted to the medical data server through a wired connection, such as a telephone line, fiber optic cable, and/or coaxial cable. The message may also be transmitted wirelessly using any suitable wireless system, such as a wireless mobile telephony network, General Packet Radio Service (GPRS) network, wireless Local Area Network (WLAN), Global System for Mobile Communications (GSM) network, Enhanced Data rates for GSM Evolution (EDGE) network, Personal Communication Service (PCS) network, Advanced Mobile Phone System (AMPS) network, Code Division Multiple Access (CDMA) network, Wideband CDMA (W-CDMA) network, Time Division-Synchronous CDMA (TD-SCDMA) network, Universal Mobile Telecommunications System (UMTS) network, Time Division Multiple Access (TDMA) network, and/or a satellite communication network. The message may be transmitted using any suitable combination of multiple wired and wireless communication methods. The transmission method selected to transmit the message to the medical data server can be chosen according to any desired criteria. For example, one or more transmission methods can be selected from a plurality of possible transmission methods to send the message based on each method's cost, time required to transmit, reliability, security, or any other suitable factor. Based on such criteria, the message may be stored until there is a suitable opportunity to transmit the message. For example, the message may be stored until an evening or weekend rate is available on a communications network.

Receive a Command from Medical Data Server

In addition to receiving the medical device data, the medical data server can transmit a command (160). The command can be received by the intermediary device, the medical device, and/or or any other suitable recipient. Any number of commands of any type may be transmitted by the medical data server. The command can be transmitted using the same variety of wired and wireless methods discussed previously for the transmittal of the formatted message. The command need not be transmitted using the same communication method with which the formatted messages are transmitted to the medical data server.

In one embodiment of the present invention, for example, the medical data server issues a command to reconfigure a software application operating on the intermediary device. In another embodiment, the medical data server issues one or more commands to control the functionality of the medical device. In yet another embodiment, the medical data server issues one or more commands to request that a public encryption key corresponding to the patient using a medical device be forwarded to the medical data server, or that a device associated with the present invention receive a public encryption key corresponding to an intended recipient such as a particular health care service provider or other known destination such as the medical data server. In another embodiment, the medical data server issues one or more commands to cause the medical device to perform a warm reset, a cold restart, or to reset a password.

The commands need not be sent directly to a device they are intended to control. For example, a command could be transmitted to an intermediary device, which in turn retransmits it (unmodified) to the medical device to be controlled. Alternatively, the intermediary device could receive a command from the medical server, analyze the command, and then transmit an appropriately formatted command tailored to the specific medical device to be controlled. In this manner, the medical data server need not be able to generate a command for each and every specific device it wishes to control, rather, it can send a command appropriate to a class of devices (i.e. glucose meters) and the intermediary device will appropriately translate the command to control the medical device. The commands from the medical data server can initiate/run diagnostic programs, download data, request the patient's public encryption key, download the intended recipient's public encryption key, and perform any other suitable function on the intermediary device, medical device, or other devices operating in conjunction with systems and methods of the present invention.

In one embodiment, a user of a medical device may interact with the medical data server, and as a result of such interaction, cause a command to be created by the medical data server and transmitted to the medical device. Such a user may comprise, for example, the patient associated with the medical device or a health care provider that is caring for the patient. In various embodiments, the user may interact with a system that includes the medical data server through a computer interface (e.g. a web browser), a portable digital assistant (PDA), a mobile communication device (such as a cell phone), an emergency medical beacon, a medical data interchange device, an interactive voice response (IVR) function associated with the system, or other suitable interface. In one scenario, for example, the user calls the IVR function through a cellular network or PSTN connection, and in response to guided voice prompts, the user either gives vocal input, button-press inputs such as by DTMF tones, or a combination of methods. Based on the user's inputs to the system, whether by IVR or other means, the medical data server may respond by generating a command that is ultimately transmitted to the medical device or an intermediary device. In one implementation, the medical data server could generate and transmit a command that instructs the medical device to transmit data to the medical data server either directly or through an intermediate device. Such data may represent, for example, medical or historical information regarding a patient or the user of the medical device; medical device diagnostic information; or environmental parameters such as a battery charge level, a temperature, a barometric pressure, a code relating to an accessory for the medical device, a data validity measurement, an elapsed time since a previous reading by the medical device, a test result parameter, a signal-to-noise parameter, or a quality of service (QoS) parameter. In one implementation, in response to user input or input associated with analysis of data uploaded to the medical data server, the medical data server causes a command to be transmitted to the medical device that instructs the device to take action that results in the administration of a prescribed dose of medication to the patient, or a prescribed shock to the patient's heart.

A command from a medical data server can be in any appropriate format and may include any suitable information. For example, a command may include data received from one medical device 250 to be delivered to another medical device 250 through the medical data interchange device 200. In this manner, a variety of medical devices can share data whether or not they are in communication with the medical data interchange device 200.

A command can also originate from an intermediary device 260. For example, a command to program or reconfigure one or more software programs on the medical data interchange device 200 depicted in FIGS. 2A, 2B, and 2C can be provided by an intermediary device 260 to the medical data interchange device 200 through the data relay transceiver 230. A command, as discussed above, may include multiple instructions, applets, or data elements to be processed, such as sections of executable code or interpretable scripts. Additionally, a user can program or configure a software program on any device operating in conjunction with the present invention through a suitable user interface, such as the user interface 290 of medical data interchange device 200.

In any system where commands can be sent remotely, security is always a concern, especially when a wireless implementation may provide an entry vector for an interloper to gain access to components, observe confidential patient data, and control health-sensitive components such as pacemakers and insulin pumps. In any digital data network, it is also possible that commands intended for one recipient may be misrouted to a patient or health care provider that was not the intended recipient of the command. Embodiments of the present invention provide for enhanced security in a remote command system while still allowing flexibility and minimal obtrusiveness.

In one embodiment, a command received by any of the components in FIG. 2A, 2B, or 2C may be authenticated before the command is either acted upon by the destination component, or forwarded to another component in the system. Authentication may be directed to determining (1) whether the command came from a trusted or authorized source and (2) that the recipient is actually the intended recipient of the command. In one implementation, source command authentication is achieved by determining whether the origin of the command is a trusted component or server, and one way to accomplish this determination is analyzing whether a command is properly digitally signed by the originator or some other authentication information is provided that assures the recipient component that the message or command is authentic and the recipient component is actually the intended recipient. In an alternate implementation, destination command authentication is accommodated by examining the contents of the message or an authorization code to determine the intended recipient, or alternatively decrypting the command or a portion of the command to verify the intended recipient.

In one embodiment, when commands are created by a command originator, the originator provides for a means to verify the authenticity and/or validity of the command by at least one of the following methods: (1) encrypting the command with a private key of the command originator; (2) generating a digest of the command (through a method such as a hashing algorithm discussed above) and optionally encrypting the hashed digest with the command originator's private key, or (3) utilizing a symmetric encryption scheme providing an authentication code (such as a cryptographically hashed password) that is compared to previously stored values. Then, when a system component receives the command along with any encrypted or cleartext certification data, the component may determine the command is valid by (1) attempting to decrypt an encrypted command message with the alleged originator's public key, (2) attempting to decrypt an encrypted digest with the alleged originator's public key, and comparing the result to a hashed value of the command, or (3) comparing a cryptographically hashed password for the alleged originator to known pre-stored values, and if a match is found, authorization is granted. As an additional step, if the command were optionally encrypted using the intended patient/provider's public key, then only the recipient is capable of decrypting the command, ensuring that only the truly intended patient's healthcare devices were being issued commands, and not an unintended third party. For example, in one embodiment, authenticating the command comprises decrypting at least part of the command using at least one of: a public key associated with the medical data server; a private key associated with a user of the medical device; and a private key associated with the medical device.

Authenticate User Access to Medical Data Server

Figure 9:
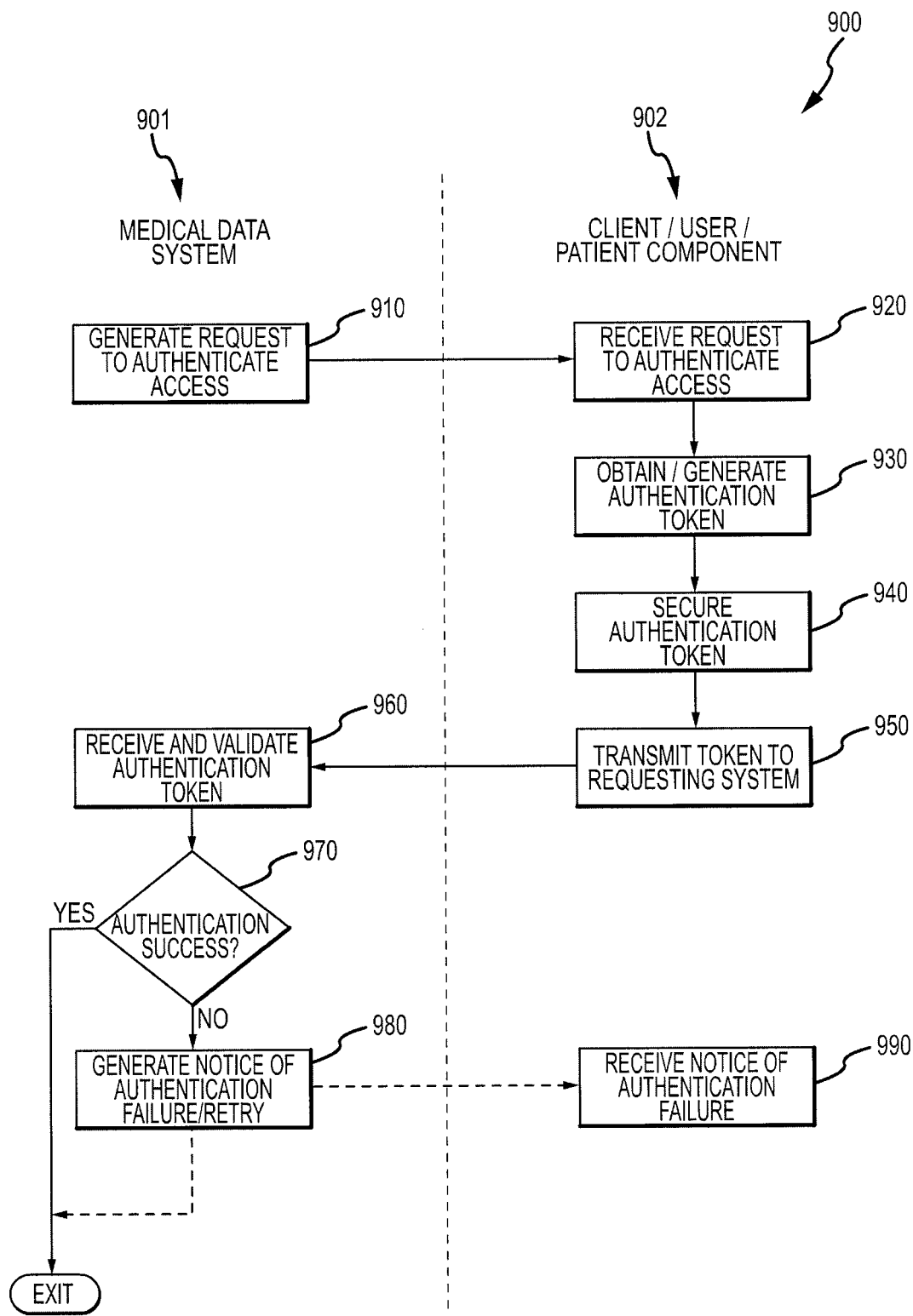
FIG. 9 is a flow diagram showing an exemplary process for authenticating access to a system component of the present invention.

In another embodiment, in regards to the methods described in regards to FIG. 1, it is desirable to ensure that a party attempting to interface with a system such as a medical data server is actually the party believed to be authorized to do so. Turning to FIG. 9, an embodiment is provided that illustrates a method to authenticate user access to the medical data server. A medical data system component 901 such as a medical data server (FIG. 2, 270) generates 910 a request to authenticate access, either on its own accord or as a result of a message received by an alleged patient who is enrolled in the medical service provided by the medical data server. The medical data system 901 then sends a request to authenticate access to a user component 902 of the present invention associated with the client, user, or health care provider, and in one implementation, such component may include the medical data interchange device 200. The user component 902 then receives 920 the request to authenticate access, and generates 930 an authentication token.

In various embodiments, authentication tokens may comprise either simple or complex text strings or data values indicating an account number or other patient identifier that can be matched against an internal patient database by the medical data server. Alternatively, authentication tokens may comprise encoded passwords or other indicia that assert that the entity for whom authentication is requested is genuine. Generation of an authentication token may be accomplished using alternative methods such as entry of a patient identifier, PIN, or password by a patient or healthcare provider after being prompted to do so. Alternatively, a biometric measurement of the patient or healthcare provider could be obtained and the measurement rendered into a digital representation. Once generated, for security purposes the authorization token may be secured 940 by encrypting the token, digesting and encrypting the digest of the token, or cryptographically hashing the token before transmission to the requesting entity such as the medical data system 901 or server. As discussed above in regards to the abovementioned command authentication, in one embodiment, when authentication tokens are created, the originating component of the token may create a certification of validity through at least one of the following methods: (1) encrypting the token with a private key associated with the token originator; (2) encrypting the token with a public key associated with the token requester or destination; (3) generating a digest of the token (through a method such as a hashing algorithm discussed above) and optionally encrypting the hashed digest with the token originator's private key, or (4) providing an authentication code as at least part of the token (such as a cryptographically hashed password) that may be is compared to previously stored values. Then, when a medical data system component 901 receives the token along with any encrypted or cleartext certification data, the component may determine the access is valid by (1) attempting to decrypt an encrypted token with the alleged originator's public key; (2) attempting to decrypt an encrypted token with the alleged originator's public key; (3) attempting to decrypt an encrypted digest with the alleged originator's public key, and comparing the result to a hashed value of the token, pin, code, or password, or (4) comparing a cryptographically hashed password for the alleged originator to known pre-stored values, and if a match is found, authorization is granted.

The medical data system component 901 then receives 960 and analyzes 970 the validity of the authentication token as described above. If examination of the authentication token provides that the token is authentic, such as by comparing the analyzed token data to known, pre-stored values such as the patient or the patient's health care provider's pre-stored hashed password or other identity datum, then access is successful and the process terminates. After analyzing the authentication token or a message containing or associated with the token, the medical data system may determine that access is either permitted or denied, and may communicate 980 this status to the originator of the authentication token 902 who then receives notice of the failure 990. At that point, the system may repeat the process 900, allowing the token originator to attempt access again.

Exemplary Systems Using Wired Communication

Exemplary systems for use in conjunction with the present invention are depicted in FIGS. 2A, 2B, and 2C. These systems may be used in conjunction with the method described in FIG. 1, as well as with any subset or combination of the elements thereof. The systems shown in FIGS. 2A, 2B, and 2C may also be used in conjunction with any other suitable embodiments of systems and methods for medical device monitoring according to an aspect of the present invention.

The exemplary system depicted in FIG. 2A is a medical data interchange device 200 that includes a processor 210 coupled to a memory 220. A data relay transceiver 230 wirelessly communicates with one or more intermediary devices 260 via antenna 232, which in turn communicates with one or more medical device servers 270 through either a wired or wireless protocol. An external adapter module 240 communicates with one or more medical devices 250. The adapter module 240 also communicates with a device interface 242, as can any number of external devices, such as a computer system 280. The device interface 242 may include any number of wired or wireless connections such as a universal serial bus (USB) connection, serial connection, parallel connection, Firewire connection (such as IEEE 1394), Ethernet connection, or any other suitable connection. Those of skill in the relevant arts also recognize that computer system 280 may also comprise external storage media such as a FLASH drive or a portable hard drive. The exemplary system shown in FIG. 2B includes a modular adapter 240 removably attached to the medical data interchange device 200. In one implementation of this embodiment, the device interface 242 is integrated with the adapter module 240.

The medical data interchange device 200 may include any suitable power connection for powering the interchange device and/or for recharging an energy storage device such as a battery (not shown). The components of the medical data interchange device 200 may receive electrical power from any other type of power supply.

The device interface 242 may establish unidirectional or bidirectional communications with one or more of the medical devices 250 through the adapter 240. The adapter 240 may be located internally or externally to the device interface 242 and/or medical data interchange device 200. In FIG. 2A, for example, the device interface 242 connects to an adapter 240 that is external to the medical interchange device 200, while FIG. 2B depicts the device interface 242 being integrated with the adapter 240.

FIG. 2C depicts an exemplary embodiment of the present invention wherein the medical data interchange device 200 is integrated with a medical device 250. The medical data interchange device 200 can be integrated with the medical device 250 using any number of suitable wired connections (i.e.—soldered connections and/or traces on a printed circuit board) to allow the medical data interchange device 200 to communicate with components in the medical device 250. As with the medical data interchange devices 200 depicted in FIGS. 2A and 2B, the medical data interchange device 200 depicted in FIG. 2C can communicate with any number of intermediary devices 260 and/or medical data servers 270.

The functionality of the medical data interchange device 200 can be implemented in any suitable manner, such as through the processor 210 executing software instructions stored in the memory 220. Functionality may also be implemented through various hardware components storing machine-readable instructions, such as application-specific integrated circuits (ASICs), field-programmable gate arrays (FPGAs) and/or complex programmable logic devices (CPLDs). Systems for medical data interchange according to an aspect of the present invention may operate in conjunction with any desired combination of software and/or hardware components.

Medical Data Interchange Device 200

Referring to FIGS. 3A and 3B, the medical data interchange device 200 depicted in FIGS. 2A and 2B is shown enclosed within a within a case 300. A case holding a system for medical data interchange according to aspects of the present invention may be of any size, shape and configuration. The system (and case enclosing it) is preferably small enough to be easily portable by a patient or person being monitored. For example, the exemplary case 300 depicted in FIGS. 3A and 3B is 3 inches long, 1 inch wide, and 0.5 inches deep. The top and bottom of the case 300 are 0.05 inches thick, while the sides of the case 300 are 0.075 inches thick. The case may be manufactured from any number of materials, such as plastic, metal, wood, composites, and/or any other suitable material. The case 300 shown in FIGS. 3A and 3B, for example, is manufactured from hard plastic.

The case 300 includes a power connection 320 for powering the interchange device 200 and/or for recharging an energy storage device such as a battery. The case 300 also includes an interface module 310 with four separate ports to accommodate different wired connections to the adapter 240, including a serial port interface (SPI) port 330, an infrared input 340, a mini-jack port 350 (i.e. —a 3.5 mm TRS connector), and a super mini-jack port 360 (i.e. —a 2.5 mm TRS connector). The interface module 310 may include any number and type of wired connection ports.

The interface module 310 may include any suitable portion of the medical data interchange device 200. In one embodiment, referring to FIG. 2B, the interface module 310 is an adapter module 240 that includes the device interface 242. The plurality of wired connection ports (330, 340, 350, and 360) are coupled to the adapter 240, which in turn communicates data to the rest of the medical data interchange device 200 through the device interface 242. In this embodiment, the interface module 310 is removably attached to the case 300 to allow different modules 310 to be interchangeably connected to the case 300 to communicate with different medical devices 250.

In another exemplary embodiment, referring again to FIG. 2A, the interface module 310 contains the device interface 242 that couples to an external adapter 240. In this embodiment, the adapter 240 includes one or more connections to one or more medical devices 250. The connections to the medical devices 250 can be through a common wired connection 252, such as a PCI bus, ISA bus, PCI-E bus, SPI, USB, or other common connection. The connections to the medical devices 250 may also be made through individual wired connections to each medical device 254. The adapter 240 can communicate with any number of medical devices 250 through any combination of common wired connections 252 and individual wired connections 254.

In the exemplary embodiment depicted in FIG. 2A, the adapter 240 also connects to the device interface 242, through one or more wired connections 256. The wired connection 256 between the adapter 240 and the device interface 242 can be a single shared wired connection that communicates data to and from every medical device 250 connected to the adapter 240. The adapter 240 can also communicate with the device interface 242 through a plurality of wired connections 256, wherein each wired connection 256 is dedicated to communicating with a separate medical device 250. The adapter 240 can also communicate with the device interface 242 through any combination of dedicated or shared connections.

The adapter module 310 may be removably attached to the rest of the case 300 to allow different modules with different types of wired connection ports to be interchangeably used, as depicted in FIG. 2B. The adapter module 310 may include any of the elements of the medical data interchange device 200, as well as any other desired systems and devices.

Figure 3C:
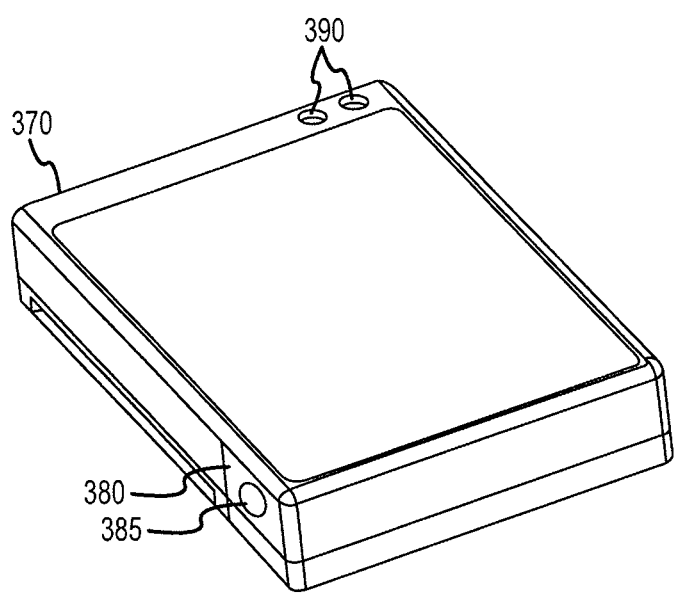
FIGS. 3C and 3D depict perspective views of another embodiment of an external casing for a medical data interchange device according to various aspects of the present invention.
Figure 3D:
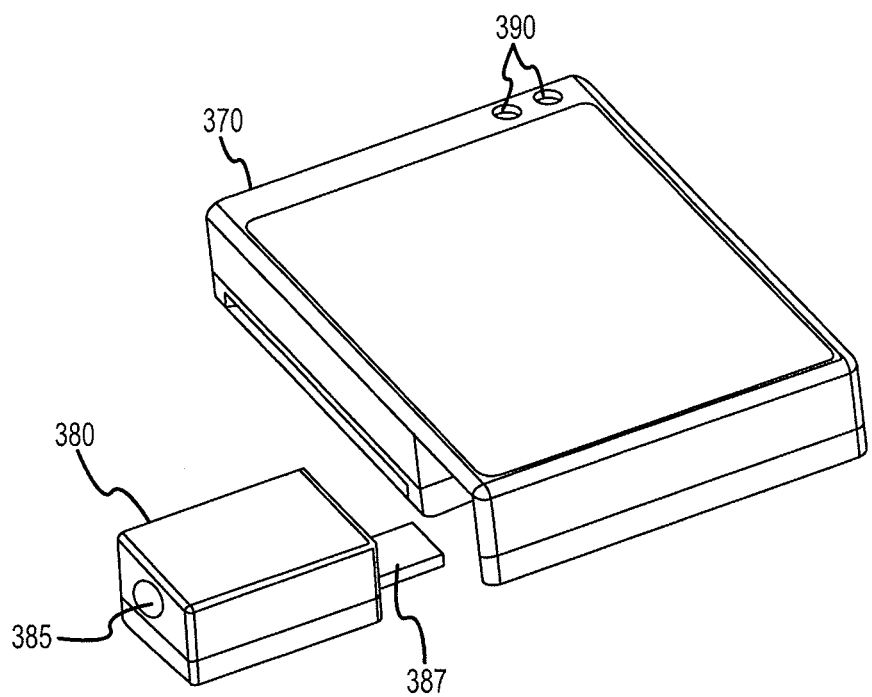
Figure 3E:
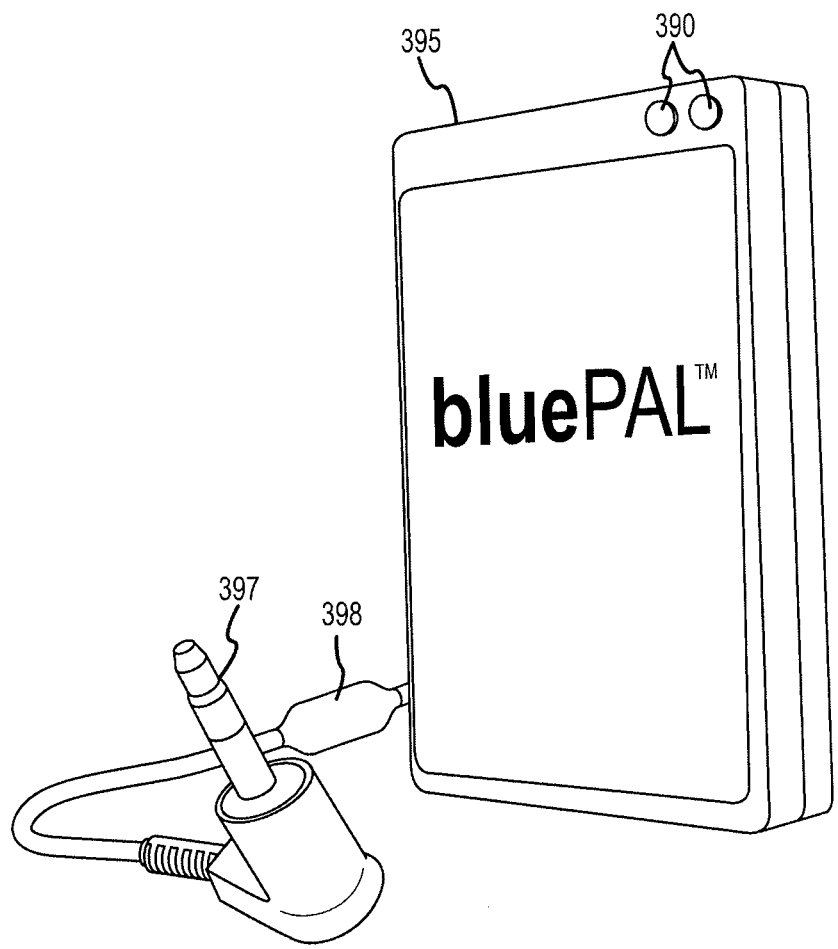
FIG. 3E depicts a perspective view of yet another embodiment of an external casing for a medical data interchange device according to various aspects of the present invention.

In another exemplary embodiment of the present invention, referring now to FIGS. 3C and 3D, a case 370 includes a removable adapter module 380 that includes a medical device connector 385 for communicating with a medical device through a wired connection. The adapter module 380 connects to the case 370 using plug 387. The plug 387 attaches to a corresponding port on the case 370 (not shown) to hold the adapter module 380 in place and allow the communication of data through the adapter module 380. The connector 385 and plug 387 can use any desired wired connection, and need not use the same type of wired connection. In one embodiment, for example, referring to FIG. 3E, a case 395 includes a 2.5 mm or 3.5 mm stereo plug connector 397 connected to a USB jack on the side of the case 395 (not shown). In this embodiment, the adapter module 380 is implemented in a component 398 that electrically couples the stereo plug connector 397 and USB jack. The component 398 includes circuitry (such as that depicted in FIGS. 6 and 7) to convert and/or redirect the signals from the stereo plug 397 to the USB jack and vice versa.

The adapter module 380 connects to the case 370 using plug 387. The plug 387 attaches to a corresponding port on the case 370 (not shown) to hold the adapter module 380 in place and allow the communication of data through the adapter module 380. The connector 385 and plug 387 can use any desired wired connection, and need not use the same type of wired connection. In the present embodiment, for example, the connector 385 is a 2.5 mm or 3.5 mm stereo jack while plug 387 is a USB plug.

The case can include any other suitable features. For example, the case may include a screen, lights, LEDs, keys, and speaker and microphone grilles to support features of a user interface included in a system for medical data interchange. The exemplary systems for medical data interchange shown in FIGS. 2A, 2B, 3A, 3B, 3C, 3D, and 3E are all configured to fit in a container along with the medical device it communicates with to allow a user to easily transport the medical device and the data interchange device together. In the exemplary system for medical data interchange depicted in FIG. 2C, the medical data interchange device 200 is integrated within the case or packaging of the medical device 250 itself.

Other embodiments of systems for medical data interchange according to aspects of the present invention can be configured to be in small enough to be coupled with or integrated into a medical device 250 or an intermediary device 260. For example, a medical device 250 may be manufactured to include a medical data interchange device 200 within the packaging or housing of the medical device 250. Similarly, a medical data interchange device 200 can be integrated as part of an intermediary device 260 such as a cellular phone, PDA, or other mobile computing device. The intermediary device 260 could thus be configured to both receive data from a medical device 250 through a wired connection, as well as transmit messages regarding the medical device 250 and/or patient to a medical data server 270.

Alternatively, a medical data interchange device 200 can be configured to be physically attached to a medical device 250 or intermediary device 260. For example, where an intermediary device 260 such as a mobile wireless telephone or PDA is used in conjunction with embodiments of the present invention, one exemplary embodiment of a medical data interchange device 200 and its case 300 is configured to match the size and shape of the of the intermediary device 260 and attach to the back of the intermediary device 260 using metal or plastic clips that wrap around the face and/or sides of the intermediary device 260. When attached, the medical data interchange device 200 conforms to the size and shape of the outline of the intermediary device 260, and is preferably shaped to conform to the dimensions of the back of the intermediary device 260 to avoid unnecessarily impacting the original size of the intermediary device 260. In this embodiment, the case of the medical data interchange device 200 may also include other desirable features, such as a belt clip to allow the data interchange device/intermediary device combination to be worn by a user.

Figure 4:
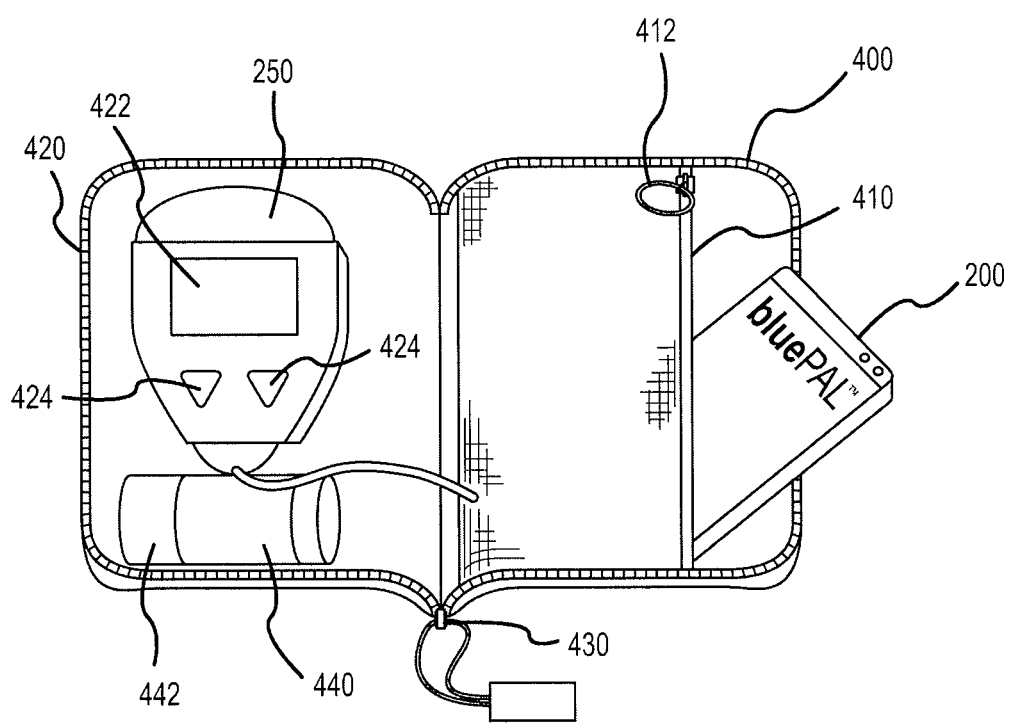
FIG. 4 depicts the interior of an exemplary container for holding a medical device and medical data interchange device according to various aspects of the present invention.

Turning to FIG. 4, in another exemplary embodiment of the present invention, the medical data interchange device 200 is contained in a flexible, protective container 400 that opens to allow a medical device 250 to be likewise contained therein. The container 400 could also be configured to hold an intermediary device 260 (such as a cellular phone, PDA, or other mobile computing device) to allow a medical data interchange device 200 to be used with a variety of intermediary devices 260, which may (in some cases) provide a more cost effective approach to integrate the medical data interchange device 200 with an intermediary device 260 or medical device 250. The medical data interchange device 200 can also be integrated within the protective container 400 itself, with the container 400 acting as the case for the data interchange device 200.

Alternatively, as depicted in FIG. 4, the medical data interchange device 200 may simply be contained within a pouch 410 or other structure within the container 400. The exemplary container 400 depicted in FIG. 4 also includes a holder 420 for the medical device 250 formed from clear plastic to allow a user to read a display 422 and/or operate keys 424 on the medical device 250. The protective container 400 can also be sized to comfortably fit and protect any other desired item, such as a day planner, wallet, notepad, and/or writing utensil or PDA stylus. The protective container 400 can be made from any combination of desired materials, such as leather, plastic, nylon, cordura, or other flexible material. The protective container 400 can be sealed in any manner, such as by using snaps, hook-and-loop closures, buttons, and/or a zipper. The exemplary container 400 depicted in FIG. 4, for example, is sealed using a zipper 430. The container 400 can be waterproof, heat resistant, and/or include padding to protect the medical data interchange device and other contents from the shock of a fall. The container 400 may include any number of pockets, pouches, or other sub-containers inside or outside the case to hold accessories associated with the medical device 250, intermediary device 260, or other item(s) stored within the container 400.

The exemplary protective container 400 depicted in FIG. 4 is configured to hold a medical device 250 (specifically, a glucose meter) and a medical data interchange device 200 according to an aspect of the present invention. In this exemplary embodiment, the protective container 400 is closed using a zipper 430 that runs along the exterior of the sides of the container 400. A user unzips the two halves of the container 400 and opens the container 400 to display the glucose meter contained in the holder 420 attached to the interior of one half of the container 400, while the medical data interchange device 200 is contained in a pouch 410 attached to the interior of the other half of the container 400. The pouch 410 is formed from a nylon mesh material to allow a user to see and/or interact with user interface features of the medical data interchange device 200. The pouch 410 is sealed with a zipper 412. The container 400 includes a flexible elastic strap 440 to hold a container of blood sugar metering strips 442. The container 400 may include any number of other pouches or containers on the interior or exterior of the container for storing batteries and/or power cables for the glucose meter and/or medical data interchange device, and other items of use to the patient carrying the container, such as bottles of insulin and needles for use by the patient depending on the outcome of a reading by the glucose meter.

Processor 210

Figure 5A:
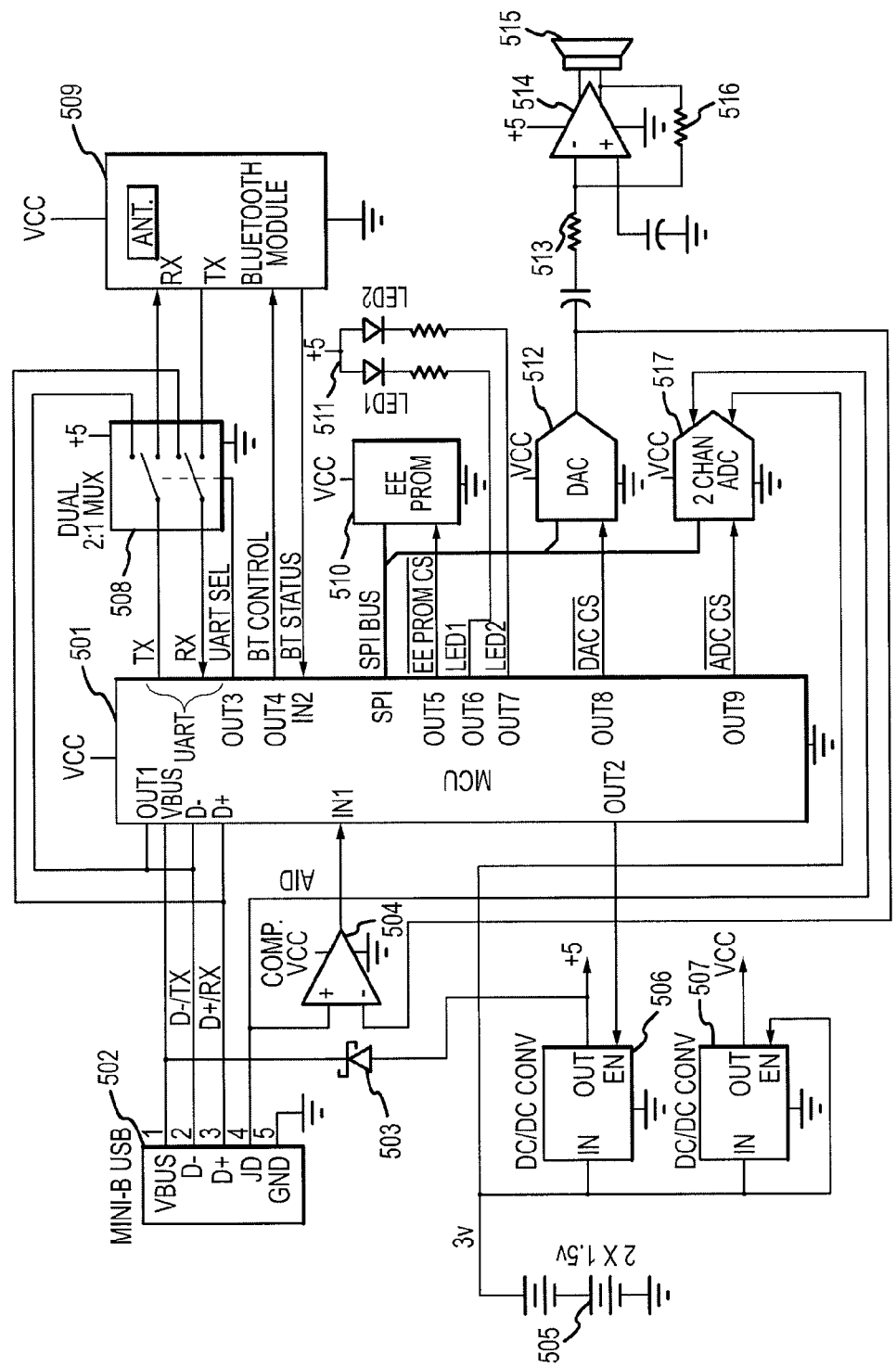
FIGS. 5A and 5B are a circuit diagrams depicting elements of an exemplary medical data interchange device according to various aspects of the present invention.

The processor 210 retrieves and executes instructions stored in the memory 220 to control the operation of the medical data interchange device 200. Any number and type of processor(s) such as an integrated circuit microprocessor, microcontroller, and/or digital signal processor (DSP), can be used in conjunction with the present invention. Referring now to FIG. 5A, an exemplary medical data interchange device 200 according to an aspect of the present invention is implemented using a microcontroller 501. In the exemplary system depicted in FIG. 5A, the microcontroller 501 includes a Universal Asynchronous Receiver/Transmitter (UART) and Universal Serial Bus (USB). The microcontroller 520 depicted in FIG. 5B also includes these features, along with a digital signal processor (DSP) for communication with a cellular RF Transceiver 530 as will be discussed in more detail below. The microcontrollers 501, 520 depicted in FIGS. 5A and 5B, respectively can include any other suitable components and features, such as comparators (504), analog-to-digital converters (ADCs) (517), and/or digital-to-analog converters (DACs) (512), though these components have been shown outside the microcontrollers 501, 520 for clarity.

Memory 220

The exemplary systems depicted in FIGS. 2A and 2B include a memory 220. The memory 220 stores instructions, medical device data, messages transmitted to or received from the medical data server 270, and any other suitable information. A memory 220 operating in conjunction with the present invention may include any combination of different memory storage devices, such as hard drives, random access memory (RAM), read only memory (ROM), FLASH memory, or any other type of volatile and/or non-volatile memory.

Figure 5B:
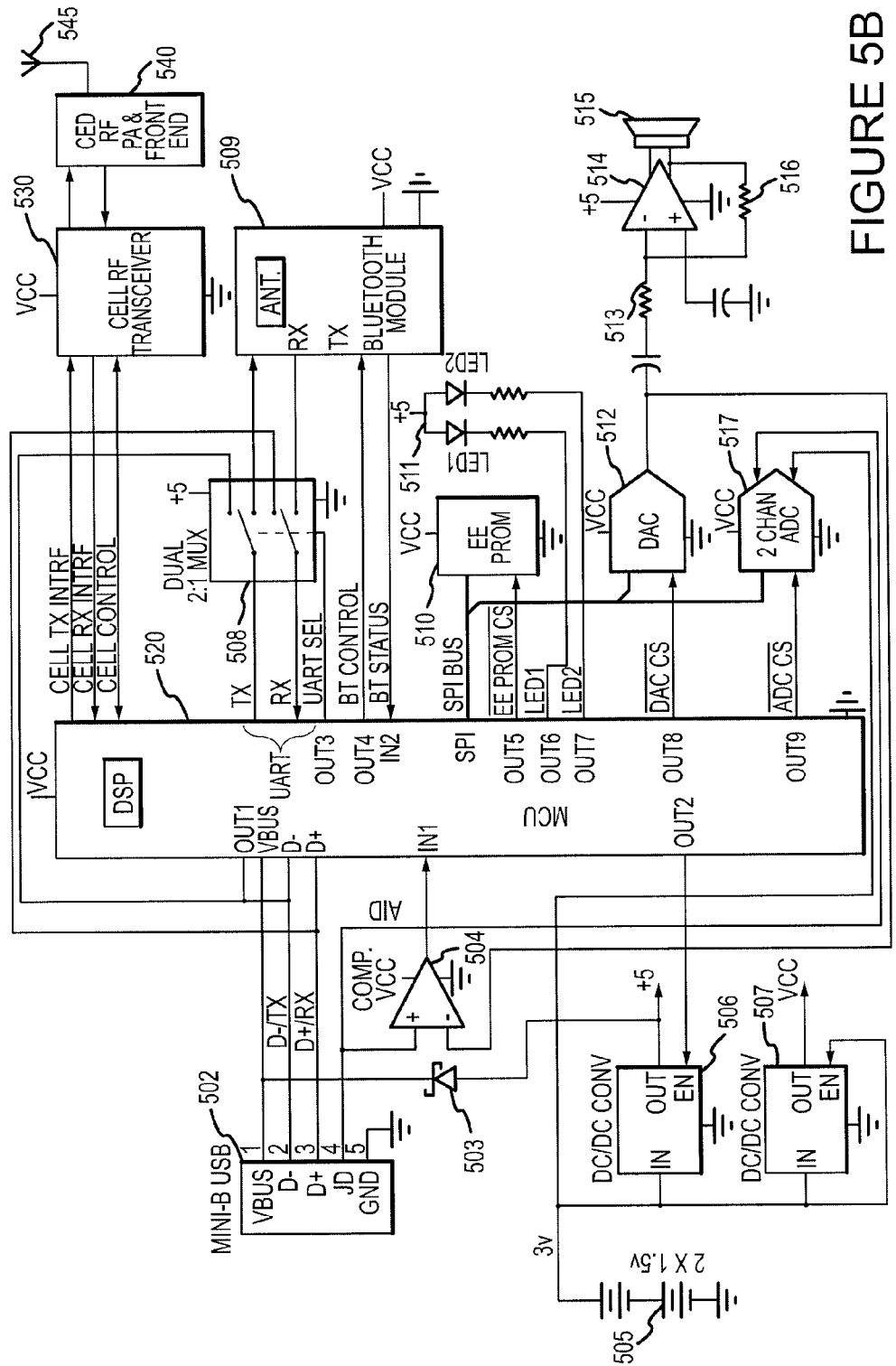

In the exemplary embodiments depicted in FIGS. 5A and 5B, the microcontroller 501 and 520 each include an on-chip memory. In addition, the microcontroller 501, 520 is coupled to a flash memory 510. The flash memory 510 may be of any size to achieve any desired purpose. In this exemplary embodiment, the size of flash memory 510 is selected to adequately store pre-recorded voice recordings to be played through the speaker 515, discussed below. Any number of memory storage devices of any size and configuration may also be used in conjunction with the present invention.

Power Source

Any number, combination, and type of suitable power sources can be utilized in accordance with aspects of the present invention. The exemplary systems depicted in FIGS. 5A and 5B are powered by a pair of replaceable alkaline AAA 1.5 volt batteries 505. The positive lead of the series-coupled battery pair 505 is connected to ADC 517 to enable the microcontroller 501, 520 to monitor the voltage level of the batteries 505. Any number of other suitable batteries may also be used according to any desired criteria. For example, a rechargeable battery or batteries integrated with the data interchange device may be selected to reduce the overall size of the medical data interchange device 200 and/or provide for the convenience of a user who would not need to replace batteries. Such rechargeable batteries can be charged through the USB connector 502, as well as through a dedicated power connector. Any battery of any suitable type and size may be used. Replaceable batteries may be selected to reduce the price of the medical data interchange device. The power supply circuitry shown in FIGS. 5A and 5B is exemplary only, and may be implemented by using other conventional power supply approaches. The medical data interchange device 200 and other systems for medical data interchange according to various aspects of the present invention can utilize any appropriate power supply devices, components, circuits, and systems.

In the exemplary circuits shown in FIGS. 5A and 5B, voltage from the batteries 505 is supplied to two DC to DC converters 506, 507 which supply an appropriate voltage level to the various components of the medical data interchange device 200. DC converter 506 steps up the voltage to 5 volts, while DC converter 507 steps up the voltage to 3.3 volts. Any number of voltage converters or similar components may be used as desired to supply appropriate voltage levels to components of the medical data interchange device 200.

Data Relay Transceiver 230

The data relay transceiver 230 communicates with one or more intermediary devices 260, medical data servers 270, or other suitable systems. Any suitable communications device, component, system, and method may be used in conjunction with the present invention. In the exemplary circuits shown in FIGS. 5A and 5B, the data relay transceiver 230 comprises a Bluetooth transceiver 509 that is in bidirectional communication with microcontroller 501, 520 through multiplexer 508. The multiplexer 508 allows the microcontroller 501, 520 to alternately communicate with the USB port 502 and the Bluetooth transceiver 509 through a single UART on the microcontroller 501, 520.

The medical data interchange device 200 may include, or operate in conjunction with, any number of data relay transceivers 230. In FIG. 5B, for example the exemplary medical data interchange device 200 further includes a cellular radio frequency (RF) transceiver 530 in communication with microcontroller 520. In this exemplary embodiment, the microcontroller 520 is a cellular baseband processor that includes a digital signal processor (DSP) which communicates data through a cellular RF power amplifier and front end 540 connected to a cellular antenna 545. Data is transmitted by the microcontroller 520 on the CELL TX INTRF line and received by the microcontroller on the CELL RX INTRF line. Additionally, the microcontroller 520 can control various features of the RF transceiver 530 via the CELL CONTROL line. The RF power amplifier and front end 540 performs the necessary functions to transmit and receive cellular signals, such as power amplification, power detection, filtering, and input/output matching.

The medical data interchange device 200 depicted in FIG. 5B may be configured to communicate using any number and type of cellular protocols, such as General Packet Radio Service (GPRS), Global System for Mobile Communications (GSM), Enhanced Data rates for GSM Evolution (EDGE), Personal Communication Service (PCS), Advanced Mobile Phone System (AMPS), Code Division Multiple Access (CDMA), Wideband CDMA (W-CDMA), Time Division-Synchronous CDMA (TD-SCDMA), Universal Mobile Telecommunications System (UMTS), and/or Time Division Multiple Access (TDMA). A medical data interchange device 200 operating in conjunction with the present invention may alternatively (or additionally) include data relay transceiver 230 components to communicate using any other method of wired or wireless communication.

As discussed previously, the medical data interchange device 200 can transmit any data to any entity operating in conjunction with the present invention. For example, the medical data interchange devices 200 depicted in FIGS. 5A and 5B may transmit medical data to one or more intermediary devices 260, as well as to one or more medical data servers 270.

Adapter Module 240

Referring again to FIG. 2A, the exemplary medical data interchange device 200 includes an adapter module 240 for communicating with one or more medical devices 250 as well as other suitable systems. The adapter module 240 can be configured to communicate with any suitable class, type, and/or manufacturer of medical device 250. The adapter module 240 depicted in FIG. 2A is an external component that communicates with a device interface 242 in the medical data interchange device 200. In the exemplary circuits depicted in FIGS. 5A and 5B, the USB port 502 is configured to interface with a standard USB connection, as well as with the adapter interfaces 601 and 701 (shown on FIGS. 6 and 7, respectively) which utilize USB connectors, but not the USB communications protocol. Instead, the adapters depicted in FIGS. 6 and 7 implement a customized protocol tailored to communicating with medical devices 250 through ring/tip connectors 605 and 705. The microcontroller 501, 520 is configured to detect and utilize the same communications protocol as an adapter module 240 connected to port 502.

In accordance with various aspects of the present invention, the adapter module 240 can also be modular and removably attached to the body of the data interchange device 200, integrated as part of the data interchange device 200, or a combination of the two. In the exemplary embodiment of the present invention depicted in FIG. 2B, an adapter module 240 is removably attached to the body of the medical data interchange device 200 and includes the device interface 242 to allow different medical devices 250 to interoperate with the data interchange device 200. As new medical devices 250 and/or new wired connections are utilized, a modular adapter module 240 configured to communicate with the new device or new frequency can be added to the existing system.

Software running on or operating in conjunction with the adapter module 240 can be configured/updated through the device interface 242, auxiliary communication system 244, the user interface 290, or in response to a communication from an intermediary device 260 or medical data server 270 received through the data relay transceiver 230. This allows the functionality of the medical data interchange device 200 to be dynamically updated and avoids the expense of having to create custom hardware implementations for every type of medical device to be monitored.

Figure 6:
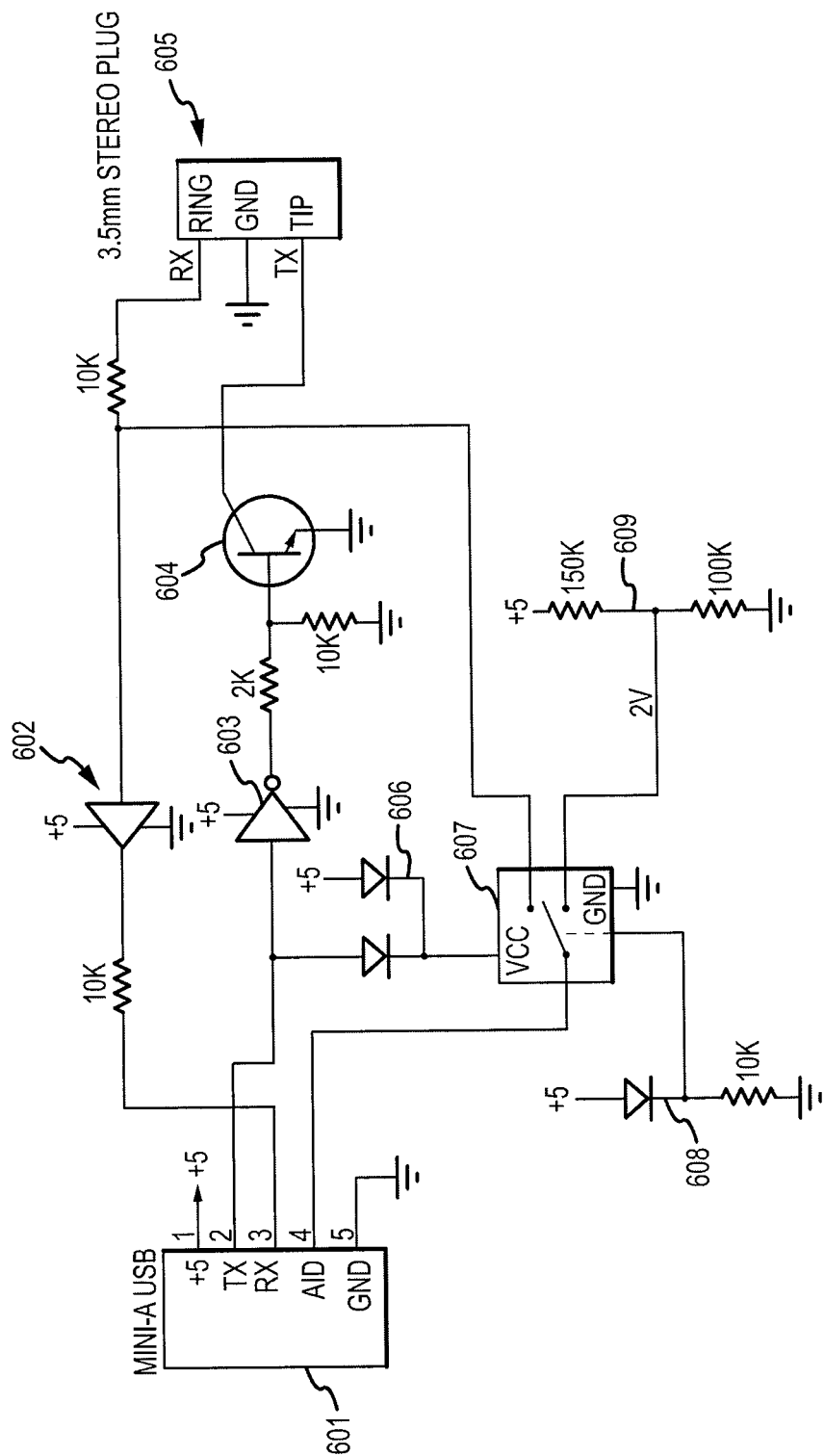
FIG. 6 is a circuit diagram illustrating elements of an exemplary embodiment of a smart cable with ID and wakeup capability.

FIG. 6 depicts a circuit diagram of an adapter module 240 that interfaces with the data interchange device 200 through a USB connector 601. As stated previously, the adapter 240 adjusts the voltage levels of Tx and Rx in order to communicate with a medical device 250 connected to TRS connector 605. An adapter 240 operating in conjunction with the present invention may use any combination of wired connections and communication protocols.

The adapter module 240 depicted in FIG. 6 is configured to interface with a medical device 250 that sends a wakeup signal. In operation, a signal received from the medical device 250 on the Rx line is provided to the USB connector 601 through a buffer 602 that provides isolation between the medical device 250 and the circuitry of the medical data interchange device 200 depicted in FIGS. 5A and 5B. The Rx signal is also provided to switch 607 which places a voltage on the AID pin of the USB connector 601. Referring back to FIGS. 5A and 5B, the voltage from the AID pin on connector 601 is provided to the comparator 504 through the ID pin on the USB port 502. The comparator 504 then activates the microcontroller 501, 520 in response. The level of voltage provided on the AID pin can also be used to identify the type of meter and/or adapter connected to the medical data interchange device 200 to the microcontroller 501, 520.

Referring again to FIG. 6, the Tx lead from the USB connector 601 is driven logically high when the UART on the microcontroller 501 is idle. The Tx signal from the USB connector 601 is inverted by inverter 603. When the UART on the microcontroller is idle, the inverter 603 drives the signal low, turning transistor 604 off and allowing the Tx signal to the tip of connector 605 to float at the voltage level from the medical device 250. Alternatively, when the UART on the microcontroller 501 is active, the Tx signal from the USB connector 601 is logically low and the inverter 603 inverts the low signal high to activate transistor 604 and allow the Tx signal from connector 601 to drive the Tx line on the TRS connector 605 to the medical device 250.

Figure 7:
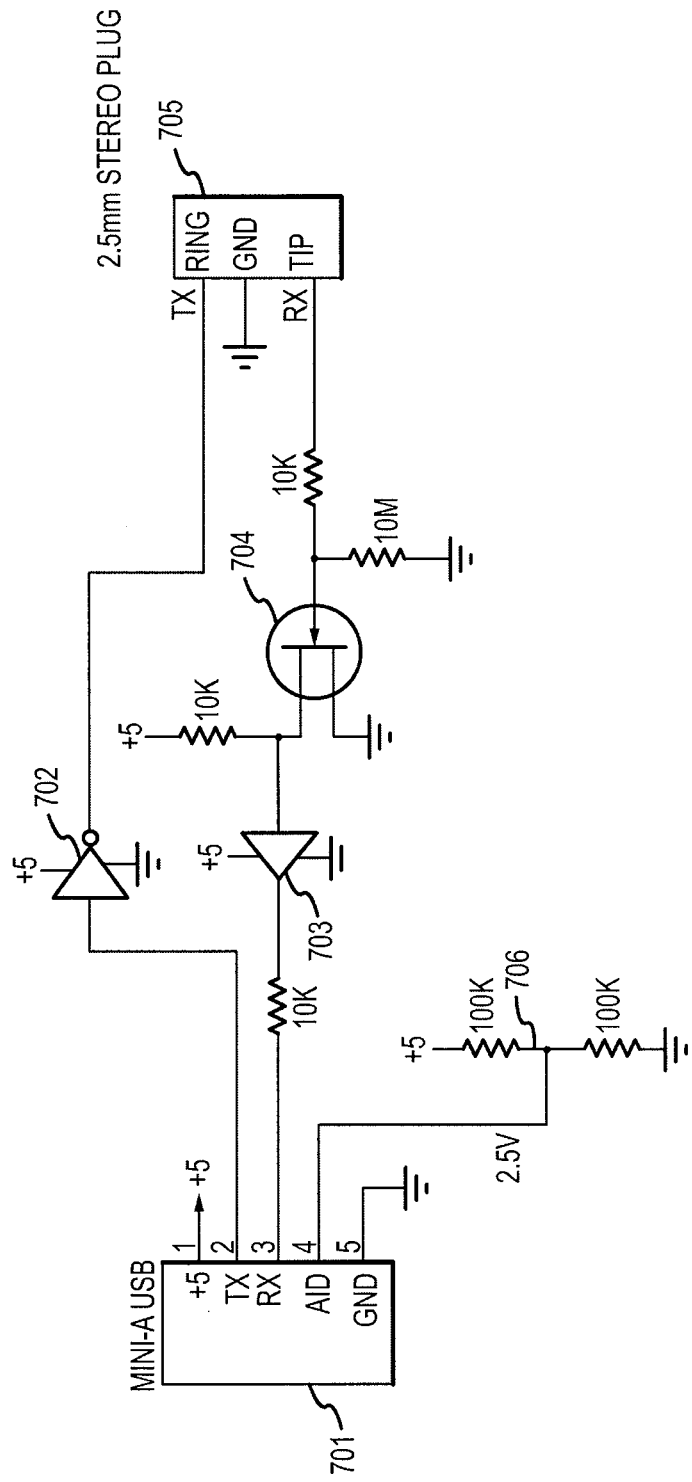
FIG. 7 is a circuit diagram illustrating elements of an alternate exemplary embodiment of a smart cable with ID capability.

FIG. 7 depicts a circuit diagram for another adapter 240 according to various aspects of the present invention. In this exemplary embodiment, USB connector 701 interfaces with USB port 502 shown in FIGS. 5A and 5B. Inverter 702 inverts the logic level of the Tx signal provided by the microcontroller 501 through the USB connector 701 to correspond to the voltage levels used by a medical device 250 connected to TRS connector 705. The Rx signal from a medical device 250 connected to the TRS connector 705 is provided to an N-channel JFET 704. In this exemplary circuit, when the Rx signal from the medical device 250 is marking (a −5.5 volt signal indicative of a logical "1") the JFET 704 is turned off, causing a 5-volt signal to be provided through buffer 703 and to the Rx lead of the UART on the microcontroller 501. Alternatively, when the Rx signal from the medical device 250 is spacing (a 6-volt signal indicative of a logical "0") the JFET 704 is turned on, causing ground to be provided through buffer 703 and to the Rx lead of the UART on the microcontroller 501, 520. The present invention can be configured to operate in conjunction with any other combination of voltages between the microcontroller 501, 520 and the TRS connector 705.

Device Interface 242

The device interface 242 communicates with one or more medical devices 250. The device interface 242 can also communicate with any other system, device or entity. The device interface 242 may include any number and combination of hardware and/or software components. The device interface 242 can communicate with medical devices through an adapter 240, as shown in FIG. 2A. In this exemplary embodiment, the device interface 242 connects to an external adapter 240 configured to couple with one or more medical devices 250. In this way, adapters 240 that allow connections to different medical devices can be used interchangeably with the same medical data interchange device 200. In another exemplary embodiment, referring to FIG. 2B, the device interface 242 is integrated with the adapter 240.

Any number of adapter modules 240 may be used in conjunction with the present invention, for example to communicate with multiple medical devices 250 using different wired connections and/or communication protocols. The present invention may be used in conjunction with any wired connection and communication protocol to communicate with one or more medical devices. For example, the medical data interchange device 200 may be configured to communicate with one or more medical devices using, without limitation: tip and sleeve (TS), tip, ring, and sleeve (TRS), and tip, ring, ring, and sleeve (TRRS) connections; serial peripheral interface bus (SPI) connections; universal serial bus (USB) connections; RS-232 serial connections; Ethernet connections, optical fiber connections, and Firewire connections.

In the exemplary embodiments depicted in FIGS. 2A and 2B, the device interface 242 and/or adapter 240 can be configured (e.g. through a software program residing in memory 220 and executed by processor 210) to detect and switch to different communication protocols and/or different wired connections to one or more medical devices 250 or other devices (such as the computer system 280), thus providing interoperability between types and manufacturers of a wide variety of devices. The auxiliary communication system 244 depicted in FIG. 2B may similarly be configured.

The medical data interchange device 200 can be configured to automatically request data from one or more medical devices 250 at predetermined times using the device interface 242. Any appropriate date or time setting may be used. The data interchange device 200, medical device 250, or any other device operating in conjunction with the present invention can be configured to automatically request and/or transmit data in any suitable manner. For example, the medical data interchange devices 200 depicted in FIGS. 2A and 2B can be configured through the device interface 242, the user interface 290, and/or from a command issued transmitted by an intermediary device 260 through the data relay transceiver 230. Additionally the medical data interchange device depicted in FIG. 2B can be configured through the auxiliary communication system 244. In the case of a command received through the data relay transceiver 230, the command can be generated by any suitable entity, such as from a medical data server 260 or a user of the intermediary device.

The automatic requesting/transmission of data by a device operating in conjunction with the present invention may be subject to any suitable conditions or rules that dictate whether the data is in fact requested/transmitted. For example, a medical data interchange device 200 programmed to request data from a medical device 250 at a set time may first check to verify that the medical device is within range, that the translator 200 has sufficient battery reserves to send the request and receive the data, whether the translator 200 has sufficient space in the memory 220 to store the data, and/or whether any other suitable condition is met.

Auxiliary Communication System 244

The medical data interchange device 200 depicted in FIG. 2B includes an auxiliary communication system 244 for communicating with additional systems and devices. For example, the auxiliary communication system 244 may be used to communicate with an external personal computer system 280 to upload software to the data interchange device 200, store data, provide or update encryption keys, perform diagnostics, and other appropriate purposes. The auxiliary communication system 244 can be a separate device, system, and/or component, or may be integrated with another component, such as the device interface 242. For example, in one embodiment of the present invention, the device interface 242 includes a USB port for communicating with any device capable of communicating through a USB connection. This allows the medical data interchange device 200 to communicate instructions, software upgrades, medical data, and other information with computing devices, memory storage devices (such as portable USB memory drives), as well as medical devices. The same device interface 242 can thus be used to receive medical data from a medical device 250 as well as to download reports that include the medical data. In one embodiment, medical data received by the medical data interchange device 200 may be formatted by the processor 210 into a ubiquitous data format such as Portable Document Format (PDF), and subsequently transferred to an external device such as a computer system 280 through the auxiliary communication system 244.

The medical data interchange device 200 or other system operating in conjunction with the present invention can include any suitable circuit, component, device, and system for communicating with any other device. The auxiliary communication system 244 can be used to transfer data to and from the medical data interchange device 200, as well as for an external computer system 280 to configure or program software and hardware in the data interchange device 200. In one embodiment of the present invention, for example, a user operating computer system 280 connected to medical data interchange device 200 through the Internet can configure settings for the device interface 242, adapter 240, data relay transceiver 230, and user interface 290. The computer system 280 can also download data received by the data interchange device 200 from one or more medical devices 250. Additionally, the computer system 280 may communicate with the medical devices 250 real-time through the medical device transceiver 240, such as to monitor or control one or more medical devices 250 in real-time.

User Interface 290

The medical device 250, medical data interchange device 200, intermediary device 260, or other device operating in conjunction with the present invention may include a user interface. Referring to FIGS. 2A and 2B, an exemplary user interface 290 of a medical data interchange device 200 in accordance with aspects of the present invention includes an input device 292 and an output device 294. The input device 292 receives commands, data, and other suitable input from a user. The output device 294 provides the user with data, alerts, and other suitable information from the medical data interchange device 200.

Any number of input devices may be included in a user interface for one or more devices in the present invention. In one embodiment of the present invention, for example, the user interface 290 includes a touch pad, a touch screen, or an alphanumeric keypad to allow a user to enter instructions and data into the medical data interchange device 200. One or more buttons on the keypad or touch screen can be programmed or configured to perform specific functions, such as to request data from one or more medical devices. The user interface 290 can also include one or more multi-function switches, keys, or buttons that each allows a user to perform multiple functions.

The user interface may also include a microphone to allow the user to provide such information to the medical data interchange device 200 verbally. In this exemplary embodiment, the medical data interchange device 200 also includes speech recognition software to process verbal input through the user interface 290. The ability of the medical data interchange device to recognize speech from a patient can be particularly useful for users/patients who have vision problems, arthritis, or other impairments that would inhibit them from using a keypad or other input device. A microphone can be used in conjunction with audible (e.g. through sound waves perceivable by the human ear) data provided through a speaker, as discussed below, to allow a user to interact with any device operating in conjunction with the present invention in a completely auditory manner. In one nonlimiting example, audible input could also be sensed and analyzed by the medical data interchange device 200 that a patient has uttered a command, such as the command to turn on. Bidirectional audible communication, in addition to aiding impaired patients, allows users to operate devices in the present invention in a hands-free manner which can increase the speed, ease, and efficiency in which a device (such as the medical data interchange device 200) can be utilized.

Devices operating in conjunction with the present invention may include any number of suitable output devices. Referring to the exemplary medical data interchange device circuits depicted in FIGS. 5A and 5B, a user interface 290 including two lights 511 (LED1 and LED2) may be used to indicate the status of the medical data interchange device 200 to the user, as well as other pertinent information. For example, a flashing LED can be used to indicate when data from a medical device is in the process of being transferred, while a solid LED can indicate the transfer of data is complete. The medical data interchange devices 200 depicted in FIGS. 5A and 5B also provide auditory output through speaker 515. The microcontroller 501, 520 retrieves audio samples, such as recorded speech, from the EEPROM 510 and provides output to DAC 512, which converts the digital signal from the microcontroller 501, 520 to an analog signal that can be output on the speaker 515. The analog signal is provided to an audio amplifier 514 that amplifies the signal. The gain of the amplifier 514 is set by the ratio of resistors 516 and 513.

Any other suitable user interface features may similarly be included in devices and systems operating in accordance with the present invention. In another exemplary embodiment, for example, the output device 294 includes a display screen to visually display information as well as a speaker (e.g. speaker 515 shown in FIGS. 5A and 5B) to provide auditory output. The output device 294 can include multiple transducers such as audio speakers or piezoelectric elements, amplifiers, and other appropriate devices and systems to provide the auditory output. The medical data interchange device 200 may be configured to provide words, phrases, tones, recorded music, or any other type of auditory output to a user.

Any type of information may be communicated through the user interface 290, such as the biological, biometric, or behavioral information for one or more patients. The user interface can provide/receive any other suitable information, such as environmental information and/or diagnostic data for a medical device, a battery charge level, a temperature, a barometric pressure, a code relating to an accessory for the medical device, a biometric access measurement, a data validity measurement, an elapsed time since a previous reading by the medical device, a test result parameter, a signal-to-noise parameter, and a quality of service (QoS), and combinations thereof.

Information provided or received by the user interface 290 may be in any appropriate format. For example, a user interface that communicates information to a user in an auditory format may first provide a data header followed by a data value to identify the data to the user. Similarly, an output device 294 providing information to a user visually may provide a series of measurements in the form of a spreadsheet with headers indicating the source of the measurements. The output device 294 can also provide information in any number of desired languages, regardless of whether the information is provided audibly or visually.

Various features of the user interface can be implemented in hardware, software, or a combination of the two. In the medical data interchange devices 200 depicted in FIGS. 2A and 2B, for example, the user interface 290 includes voice interface software stored in the memory 220, including tables of recorded words and phrases. When executed by the processor 210, the voice interface software plays the appropriate recorded words and phrases (such as enunciating the medical data) through a speaker such as one included in the output device 294 to provide information to the user. The voice interface software, like any software operating on the medical data interchange device 200, can be downloaded and configured through the auxiliary communication system 244 or device interface 242. As discussed previously, any software program on any device operating in accordance with the present invention can be programmed or configured through any other suitable interface. In the medical data interchange device 200, for example, the voice interface software could also be downloaded and configured through the data relay transceiver 230 in response from a command from a medical data server 270 and/or intermediary device 260, as well as from input from the user through the user interface 290. Accordingly, the voice interface software can be configured to include words and phrases in any number of different languages, and can be updated with new words and phrases as desired, such as to accommodate a new medical device 250 operating with the medical data interchange device 200. Non-verbal sounds, such as melodies and tones, can also be stored and used by the user interface 294 to provide alerts, indicators, and other information to the user.

The user interface can also provide/receive information to a user in a machine-readable format. In one exemplary embodiment of the present invention, for example, the user interface 290 of a medical data interchange device 200 includes a fixed or retractable USB port to communicate with a thumb drive, memory stick, portable hard drive, an external computer system, or other USB-compatible device. This allows doctors and other healthcare providers to directly access the medical data interchange device 200 directly, without having to retrieve the data from a medical data server. In this exemplary embodiment, the medical data interchange device 200 can be configured to send, receive, and process machine-readable data can in any standard format (such as a MS Word document, Adobe PDF file, ASCII text file, JPEG, or other standard format) as well as any proprietary format. Machine-readable data to or from the user interface may also be encrypted to protect the data from unintended recipients and/or improper use. In an alternate embodiment, a user must enter a passcode to enable use of the USB port, and optionally, after a period of time of non-use, the USB port is automatically disabled. Any other user interface feature may be utilized to allow a human or non-human user to interact with one or more devices operating in conjunction with the present invention.

Power Saving Features

A medical data interchange device, intermediary device, medical device, or other system operating in accordance with aspects of the present invention may include any other suitable features, components, and/or systems. For example, the data interchange device 200 or other device may be configured to preserve the life of its battery by shutting off or going into a low-power mode when it, and/or the medical device it monitors, experiences a predetermined period of non-use, or a change in a measured parameter such as indication that a case holding the translator 200 has been actuated to a closed position. Such devices can also be configured to become active in response to any suitable event, such as receiving a signal from a device (such as a sensor).

Figure 8:
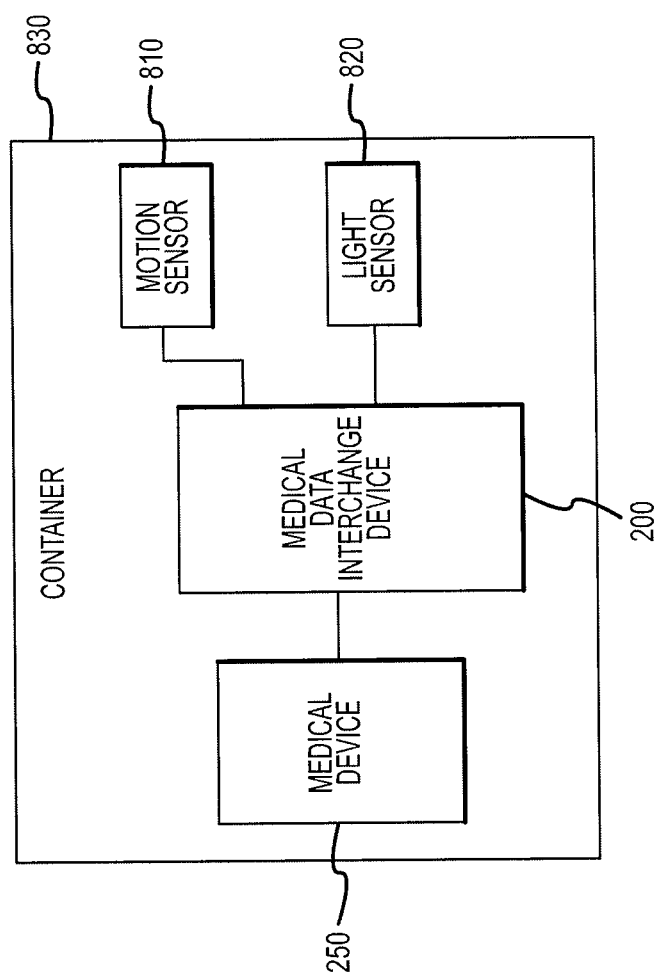
FIG. 8 is a block diagram depicting a container including light and motion sensors for activating a medical data interchange device in accordance with various aspects of the present invention.

In one non-limiting embodiment of the present invention, referring now to FIG. 8, a medical data interchange device 200 communicates with a motion sensor 810 and a light sensor 820 to determine when a container 830 holding the data interchange device 200 and the medical device 250 it monitors is open or closed. In this exemplary embodiment, the data interchange device 200 can preserve the life of its battery by shutting off or going into a low-power mode when the container 830 is closed and, therefore, the medical device 250 held in the container 830, is not in use. Any type of motion sensor can be used in accordance with the present invention, such as an accelerometer, tilt switch, or other device that generates a signal in response to movement. Similarly, any type of light sensor may be used in conjunction with the present invention. The light sensor can be used to detect the amount of light entering a container 830 holding the medical device, medical data interchange device, or other device to activate the device when the sensed amount of light exceeds a predetermined threshold, or if an increase in the amount of incident light exceeds a predetermined threshold. In an alternate embodiment, a microphone may receive audible signals that are analyzed by the medical data interchange device 200 to indicate a command has been uttered that indicates that the medical data interchange device 200 should be shut down or activated from a quiescent or low-power state.

A sensor may be integrated into the medical data interchange device 200, or operate externally to the data interchange device 200, communicating with the data interchange device 200 wirelessly or through a wired connection. For example, in the exemplary embodiment depicted in FIG. 8, the motion sensor 810 and light sensor 820 are integrated into the interior of the container 830 and communicate with a medical data interchange device 200 contained within to indicate when the container 830 is actuated from a closed position to an open position.

Security Measures

Systems and devices operating in accordance with aspects of the present invention may implement one or more security measures to protect data, restrict access, or provide any other desired security feature. For example, any device operating in conjunction with the present invention may encrypt transmitted data and/or protect data stored within the device itself. Such security measures may be implemented using hardware, software, or a combination thereof. Any method of data encryption or protection may be utilized in conjunction with the present invention, such as public/private keyed encryption systems, data scrambling methods, hardware and software firewalls, tamper-resistant or tamper-responsive memory storage devices or any other method or technique for protecting data. Similarly, passwords, biometrics, access cards or other hardware, or any other system, device, and/or method may be employed to restrict access to any device operating in conjunction with the present invention.

Exemplary Method Using Wireless Communication

Figure 10:
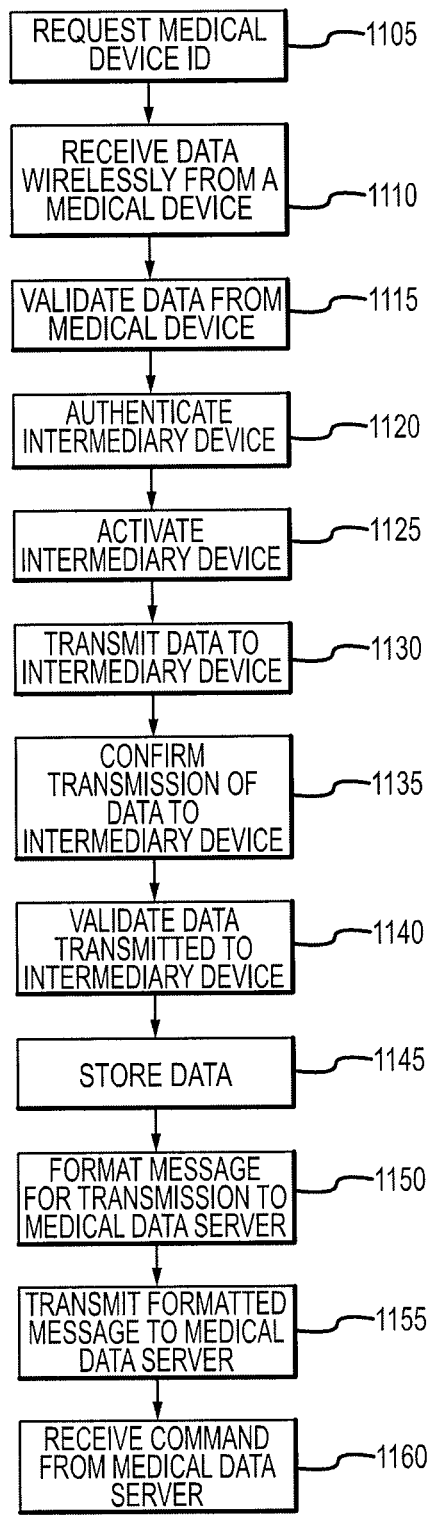
FIG. 10 is a flow diagram depicting an exemplary process for medical device monitoring according to various aspects of the present invention.

An exemplary method according to an aspect of the present invention is depicted in FIG. 10. In this method, an identifier is requested from a medical device (1105), and data from the medical device is received (1110) and validated (1115). An intermediary device such as a mobile phone or personal digital assistant is authenticated (1120) and activated (1125). The data is transmitted by the medical device to the intermediary device (1130) and the transmission to the intermediary device is confirmed (1135). The data is stored (1140) in the intermediate device. A message is formatted (1145) and transmitted to a medical data server (1150). Optionally, a command can be received from the medical data server (1155) and optionally relayed from the intermediary device. Any combination and/or subset of the elements of the method depicted in FIG. 10 may be practiced in any suitable order and in conjunction with any system, device, and/or process. The method shown in FIG. 10 can be implemented in any suitable manner, such as through software operating on one or more computer systems. Exemplary systems for performing elements of the method shown in FIG. 10 are discussed later in this description.

Request Medical Device ID

In the exemplary process according to aspects of the present invention depicted in FIG. 10, an identifier is requested from a medical device providing the data to be monitored (1105). Any suitable identifier may be provided, such as the serial number of the medical device or a numeric, alphabetic, alphanumeric, or other identifier. The medical device identifier can be used to determine whether the correct medical device is being monitored. The medical device identifier can also be used to determine the manufacturer, model, type, characteristics, or other information pertinent to the medical device and/or the patient(s) it monitors. The medical device identifier may be received passively, such as from a medical device that automatically includes its identifier as part of its telemetry broadcast. Alternatively, the medical device can be polled to request the medical device identifier. The medical device identifier need not be requested from the medical device each time the medical device is being monitored. For example, the medical device identifier may be stored in a storage medium for future reference.

Receive Data Wirelessly from a Medical Device

In the exemplary method shown in FIG. 10, data is received wirelessly from the medical device (1110). Accordingly, any system implementing the method of FIG. 10 does not need to be physically connected to the medical device to receive the data. Patients monitored by medical devices are thus able to lead active lifestyles without being forced to remain close to the system receiving the data from the medical device. Data can be received from any medical device, such as a blood glucose meter, a pacemaker, a blood pressure monitor, an insulin pump, a pulse oximeter, a holter monitor, an electrocardiograph, an electroencephalograph, a blood alcohol monitor, an alcohol breathalyzer, an alcohol ignition interlock, a respiration monitor, an accelerometer, a skin galvanometer, a thermometer, a patient geolocation device, a scale, an intravenous flow regulator, patient height measuring device, a biochip assay device, a sphygmomanometer, a hazardous chemical agent monitor; an ionizing radiation sensor; a monitor for biological agents, a loop recorder, a spirometer, an event monitor, a prothrombin time (PT) monitor, an international normalized ratio (INR) monitor, a tremor sensor, a defibrillator, or any other medical device. A medical device that includes a combination of different medical devices (such as those listed previously) may be monitored in accordance with the present invention. The medical device can be partially or completely implanted in a patient, such as in the case of a pacemaker. The medical device may also be located externally to a patient. The medical device may be connected to a patient (for example, through one or more electrodes), or operate independent of any coupling to a patient, such as a scale. The medical device may also operate in conjunction with a temporary interfacing with a patient, such as the case of the cuff of a blood pressure monitor encompassing the arm of a patient to take a reading.

Figure 11:
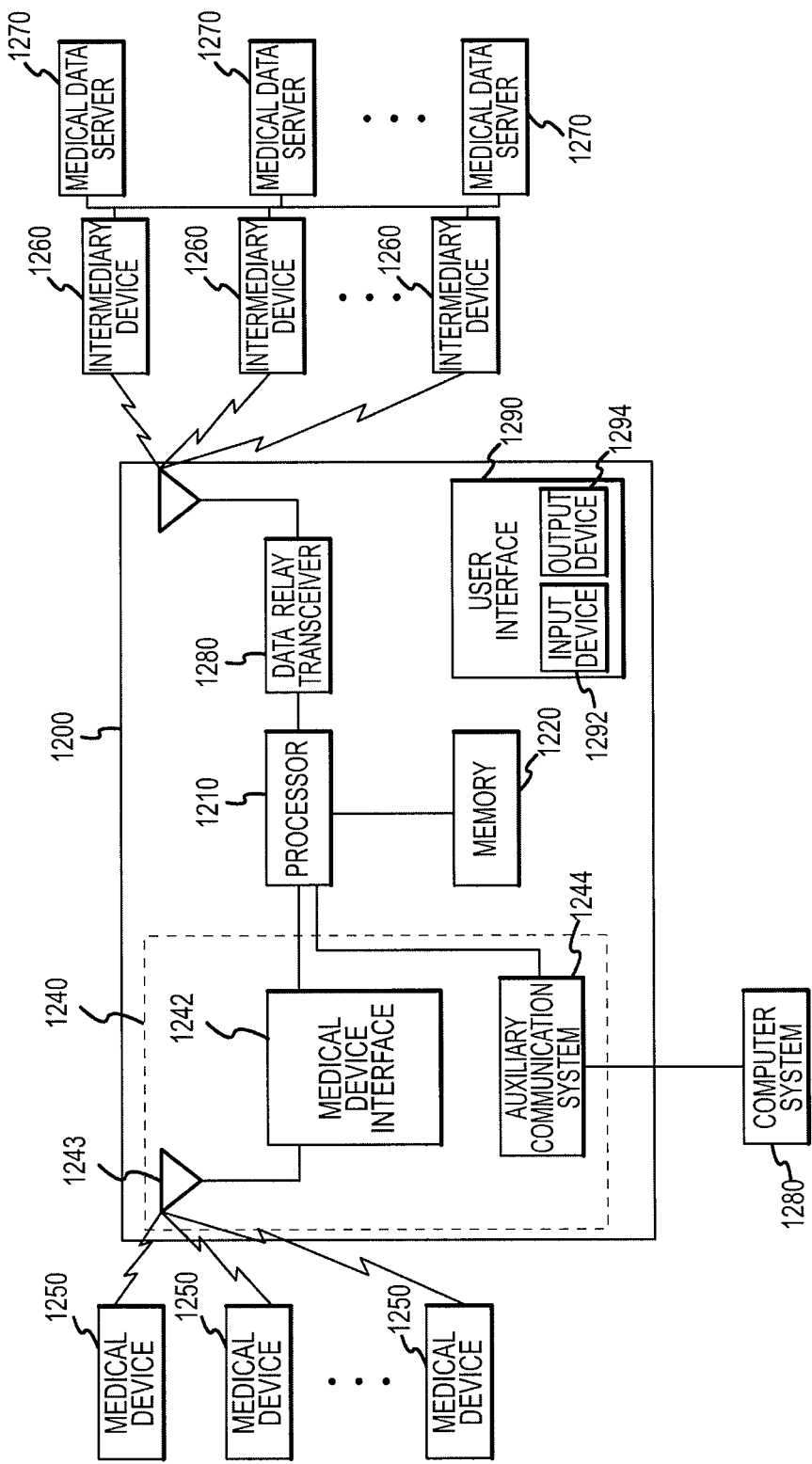
FIG. 11 is a block diagram depicting an exemplary system for medical device monitoring according to various aspects of the present invention.

The medical device data can be received by any person, system, device, or other suitable recipient. The exemplary method in FIG. 10 may be practiced manually by a human being, automatically by a device, or a combination of the two. An exemplary device for performing the method depicted in FIG. 10 is depicted in FIG. 11 and is discussed in detail below.

Data can be received directly from a medical device. For example, some medical devices such as pacemakers and other devices implanted in a patient include wireless transmitters to wirelessly broadcast data. A medical device can also provide data wirelessly using another device. In one embodiment of the present invention, for example, a medical device provides data through a serial port (a wired connection) to a computing device. The computing device is in turn connected to a wireless router. The data can thus be received wirelessly after being retransmitted from the wireless router.

The medical device may transmit on any frequency using any format and protocol. For example, various medical devices transmit data in the Wireless Medical Telemetry Service (WMTS) frequency bands. There are three WMTS frequency bands, including frequencies from 608 MHz to 614 MHz, 1395 MHz to 1400 MHz, and 1427 MHz to 1432 MHz. In another example, the medical device may transmit using the Medical Implant Communications Service (MICS) frequency band, including frequencies from 402 MHz to 405 MHz. In yet another example a medical device may transmit data in the 32 KHz to 175 KHz range.

The medical device data can be received from a plurality of different medical devices, where each medical device may perform any combination of functions. For example, data from a glucose meter, blood pressure monitor, and combination scale/height measuring device each transmitting data in different formats and on different frequencies may each be received in accordance with the present invention. In the case where a plurality of medical devices transmits data in response to a request for data, each device in the plurality of devices can be sent such a request separately. Alternatively, a plurality of medical devices automatically transmitting data on the same frequency, in the same format, and potentially at the same time (such as in the case of multiple devices of the same type and/or from the same manufacturer) can be received in accordance with the present invention by, for example, using a separate wireless receiver keyed to a unique identifier associated with each medical device. When data has been received from a plurality of medical devices, in one embodiment, a list of the medical devices may be displayed on a user interface, and optionally, the user may be prompted to select one, all, or none of the plurality medical devices, whose data is desired to be transmitted to the medical data server. The data for the selected set of medical devices is then relayed as described with alternate embodiments as described herein. Any other suitable method for receiving data from a plurality of medical devices may also be used in conjunction with the present invention.

Any type of data may be received from a medical device. For example, the data may include information regarding a patient, such as the patient's biological and biometric information, the patient's behaviors, results of analysis of physical patient parameters, and information regarding the patient's environment. For example, a medical device such as a glucose meter could provide data regarding a patient's current (or last measured) blood glucose level, the date and time the patient last used the glucose meter, and the current temperature or other environmental factors that might affect a glucose test. Other possible environmental parameters that may be included in the data received from a medical device include a battery charge level, a temperature, a barometric pressure, a code relating to an accessory for the medical device, a data validity measurement, an elapsed time since a previous reading by the medical device, a test result parameter, a signal-to-noise parameter, and a quality of service (QoS), and combinations thereof. Data received from a medical device may also include any other suitable information, such as diagnostic information regarding the medical device.

The medical device data may provide data relating to a single patient or multiple patients. In the case where a single medical device provides data regarding multiple patients, the data can be identified with an individual patient either in the data received by medical device (such as by using a patient identifier) or through processing in accordance with the present invention.

The medical device can provide the data in any format. Different medical devices from different manufacturers often use different formats for providing data. For example, data from a glucose meter may be provided in a series of fixed-length data records followed by a terminator indicator (such as a null or other predefined character) and/or a checksum for validating the data. Any type of data may be provided. In the case of a glucose meter, the data may include one or more readings of a patient's blood glucose level and the date and time each reading was taken. The medical device identifier discussed previously may be used to determine a specific data format used by a medical device. Alternatively, a data format may be specified by a user or selected by analyzing the format of the data received and comparing it to a set of known medical device data formats.

Validate Data

In the exemplary process shown in FIG. 10, the data from the medical device is validated (1115). The data from the medical device can be validated in any suitable manner to achieve any result. For example, the data from the medical device may be validated to ensure it was transmitted properly and completely. The medical device data may also be validated to ensure it was provided from a specific medical device or particular type of medical device. The data may also be validated to ensure that fields in the data correspond to predetermined values and/or are within certain thresholds or tolerances. Any number, code, value or identifier can be used in conjunction with validating the medical device data. For example, the data can be validated by analyzing a medical device serial number, a medical device identifier, a patient identifier, one or more parity bits, a cyclic redundancy checking code, an error correction code, and/or any other suitable feature.

Authenticate Intermediary Device

In the exemplary method depicted in FIG. 10, an intermediary device receiving the data is authenticated (1120). In the context of the present invention, the intermediary device includes any type of system or device capable of receiving the medical device data in any manner. Such intermediate devices may include, for example, personal computers, laptops, personal digital assistants, and mobile computing devices. The intermediary device may process the data in any manner, and can transmit some or all of the data to another recipient, such as a medical data server. For example, but not by way of limitation, the intermediary device may include a personal computer or a mobile computing device, such as a laptop computer, a mobile wireless telephone, or a personal digital assistant (PDA). In an exemplary embodiment of the present invention, the intermediate device further includes software for receiving the medical device data, formatting a message based on the data, and transmitting the formatted message to a medical data server. Such software can operate on any suitable mobile computing device and with any computer operating system.

The intermediary device may also include any number of other systems and devices suitable for receiving data from the medical device, processing the data, and/or transmitting the data to a medical data server. Further discussion regarding exemplary embodiments of intermediary devices is presented later in this description.

The intermediary device can receive the data directly from the medical device, or from one or more other devices. In one exemplary embodiment of the present invention, the intermediary device comprises a mobile computing device including one or more wireless transceivers and is configured to receive data from the medical device directly. In another exemplary embodiment of the present invention, the medical device transmits the data to a first device, which in turn transmits the medical device data to the intermediary device (wirelessly or through a wired connection).

The intermediary device may be authenticated to achieve any result. For example, the intermediary device may be authenticated to restrict transmission of the data from the medical device to intermediary devices operating as part of the present invention. Authentication can also prevent sensitive medical data from being broadcast and viewed by unintended recipients. The intermediary device may also be authenticated to verify the intermediary device is able to receive, process, and/or transmit the medical device data to a medical data server. During authentication, the authenticated device or devices may also be remotely commanded, and such commands may include steps that configure devices to interoperate with components of the present invention. For example, but not by way of limitation, such steps may include the downloading of software applications, applets, embedded operating code, and/or data.

The intermediary device can be authenticated in any manner. For example, an intermediary device can be authenticated to receive data from one or more medical devices using an authorization code. The authorization code can be any number, code, value or identifier to allow the intermediary device to be identified as a valid recipient of the data from the medical device. In one exemplary embodiment of the present invention, an intermediary device stores an authorization code and broadcasts the authorization code in response to a request for authorization. Unless the authorization code matches a code stored by the transmitter of the medical device data (such as the medical device itself or another transmission device), the medical device data is not transmitted to the intermediary device. Transmission of the medical device data to the intermediary device need not necessarily be predicated upon successful authentication of the intermediary device, however.

In another exemplary embodiment of the present invention, an intermediary device receiving the medical device data using a wireless network protocol (such as Bluetooth) is authenticated based on whether the intermediary device advertises one or more services. In this context, advertised services reflect functions, utilities, and processes the intermediary device is capable of performing. The intermediary device broadcasts indicators of this functionality, thus "advertising" them to other systems and devices. In the present exemplary embodiment of the invention, unless the intermediary device advertises a service that is identifiable with the operation of the present invention (i.e. a process capable of broadcasting the medical device data to a medical data server, for example), the intermediary device is not authenticated and thus the medical device data is not transmitted to the intermediary device.

Activate Intermediary Device

In the exemplary process depicted in FIG. 10, the intermediary device can be activated (1125) prior to transmitting the medical device data to the intermediary device. Many devices, particularly mobile computing devices running on batteries, employ power-saving features to conserve battery life when not in use. In the case where an intermediary device is in a power-saving or standby mode, it may be necessary to activate the intermediary device before it can receive the medical device data. The intermediary device can be activated in any suitable manner. For example, a signal configured to activate the device may be transmitted to prepare the intermediary device to receive the medical device data.

Transmit Data to Intermediary Device

The medical device data is transmitted to the intermediary device (1130). The data can be transmitted in any suitable manner. In one exemplary embodiment of the present invention, the medical device data is transmitted to the intermediary device using a wired connection, such as an RS-232 serial cable, USB connector, Firewire connector, or other suitable wired connection. The medical device data can also be transmitted to the intermediary device wirelessly using a wireless transmitter. Any suitable method of wireless communication can be used to transmit the medical device data, such as a Bluetooth connection, infrared radiation, Zigbee protocol, Wibree protocol, IEEE 802.15 protocol, IEEE 802.11 protocol, IEEE 802.16 protocol, and/or ultra-wideband (UWB) protocol. If desired, the medical device data could be transmitted to the intermediary device using both a wired and wireless connection, such as to provide a redundant means of communication, for example.

Any amount of medical device data can be transmitted to the intermediary device in any manner. For example, data from the medical device can be transmitted to the intermediary device in real-time, or medical device data can be stored (such as in a memory storage device) for a period of time before being transmitted to the intermediary device. In some cases, for example, it may be more efficient to transmit blocks of medical device data at once rather than initiating communication with an intermediary device each time data is available from the medical device. In other cases, the intermediary device may be out of range or otherwise unavailable to receive the medical device data. The medical device data can also be stored for any desired length of time, and/or until a particular event occurs. For example, the medical device data could be stored until it is verified that the intermediary device and/or the medical data server have received the data, allowing the data to be retransmitted if necessary.

The medical device data can be transmitted to the intermediary device in any format. For example, the data from the medical device can be transmitted to the intermediary device exactly as it is transmitted from the medical device. This would be the case in embodiments of the present invention where the medical device itself is transmitting the data directly to the intermediary device. Alternatively, in embodiments of the present invention where the data is being received from the medical device and then retransmitted to the intermediary device, the medical device data can be reformatted, modified, combined with other data, or processed in any other suitable manner before being transmitted to the intermediary device. For example, the medical device data can be encrypted prior to transmission to the intermediary device, and this encryption may occur at any stage, for instance in the medical device itself or at a stage after being transmitted by the medical device. In cases where the medical device data is being combined with other data and transmitted to the intermediary device, all of the data may be encrypted or simply the medical device data itself. In an alternate embodiment, a digest of the medical data may be encrypted, to digitally "sign" the data contents to verify its authenticity. For example, but not by way of limitation, this digest may be produced by providing the received medical data to a hashing algorithm such as the MD5 or SHA-1 Secure Hashing Algorithm as specified in National Institute of Standards and Technology Federal Information Processing Standard Publication Number 180-1.

Asymmetric encryption algorithms and techniques are well known in the art. See, for example, RSA & Public Key Cryptography, by Richard A. Mollin, CRC Press, 2002, and U.S. Pat. No. 4,405,829, issued Sep. 20, 1983, the disclosures of which are fully incorporated by reference herein for all purposes. In an illustrative example, if two parties (for example, "Alice" and "Bob") wish to communicate securely using public key cryptography, each party begins by generating a unique key pair, where one of the keys is a private key that is kept in confidence by that party, and the other key is a public key that may be publicly distributed, published only to a message recipient, or made available through a public key infrastructure. The key generation step need be done by a party only once, provided that the party's private key does not become compromised or known by another party. If Alice wants to send a message confidentially to Bob, she may use Bob's public key to encrypt the message, and once sent, only Bob can decrypt and view the message using Bob's private key. But if Alice also wanted Bob to have assurance that the message was in fact coming from her, she could further encrypt the message with her private key before sending, then when Bob's private key and Alice's public key are used to decrypt the message, Bob knows for certain that he was the intended recipient and that Alice was the one who originated the message, and Alice knows that only Bob will be able to decrypt and read her message.

Asymmetric cryptography may be utilized to enhance security of certain implementations of the present invention. In an alternate embodiment, data transmitted by a medical device 1250 is encrypted with a private key of the medical device user (or optionally with the private key of a health care provider that is operating the medical device), or with a public key of the intended recipient system such as the medical data server 1270, or with both keys. The private and/or public keys may be delivered to the medical data translator 1200 through a wired or wireless connection, allowing the translator 1200 to be configured for secure operation. In one embodiment, the system or medical data server 1270 may request that the public key of the medical device be forwarded to enable decryption of any medical information encoded with the user's private key. In this manner, the data may be authenticated as coming from the actual patient that is desired to be monitored, and optionally, the patient may also be assured that only the intended recipient system or medical device server 1270 is capable of decrypting and gaining access to the patient's medical device data.

In alternate embodiment, encrypted or unencrypted data can be transmitted through an encrypted transmission protocol, such as the wireless encryption protocols (WEP, WPA and WPA2) associated with the IEEE 802.11 wireless protocols. Any number of other encryption methods can be used to encrypt the medical device data in conjunction with the present invention. The intermediary device may decrypt the medical device data, to allow processing of the data for example. Alternatively, to protect the data from unauthorized viewing, an intermediary device could simply retransmit the encrypted data to the medical data server.

Confirm Transmission of Data to Intermediary Device

The transmission of the medical device data can be confirmed (1135) to verify the transmission was successful. The transmission can be confirmed in any suitable manner. For example, the intermediary device can transmit an acknowledgement once the transmission is received, otherwise the transmission can be rebroadcast.

Validate Data Transmitted to Intermediary Device

In the exemplary process shown in FIG. 10, the data transmitted to the intermediary device is validated (1115). The data from the medical device can be validated in any suitable manner to achieve any result. For example, the data from the medical device may be validated to ensure it was transmitted properly and completely. The medical device data may also be validated to ensure it was provided from a specific medical device or particular type of medical device. The data may also be validated to ensure that fields in the data correspond to predetermined values and/or are within certain thresholds or tolerances. Any number, code, value or identifier can be used in conjunction with validating the medical device data. For example, the data can be validated by analyzing a medical device serial number, a medical device identifier, a patient identifier, one or more parity bits, a cyclic redundancy checking code, an error correction code, and/or any other suitable feature.

Store Data

The intermediary device may store the medical device data (1145). The intermediary device may store the data in any suitable manner, such as by using a memory storage device. Any portion or amount of medical device data (or other forms of information) received or generated by the intermediary device may be stored for any length of time. The data may be stored for a predefined period of time and/or until an event occurs. For example, in one embodiment of the present invention the data is stored by the intermediary device until the data has been transmitted to the medical data server. In another embodiment, data is stored by the intermediary device until a predetermined data transmission record size has been reached, so as to reduce communication charges that may accrue during transmission. In yet another embodiment, the intermediary device stores the data until an acknowledgment from the medical data server is received, where the acknowledgment indicates that the stored data has been received by the medical data server.

Format Message for Transmission to Medical Data Server

In the exemplary method according to an aspect of the present invention depicted in FIG. 10, a message is formatted for transmission to the medical data server. The message can originate from any system operating in conjunction with the present invention. For example, the message may be created by the intermediary device, a device transmitting the medical device data to the intermediary device, or the medical device itself. The message can include some or all of the medical device data, as well as any other information useful to the medical data server. Multiple messages can be formatted to include any desired amount of medical device data. For example, in the case of data from a glucose meter, multiple messages may be formatted to each include a single glucose reading, or a single message could be formatted to include the last ten glucose readings taken by the meter. The message can include any other desired data from any suitable source. For example, real-time data from a medical device may be included in a message along with previously-transmitted data from the stored by the intermediary device creating the message. The message (in whole or in part) may be encrypted to protect the contents of the message from unintended viewers and/or the privacy of the patient being monitored.

The message provides the medical device information to the medical data server in a format the medical data server can recognize and utilize. The message can thus be formatted to only include portions of the medical device data needed by the server and/or additional information about a patient, the medical device, and/or the treatment regimen. The message can be of desired format. For example, the message can be included in a file having a tokenized format such as standard ASCII text format, or any other suitable standardized file format, such as an MS Word document, MS Excel file, Adobe PDF file, or binary picture file (JPEG, bitmap, etc.). The data within such a file can be ordered in any manner and have any suitable delimiters, notations, or other features. For example, a list of multiple glucose level readings in a text file message could be provided chronologically by when the readings were taken, with comma or tab delimiters to denote the start and end of each reading. The message may also have a unique and/or propriety format.

The format of the message can also be based on the method by which the message is transmitted to the medical data server. For example, where the message is transmitted to the medical data server using a wireless mobile telephone such as a cellular phone, the message can be formatted as an SMS text message. Similarly, the message may be formatted as an XML record, email, and/or facsimile. The message can include multiple formats and/or multiple messages may be formatted having different formats for transmission in a variety of methods or to a variety of recipient medical data servers.

Transmit Formatted Message to Medical Data Server

The message is transmitted to a medical data server (1155) to allow the medical device data to be analyzed and processed. The message can be transmitted to a single medical data server, or to a plurality of medical data servers. The medical data server can be any suitable recipient of the medical device data. For example, the medical data server can be a computer system or other device as well as a human recipient (such as a doctor, nurse, or other healthcare provider).

The message can be transmitted to the medical data server in any suitable manner. For example, the message can be transmitted to the medical data server through a wired connection, such as a telephone line, fiber optic cable, and/or coaxial cable. The message may also be transmitted wirelessly using any suitable wireless system, such as a wireless mobile telephony network, General Packet Radio Service (GPRS) network, wireless Local Area Network (WLAN), Global System for Mobile Communications (GSM) network, Personal Communication Service (PCS) network, Advanced Mobile Phone System (AMPS) network, and/or a satellite communication network. The message may be transmitted using any suitable combination of multiple wired and wireless communication methods. The transmission method selected to transmit the message to the medical data server can be chosen according to any desired criteria. For example, one or more transmission methods can be selected from a plurality of possible transmission methods to send the message based on each method's cost, time required to transmit, reliability, security, or any other suitable factor.

Receive Command from Medical Data Server

In addition to receiving the medical device data, the medical data server can transmit a command (1160). The command can be received by the intermediary device, the medical device, and/or or any other suitable recipient. Any number of commands of any type may be transmitted by the medical data server. The command can be transmitted using the same variety of wired and wireless methods discussed previously for the transmittal of the formatted message. The command need not be transmitted using the same communication method with which the formatted messages are transmitted to the medical data server.

In one embodiment of the present invention, for example, the medical data server issues a command to reconfigure a software application operating on the intermediary device. In another embodiment, the medical data server issues one or more commands to control the functionality of the medical device. In yet another embodiment, the medical data server issues one or more commands to request that a public encryption key corresponding to the patient using a medical device be forwarded to the medical data server, or that a device associated with the present invention receive a public encryption key corresponding to an intended recipient such as a particular health care service provider or other known destination such as the medical data server.

The commands need not be sent directly to a device they are intended to control. For example, a command could be transmitted to an intermediary device, which in turn retransmits it (unmodified) to the medical device to be controlled. Alternatively, the intermediary device could receive a command from the medical server, analyze it, and then transmit an appropriately formatted command tailored to the specific medical device to be controlled. In this manner, the medical data server need not be able to generate a command for each and every specific device it wishes to control, it can send a command appropriate to a class of devices (i.e. glucose meters) and the intermediary device will appropriately translate the command to control the medical device. The commands from the medical data server can initiate/run diagnostic programs, download data, request the patient's public encryption key, download the intended recipient's public encryption key, and perform any other suitable function on the intermediary device, medical device, or other devices operating in conjunction with systems and methods of the present invention.

A command from a medical data server can be in any appropriate format and may include any suitable information. For example, a command may include data received from one medical device 250 to be delivered to another medical device 250 through the medical data translator 1200. In this manner, a variety of medical devices can share data whether they are in communication with the medical data translator 1200 or not.

A command can also originate from an intermediary device. For example, a command to program or reconfigure one or more software programs on the medical data translator 1200 depicted in FIG. 11 can be provided by an intermediary device 1260 to the medical data translator 1200 through the data relay transceiver 1230. A command, as discussed above, may include multiple instructions, applets, or data elements to be processed, such as sections of executable code or interpretable scripts. Additionally, a user can program or configure a software program on any device operating in conjunction with the present invention through a suitable user interface, such as the user interface 1290 of medical data translator 1200.

In any system where commands can be sent remotely, security is always a concern, especially when a wireless implementation may provide an entry vector for an interloper to gain access to components, observe confidential patient data, and control health-sensitive components such as pacemakers and insulin pumps. In any digital data network, it is also possible that commands intended for one recipient may be misrouted to a patient or health care provider that was not the intended recipient of the command. There are, however, a number of methods to provide for enhanced security in a remote command system while still allowing flexibility and minimal obtrusiveness.

In one embodiment, a command received by any of the components in FIG. 11 may be authenticated before the command is either acted upon by the destination component, or forwarded to another component in the system. Authentication may be directed to determining (1) whether the command came from a trusted or authorized source and (2) that the recipient is actually the intended recipient of the command. In one implementation, source command authentication is achieved by determining whether the origin of the command is a trusted component or server, and one way to accomplish this determination is analyzing whether a command is properly digitally signed by the originator, or some other authentication information is provided that assures the recipient component that the message or command is authentic and the recipient component is actually the intended recipient. In an alternate implementation, destination command authentication is accommodated by examining the contents of the message or an authorization code to determine the intended recipient, or alternatively decrypting the command or a portion of the command to verify the intended recipient.

In one embodiment, when commands are created by a command originator, the originator provides for a means to verify the authenticity and/or validity of the command by at least one of the following methods: (1) encrypting the command with a private key of the command originator; (2) generating a digest of the command (through a method such as a hashing algorithm discussed above) and optionally encrypting the hashed digest with the command originator's private key, or (3) utilizing a symmetric encryption scheme providing an authentication code (such as a cryptographically hashed password) that is compared to previously stored values. Then, when a system component receives the command along with any encrypted or cleartext certification data, the component may determine the command is valid by (1) attempting to decrypt an encrypted command message with the alleged originator's public key, (2) attempting to decrypt an encrypted digest with the alleged originator's public key, and comparing the result to a hashed value of the command, or (3) comparing a cryptographically hashed password for the alleged originator to known pre-stored values, and if a match is found, authorization is granted. As an additional step, if the command were optionally encrypted using the intended patient/provider's public key, then only the recipient is capable of decrypting the command, ensuring that only the truly intended patient's healthcare devices were being issued commands, and not an unintended third party. For example, in one embodiment, authenticating the command comprises decrypting at least part of the command using at least one of: a public key associated with the medical data server; a private key associated with a user of the medical device; and a private key associated with the medical device.

Authenticate User Access to Medical Data Server

In another embodiment, the method described in FIG. 10 may be used in conjunction with the authentication process described above for FIG. 9.

Exemplary System Using Wireless Communication

An exemplary system for use in conjunction with the present invention is depicted in FIG. 11. This system may be used in conjunction with the method described in FIG. 10, as well as with any subset or combination of the elements thereof. The system shown in FIG. 11 may also be used in conjunction with any other suitable embodiments of systems and methods for medical device monitoring according to an aspect of the present invention.

The exemplary system for medical device monitoring depicted in FIG. 11 includes a medical data translator 1200 that includes a processor 1210 coupled to a memory 1220. A data relay transceiver 230 wirelessly communicates with one or more intermediary devices 1260 via antenna 1232, which in turn communicates with one or more medical device servers 1270 through either a wired or wireless protocol. An adapter module 1240 communicates with one or more medical devices 1250 via antenna 1243. The adapter module 140 includes a medical device transceiver 1242 and an auxiliary communication system 1244, both in communication with the processor 1210. The auxiliary system 1244 may include any number of wired or wireless connections to one or more computer systems 1280, such as a universal serial bus (USB) connection, serial connection, parallel connection, Firewire connection, Ethernet connection, or any other suitable connection. The medical data translator 1200 may include any suitable power connection for powering the translator and/or for recharging an energy storage device such as a battery (not shown). The components of the medical data translator 1200 may receive electrical power from any other type of power supply The medical device transceiver is coupled to an antenna, 1243, which may establish unidirectional or bidirectional wireless communications with one or more of the medical devices 1250. The antenna 1243 may be the same antenna as antenna 1232, or one or more separate antennas. The antenna 1243 may be located internally or externally to the adapter module 1240, and may be configured in any suitable manner to operate with the medical data translator 1200. The functionality of the medical data translator 1200 can be implemented in any suitable manner, such as through the processor 1210 executing software instructions stored in the memory 1220. Functionality may also be implemented through various hardware components storing machine-readable instructions, such as application-specific integrated circuits (ASICs), field-programmable gate arrays (FPGAs) and/or complex programmable logic devices (CPLDs). Systems for medical device monitoring according to an aspect of the present invention may operate in conjunction with any desired combination of software and/or hardware components.

Medical Data Translator 1200

Figure 12B:
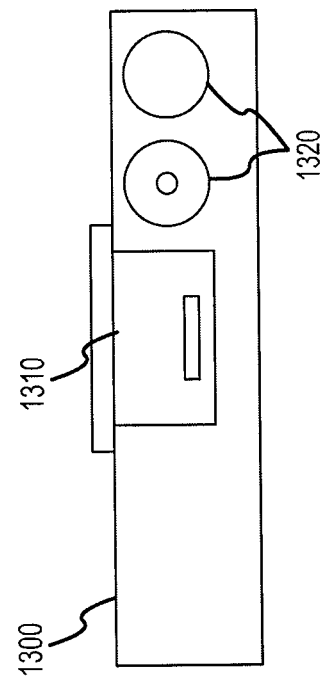
FIGS. 12A and 12B depict top and side views, respectively, of an external casing for a medical data translator device according to various aspects of the present invention.
Figure 12A:
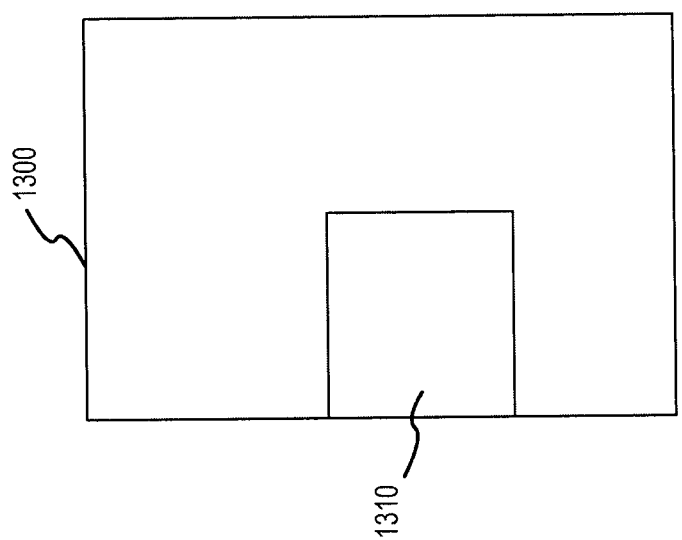

Referring to FIGS. 12A and 12B, the medical data translator 1200 depicted in FIG. 11 is shown enclosed within a within a case 1300. A case holding a system for medical device monitoring according to aspects of the present invention may be of any size, shape and configuration. The system (and case enclosing it) is preferably small enough to be easily portable by a patient or person being monitored. For example, the exemplary case 300 depicted in FIGS. 12A and 12B is 2.5 inches long, 2 inches wide, and 0.5 inches deep. The top and bottom of the case 1300 are 0.05 inches thick, while the sides of the case 300 are 0.075 inches thick. The case may be manufactured from any number of materials, such as plastic, metal, wood, composites, and/or any other suitable material. The case 1300 shown in FIGS. 3A and 3B, for example, is manufactured from hard plastic.

The case 1300 includes battery compartments 1320 for powering the data translator 1200. The case 1300 also includes an interface module 1310 that includes the adapter 1240. The interface module 1310 may include any suitable portion of the medical data translator 1200. In the exemplary embodiment depicted in FIG. 11, the interface module 1310 includes the adapter module 1240 comprising a medical device transceiver 1242 and auxiliary communication system 1244. In this embodiment, the interface module 1310 is removably attached to the case 1300 to allow different modules 1310 to be interchangeably connected to the case 1300 to communicate with different medical devices 1250.

Figure 12C:
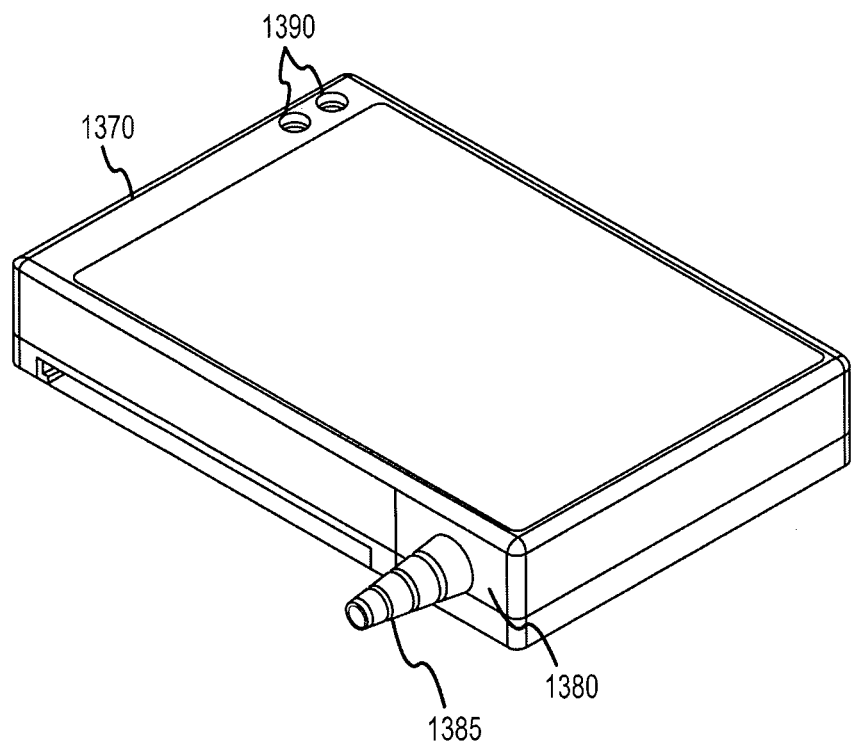
FIGS. 12C and 12D depict perspective views of another embodiment of an external casing for a medical data translator according to various aspects of the present invention.
Figure 12D:
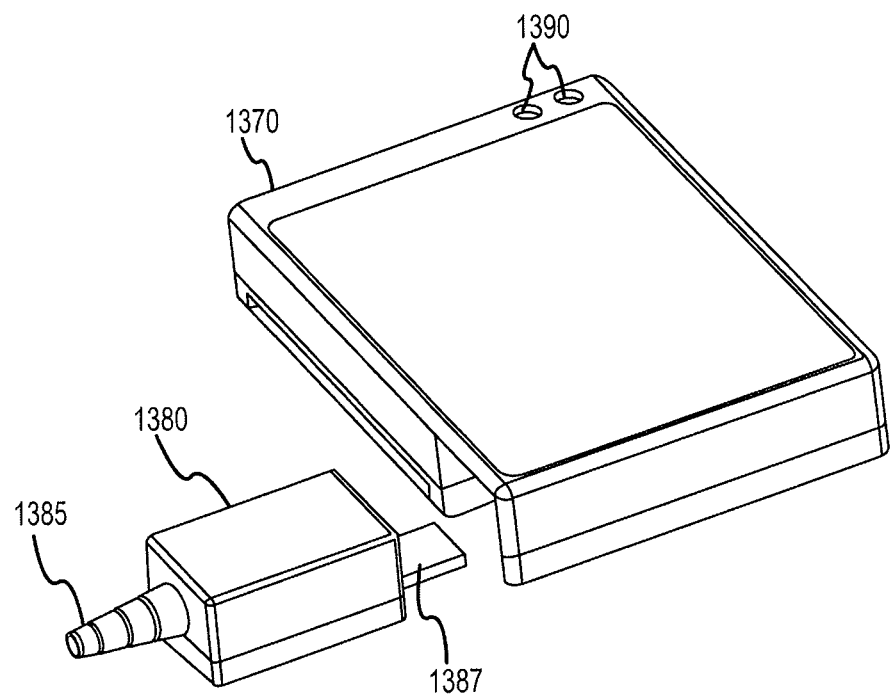
Figure 12E:
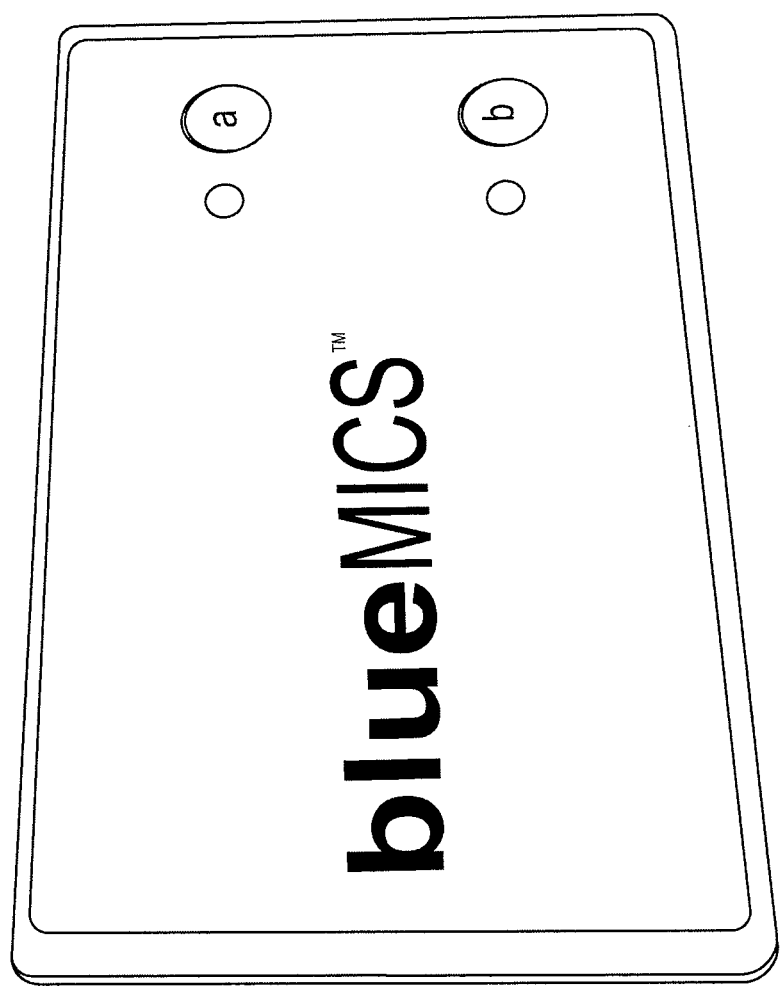
FIG. 12E depicts a perspective view of yet another embodiment of an external casing for a medical data translator according to various aspects of the present invention.

In another exemplary embodiment of the present invention, referring now to FIGS. 12C and 12D, a case 1370 includes a removable adapter module 1380 that includes an antenna 1385 for communicating with a medical device 1250 through a wireless connection. The adapter module 1380 connects to the case 1370 using plug 1387. The plug 1387 attaches to a corresponding port on the case 1370 (not shown) to hold the adapter module 1380 in place and allow the communication of data through the adapter module 1380. The plug 1387 can utilize any desired wired connection, such as a USB connection. The adapter module 1380 connects to the case 1370 using plug 1387. The plug 1387 attaches to a corresponding port on the case 1370 (not shown) to hold the adapter module 1380 in place and allow the communication of data through the adapter module 1380.

The case can include any other suitable features. For example, the case may include a screen, lights, LEDs, keys, speaker, and microphone grille to support features of a user interface included in a system for medical device monitoring. The exemplary systems for medical device monitoring shown in FIGS. 11, 12A, 12B, 12C, 12D and 12E are all configured to fit in a container along with the medical device it communicates with to allow a user to easily transport the medical device and the data translator together.

Other embodiments of systems for medical device monitoring according to aspects of the present invention can be configured to be in small enough to be coupled with or integrated into a medical device 1250 or an intermediary device 1260. For example, a medical device 1250 may be manufactured to include a medical data translator 1200 within the packaging housing the medical device 1250. Similarly, a medical data translator 1200 can be integrated as part of an intermediary device 1260 such as a cellular phone, PDA, or other mobile computing device. The intermediary device 1260 could thus be configured to both receive data from a medical device 1250 as well as transmit messages regarding the medical device 1250 and/or patient to a medical data server 1270.

Alternatively, a medical data translator 1200 can be configured to be physically attached to a medical device 1250 or intermediary device 1260. For example, where an intermediary device 1260 such as a mobile wireless telephone or PDA is used in conjunction with embodiments of the present invention, one exemplary embodiment of a medical data translator 1200 and its case 1300 is configured to match the size and shape of the of the intermediary device 1260 and attach to the back of the intermediary device 1260 using metal or plastic clips that wrap around the face and/or sides of the intermediary device 1260. When attached, the medical data translator 1200 conforms to the size and shape of the outline of the intermediary device 1260, and is preferably shaped to conform to the dimensions of the back of the intermediary device 1260 to avoid unnecessarily impacting the original size of the intermediary device 1260. In this embodiment, the case of the medical data translator 1200 may also include other desirable features, such as a belt clip to allow the data translator/intermediary device combination to be worn by a user.

Figure 13:
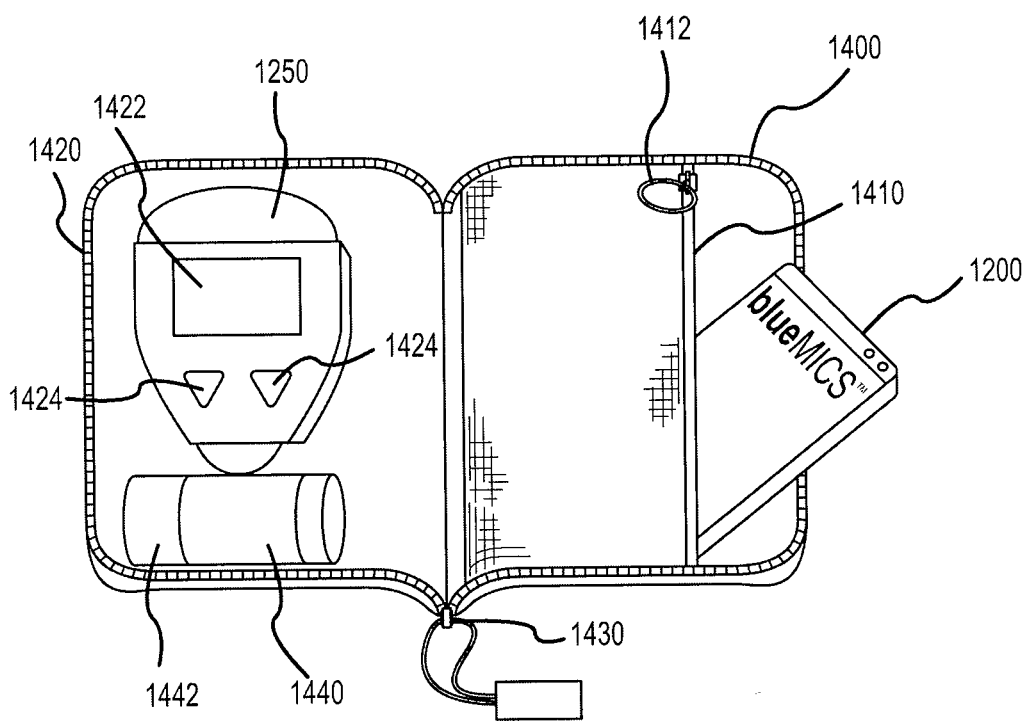
FIG. 13 depicts the interior of an exemplary container for holding a medical device and medical data translator according to various aspects of the present invention.

Turning to FIG. 13, in another exemplary embodiment of the present invention, the medical data translator 1200 is contained in a flexible, protective container 400 that opens to allow a medical device 1250 and/or intermediary device 1260 (such as a cellular phone, PDA, or other mobile computing device) to be likewise contained therein. This allows a medical data translator 1200 to be used with a variety of intermediary devices 1260, and may (in some cases) provide a more cost effective approach to integrate the medical data translator 1200 with an intermediary device 1260 or medical device 1250. In this embodiment, the medical data translator 1200 can be integrated within the protective container 1400 itself, with the container acting as the case for the data translator 1200.

Alternatively, as depicted in FIG. 13, the medical data translator 1200 may simply be contained within a pouch or other structure within the container 1400. The exemplary container 1400 depicted in FIG. 13 also includes a holder 1420 for the medical device 1250 formed from clear plastic to allow a user to read a display 1422 and/or operate keys 1424 on the medical device 1250. The protective container 1400 can also be sized to comfortably fit and protect any other desired item, such as a day planner, wallet, notepad, and/or writing utensil or PDA stylus. The protective container can be made from any desired material, such as leather, plastic, nylon, cordura, or other flexible material. The protective container can be sealed in any manner, such as by using snaps, hook-and-loop closures, buttons, and/or a zipper. The exemplary container 1400 depicted in FIG. 13, for example, is sealed using a zipper 1430. The container 1400 can be waterproof, heat resistant, and/or include padding to protect the medical data translator and other contents from the shock of a fall. The container 1400 may include any number of pockets, pouches, or other sub-containers inside or outside the case to hold accessories associated with the medical device 1250, intermediary device 1260, or other item(s) stored within the container 1400.

The exemplary protective container 1400 depicted in FIG. 13 is configured to hold a medical device 1250 (specifically, a glucose meter) and a medical data translator 1200 according to an aspect of the present invention. In this exemplary embodiment, the protective container 1400 is closed using a zipper 1430 that runs along the exterior of the sides of the container 1400. A user unzips the two halves of the container 1400 and opens the container 1400 to display the glucose meter contained in the holder 1420 attached to the interior of one half of the container 1400, while the medical data translator 1200 is contained in a pouch 1410 attached to the interior of the other half of the container 1400. The pouch 1410 is formed from a nylon mesh material to allow a user to see and/or interact with user interface features of the medical data translator 1200. The pouch 1410 is sealed with a zipper 1412. The container 1400 includes a flexible elastic strap 1440 to hold a container of blood sugar metering strips 1442. The container 1400 may include any number of other pouches or containers on the interior or exterior of the container for storing batteries and/or power cables for the glucose meter and/or medical data translator 1200, and other items of use to the patient carrying the container, such as bottles of insulin and needles for use by the patient depending on the outcome of a reading by the glucose meter.

Processor 1210

Figure 14A:
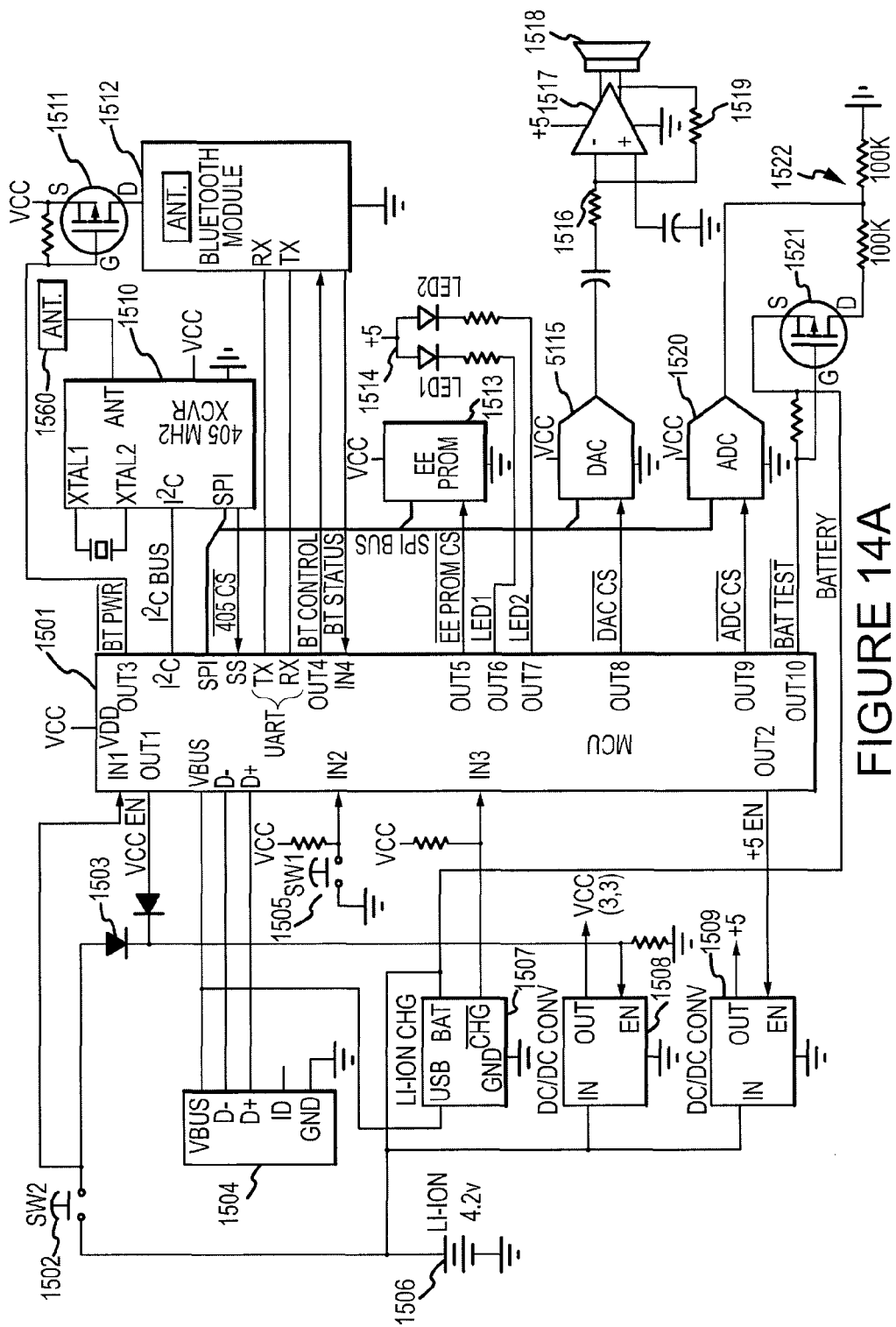
FIGS. 14A and 14B are a circuit diagrams depicting elements of exemplary medical data translators according to various aspects of the present invention.

The processor 1210 retrieves and executes instructions stored in the memory 1220 to control the operation of the medical data translator 1200. Any number and type of processor such as an integrated circuit microprocessor, microcontroller, and/or digital signal processor (DSP), can be used in conjunction with the present invention. Referring now to FIG. 14A, an exemplary medical data translator 1200 according to an aspect of the present invention is implemented using a microcontroller 1501. In the exemplary systems depicted in FIGS. 14A and 14B, the microcontrollers 1501 and 1530 include a Universal Asynchronous Receiver/Transmitter (UART) and Universal Serial Bus (USB). The microcontroller 1530 depicted in FIG. 14B additionally includes a digital signal processor (DSP) for communication with a cellular RF Transceiver 1540 as will be discussed in more detail below. The microcontrollers 1501, 1530 depicted in FIGS. 14A and 14B, respectively can include any other suitable components and features, such as analog-to-digital converters (ADCs) (1520), and/or digital-to-analog converters (DACs) (1515), though these components have been shown outside the microcontrollers 1501, 1530 for clarity.

Power Source

Figure 14B:
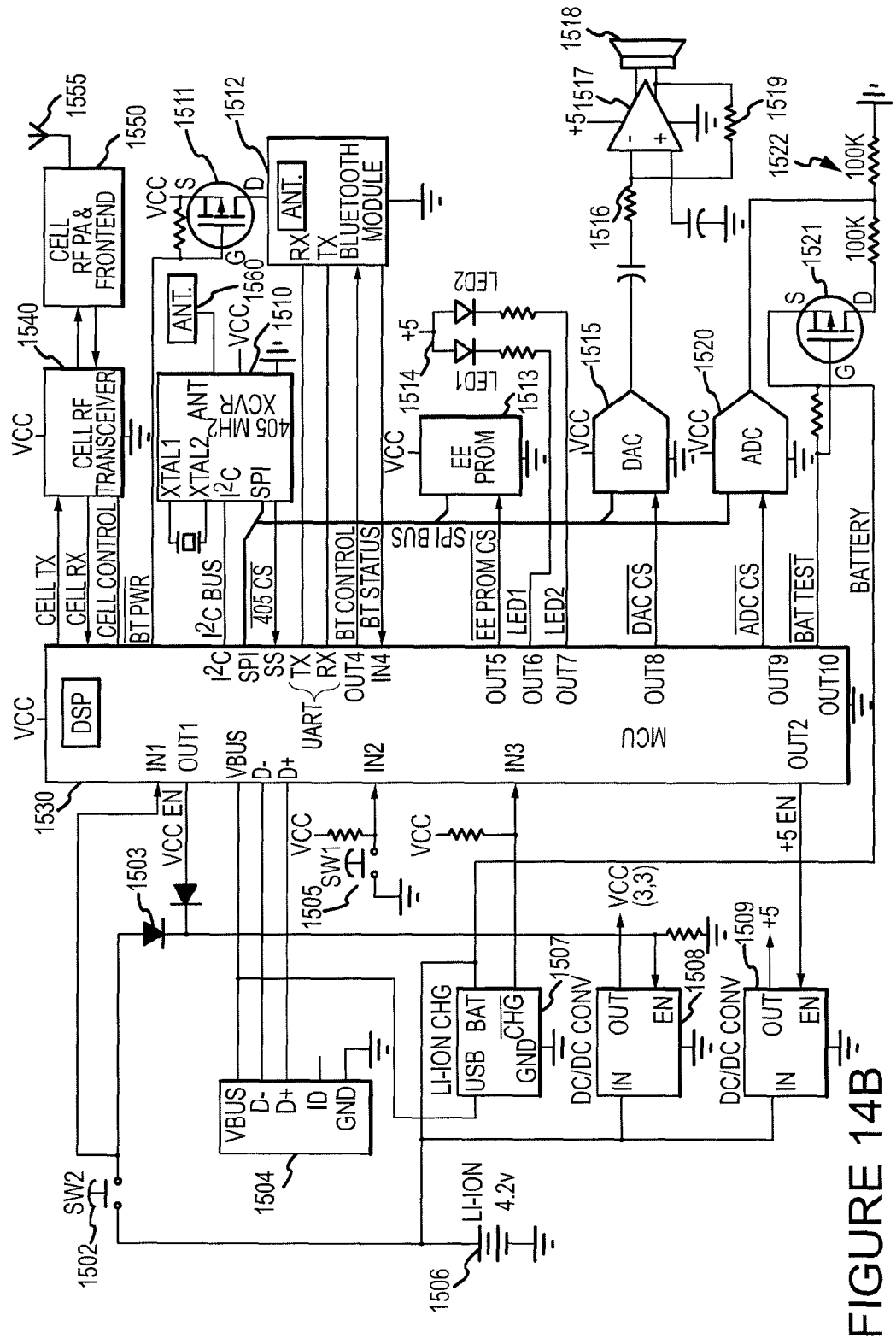

Any number, combination, and type of suitable power sources can be utilized in accordance with aspects of the present invention. The exemplary systems depicted in FIGS. 14A and 14B are powered by a rechargeable 4.2V Lithium Ion battery 1506. One DC to DC converter 508 is used to steps down the voltage from the battery 1506 to 3.3V for use by some components in the system, while another DC to DC converter 1509 is used to step up the voltage to 5V for use by other components. The battery 1506 can be recharged through the VBUS lead of the USB connector 1504 and charging circuit 1507. Both converters 1508, 1509 can be enabled and disabled via signals from the microcontroller 1501 on OUT1 and OUT2 to save power and extend the life of the battery 1506. The microcontroller 1501, 1530 can monitor the voltage of the battery 1506 using ADC 1520, FET circuit 1521, and voltage divider 1522. The voltage divider 1522 is used because the voltage of the battery 1506 when fully charged (4.2V) is greater than the maximum 3.3V input that can be accepted by the ADC 1250. The FET circuit 1521 connects the battery 1506 to the voltage divider 1522 only when a battery test is being performed (i.e.—when pin OUT10 is grounded) to avoid a constant drain on the battery 1506 when the system is otherwise powered down.

Any other suitable battery may be used according to any desired criteria. For example, a rechargeable battery or batteries integrated with the data translator may be selected to reduce the overall size of the medical data translator 1200 and/or provide for the convenience of a user who would not need to replace batteries. One or more standard replaceable batteries (i.e. alkaline AA or AAA batteries) may be selected to reduce the price of the medical data translator 1200. The power supply circuitry shown in FIGS. 14A and 14B is exemplary only, and may be implemented by using other conventional power supply approaches. The medical data translator 1200 and other systems for medical device monitoring according to various aspects of the present invention can utilize any appropriate power supply devices, components, circuits, and systems.

Memory 1220

The exemplary system in FIG. 11 includes a memory 1220. The memory 1220 stores instructions, medical device data, messages transmitted to or received from the medical data server 1270, and any other suitable information. A memory operating in conjunction with the present invention may include any combination of different memory storage devices, such as hard drives, random access memory (RAM), read only memory (ROM), FLASH memory, or any other type of volatile and/or nonvolatile memory.

In the exemplary embodiments of medical data translators 1200 depicted in FIGS. 13A and 13B, the microcontroller 1501 and 1530 each include an on-chip memory. In addition, the microcontroller 1501, 1530 is coupled to a flash memory 1513. The flash memory 1513 may be of any size to achieve any desired purpose. In this exemplary embodiment, the size of flash memory 1513 is selected to adequately store pre-recorded voice recordings to be played through the speaker 1518, discussed below. Any number of memory storage devices of any size and configuration may also be used in conjunction with the present invention.

Data Relay Transceiver 1230

The data relay transceiver 1230 communicates with one or more intermediary devices 260, medical data servers 1270, or other suitable systems. Any suitable communications device, component, system, and method may be used in conjunction with the present invention. In the exemplary circuits shown in FIGS. 14A and 14B, the data relay transceiver 1230 comprises a Bluetooth transceiver 1512 that is in bidirectional communication with the microcontroller 1501, 1530 through the UART interface on the microcontroller 1501, 1530.

The medical data translator 1200 may include, or operate in conjunction with, any number of data relay transceivers 1230. In FIG. 14B, for example the exemplary medical data translator 200 further includes a cellular radio frequency (RF) transceiver 1540 in communication with microcontroller 1530. In this exemplary embodiment, the microcontroller 1530 is a cellular baseband processor that includes a digital signal processor (DSP) which communicates data through a cellular RF power amplifier and front end 1550 connected to a cellular antenna 1555. Data is transmitted by the microcontroller 1530 on the CELL TX line and received by the microcontroller 1530 on the CELL RX line. Additionally, the microcontroller 1530 can control various features of the RF transceiver 1540 via the CELL CTRL line. The RF power amplifier and front end 1550 performs the necessary functions to transmit and receive cellular signals, such as power amplification, power detection, filtering, and input/output matching.

The medical data translator 1200 depicted in FIG. 14B may be configured to communicate using any number and type of cellular protocols, such as General Packet Radio Service (GPRS), Global System for Mobile Communications (GSM), Enhanced Data rates for GSM Evolution (EDGE), Personal Communication Service (PCS), Advanced Mobile Phone System (AMPS), Code Division Multiple Access (CDMA), Wideband CDMA (W-CDMA), Time Division-Synchronous CDMA (TD-SCDMA), Universal Mobile Telecommunications System (UMTS), and/or Time Division Multiple Access (TDMA). A medical data translator 1200 operating in conjunction with the present invention may alternatively (or additionally) include data relay transceiver 1230 components to communicate using any other method of wired or wireless communication.

As discussed previously, the medical data translator 1200 can transmit any data to any entity operating in conjunction with the present invention. For example, the medical data translators 1200 depicted in FIGS. 14A and 14B may transmit medical data to one or more intermediary devices 1260, as well as to one or more medical data servers 1270.

Adapter Module 1240

Referring again to FIG. 11, the exemplary medical data translator 1200 includes an adapter module 1240 for communicating with one or more medical devices 1250 as well as other suitable systems. The adapter module 1240 can be configured to communicate with any suitable class, type, and/or manufacturer of medical device 1250. The adapter module 1240 in this example includes a medical device transceiver 1242 for communicating with one or more medical devices 1250 and an auxiliary communication system 1244 for communicating with an external personal computer system 1280 to upload software to the data translator 1200, store data, provide or update encryption keys, perform diagnostics, and other appropriate purposes. The adapter module 1240 can be modular and removably attached to the body of the data translator 1200, integrated as part of the data translator 1200, or a combination of the two. Antenna 1243 may optionally be included in the adapter module 1240 assembly, or otherwise electrically coupled to the adapter module. In one exemplary embodiment of the present invention, the adapter module 1240 is removably attached to the body of the medical data translator 1200 to allow different medical devices 1250 to interoperate with the data translator 1200. As new medical devices 1250 and/or new frequencies are utilized, an adapter module 1240 configured to communicate with the new device or new frequency can be added to the existing system. In the exemplary circuits depicted in FIGS. 14A and 14B, any of the components used to communicate with other devices, such as the USB connector 1504, MICS transceiver 1510, and Bluetooth transceiver 1512 can be included in an adapter module 1240 that is removably attached to the body of the medical data translator 1200.

Software running on or operating in conjunction with the adapter module 1240 can be configured/updated through the auxiliary communication system 1244, the user interface 1290, or in response to a communication from an intermediary device 1260 or medical data server 1270 received through the data relay transceiver 1230. This allows the functionality of the medical data translator 1200 to be dynamically updated and avoids the expense of having to create custom hardware implementations for every type of medical device to be monitored.

Medical Device Transceiver 1242

The medical device transceiver 1242 wirelessly communicates with one or more medical devices 1250. The medical device transceiver 1242 may include any number and combination of hardware and/or software components. In the exemplary medical data translator 1200 depicted in FIG. 11, the medical device transceiver 1242 is integrated with the adapter 1240 and communicates with medical devices 1250 through an antenna 1243. In this way, adapters 240 that allow connections to different medical devices can be used interchangeably with the same medical data translator 200.

Any number of transceivers may be used in conjunction with the present invention, for example to communicate with multiple medical devices 1250 using different frequencies and/or communication protocols. The present invention may be used in conjunction with any communication protocol to communicate with one or more medical devices 1250. For example, the medical data translator 1200 may be configured to communicate with one or more medical devices using (without limit): the WMTS frequency bands (608-614 MHz, 1395-1400 MHz, and 1427-1432 MHz), the MICS frequency band (402-405 MHz), 32 KHz-175 KHz, as well as any other suitable frequency band. The medical data translator 1200 may communicate with medical devices using any other method of communication, such as infrared radiation, Zigbee protocol, Wibree protocol, Bluetooth connection, IEEE 802.11 protocol, IEEE 802.15 protocol, IEEE 802.16 protocol, and/or Ultra-Wideband (UWB) protocol. In alternate embodiments, the medical data translator 1200 may selectively communicate with one or more medical devices by using time division multiple access (TDMA), frequency division multiple access (FDMA), code division multiple access (CDMA), or other multiple access protocols.

In the exemplary embodiment depicted in FIG. 11, the medical device transceiver 1242 can be configured (e.g. through a software program residing in memory 1220 and executed by processor 1210) to detect and switch to different frequencies emitted from one or more medical devices 1243. Take for example, a hypothetical case where a patient has an implanted loop recorder broadcasting data regarding the patient's heart rate and rhythm using a MICS frequency, an implanted pacemaker broadcasting data at 32 KHz, and utilizes an external insulin pump communicating at 175 KHz. Each device could be produced by the same or separate manufacturers. The medical device transceiver 1242 according to various aspects of the present invention can be configured to detect the three devices and switch to the appropriate frequencies to communicate with each, thus providing interoperability between types and manufacturers of a wide variety of medical devices.

The medical data translator 1200 can be configured to automatically request data from one or more medical devices 1250 at predetermined times using the medical device transceiver 1242. Any appropriate date or time setting may be used. The data translator 1200, medical device 1250, or any other device operating in conjunction with the present invention can be configured to automatically request and/or transmit data in any suitable manner. For example, the medical data translator 1200 depicted in FIG. 11 can be configured through the auxiliary communication system 1244, the user interface 1290, and/or from a command issued transmitted by an intermediary device 1260 through the data relay transceiver 1230. In the case of a command received through the data relay transceiver 1230, the command can be generated by any suitable entity, such as from a medical data server 1260 or a user of the intermediary device.

The automatic requesting/transmission of data by a device operating in conjunction with the present invention may be subject to any suitable conditions or rules that dictate whether the data is in fact requested/transmitted. For example, a medical data translator 1200 programmed to request data from a medical device 1250 at a set time may first check to verify that the medical device is within range, that the translator 1200 has sufficient battery reserves to send the request and receive the data, whether the translator 1200 has sufficient space in the memory 1220 to store the data, and/or whether any other suitable condition is met.

In the exemplary circuits depicted in FIGS. 14A and 14B, the medical data transceiver 1242 comprises a 405 MHz transceiver 1510 in bidirectional communication with the microcontroller 1501, 1530 through an Inter-Integrated Circuit (I²C) bus interface and a Serial Peripheral Interface (SPI) bus interface. The transceiver 1510 sends and receives signals in the 402-405 MHz MICS band through antenna 1560. In this exemplary embodiment, the microcontroller 1501, 1530 can activate the transceiver 1510 periodically to monitor for incoming signals from one or more medical devices 1250. This mode of operation is useful for collecting data from medical devices 1250 that only broadcast data, but do not have the capability to receive requests for data. For medical devices 1250 that can both send and receive information, the microcontroller 1510, 1530 can activate the transceiver 1510 to send a request for data to one or more medical devices 1250. Both modes of operation help reduce the amount of time the transceiver 1510 is activated, and thus reduce the amount of power used by the system.

Auxiliary Communication System 1244

The adapter module 1240 depicted in FIG. 11 includes an auxiliary communication system 1244 for communicating with additional systems and devices. The medical data translator 1200 or other system operating in conjunction with the present invention can include any suitable circuit, component, device, and system for communicating with any other device. In the exemplary circuits depicted in FIGS. 14A and 14B, the auxiliary communication system 1244 comprises a USB connector 1504.

The auxiliary communication system 1244 can be used to transfer data to and from the medical data translator 1200, as well as for an external computer system 1280 to configure or program software and hardware in the data translator 1200. In one embodiment of the present invention, for example, a user operating computer system 1280 connected to medical data translator 1200 through the Internet can configure settings for the adapter module 1240, data relay transceiver 1230, and user interface 1290. The computer system 1280 can also download data received by the data translator 1200 from one or more medical devices 1250. Additionally, the computer system 1280 may communicate with the medical devices 1250 real-time through the medical device transceiver 1240, such as to monitor or control one or more medical devices 1250.

User Interface 1290

The medical device 1250, medical data translator 1200, intermediary device 1260, or other device operating in conjunction with the present invention may include a user interface. Referring to FIG. 11, an exemplary user interface 1290 of a medical data translator 1200 in accordance with aspects of the present invention includes an input device 1292 and an output device 1294. The input device 1292 receives commands, data, and other suitable input from a user. The output device 1294 provides the user with data, alerts, and other suitable information from the medical data translator 1200.

Any number of input devices may be included in a user interface for one or more devices in the present invention. In one embodiment of the present invention, for example, the user interface 1290 includes a touch pad, a touch screen, or an alphanumeric keypad to allow a user to enter instructions and data into the medical data translator 1200. One or more buttons on the keypad or touch screen can be programmed or configured to perform specific functions, such as to request data from one or more medical devices. The user interface 1290 can also include one or more multifunction switches, keys, or buttons that each allows a user to perform multiple functions.

The user interface may also include a microphone to allow the user to provide such information to the medical data translator 1200 verbally. In this exemplary embodiment, the medical data translator 1200 also includes speech recognition software to process verbal input through the user interface 1290. The ability of the medical data translator to recognize speech from a patient can be particularly useful for users/patients who have vision problems, arthritis, or other impairments that would inhibit them from using a keypad or other input device. A microphone can be used in conjunction with audible (e.g. through sound waves perceivable by the human ear) data provided through a speaker, as discussed below, to allow a user to interact with any device operating in conjunction with the present invention in a completely auditory manner. In one nonlimiting example, audible input could also be sensed and analyzed by the medical data translator 1200 that a patient has uttered a command, such as the command to turn on. Bidirectional audible communication, in addition to aiding impaired patients, allows users to operate devices in the present invention in a hands-free manner which can increase the speed, ease, and efficiency in which a device (such as the medical data translator 1200) can be utilized.

Devices operating in conjunction with the present invention may include any number of suitable output devices. Referring to the exemplary medical data translator circuits depicted in FIGS. 14A and 14B, a user interface including two lights 1514 (LED1 and LED2) may be used to indicate the status of the data translator to the user, as well as other pertinent information. For example, a flashing LED can be used to indicate when data from a medical device is in the process of being transferred, while a solid LED can indicate the transfer of data is complete. The medical data translators 1200 depicted in FIGS. 14A and 14B also provide auditory output through speaker 1518. The microcontroller 1501, 1530 retrieves audio samples, such as recorded speech, from the EEPROM 1513 and provides output to DAC 1515, which converts the digital signal from the microcontroller 1501, 1530 to an analog signal that can be output on the speaker 1518. The analog signal is provided to an audio amplifier 1517 that amplifies the signal. The gain of the amplifier 1517 is set by the ratio of resistors 1516 and 1519.

Any other suitable user interface features may similarly be included in devices and systems operating in accordance with the present invention. In another exemplary embodiment, for example, the output device 1294 includes a display screen to visually display information as well as a speaker (e.g. speaker 1518 shown FIGS. 14A and 14B) to provide auditory output. The output device 1294 can include multiple transducers such as audio speakers or piezoelectric elements, amplifiers, and other appropriate devices and systems to provide the auditory output. The medical data translator 1200 may be configured to provide words, phrases, tones, recorded music, or any other type of auditory output to a user.

Any type of information may be communicated through the user interface 1290, such as the biological, biometric, or behavioral information for one or more patients. The user interface can provide/receive any other suitable information, such as environmental information and/or diagnostic data for a medical device, a battery charge level, a temperature, a barometric pressure, a code relating to an accessory for the medical device, a biometric access measurement, a data validity measurement, an elapsed time since a previous reading by the medical device, a test result parameter, a signal-to-noise parameter, and a quality of service (QoS), and combinations thereof.

Information provided or received by the user interface 1290 may be in any appropriate format. For example, a user interface that communicates information to a user in an auditory format may first provide a data header followed by a data value to identify the data to the user. Similarly, an output device 1294 providing information to a user visually may provide a series of measurements in the form of a spreadsheet with headers indicating the source of the measurements. The output device 1294 can also provide information in any number of desired languages, regardless of whether the information is provided audibly or visually.

Various features of the user interface can be implemented in hardware, software, or a combination of the two. In the medical data translator 1200 depicted in FIG. 11, for example, the user interface 1290 includes voice interface software stored in the memory 1220, including tables of recorded words and phrases. When executed by the processor 1210, the voice interface software plays the appropriate recorded words and phrases (such as enunciating the medical data) through a speaker such as one included in the output device 1294 to provide information to the user. The voice interface software, like any software operating on the medical data translator 1200, can be downloaded and configured through the auxiliary communication system 1244. As discussed previously, any software program on any device operating in accordance with the present invention can be programmed or configured through any other suitable interface. In the medical data translator 1200, for example, the voice interface software could also be downloaded and configured through the data relay transceiver 1230 in response from a command from a medical data server 1270 and/or intermediary device 1260, as well as from input from the user through the user interface 1290. Accordingly, the voice interface software can be configured to include words and phrases in any number of different languages, and can be updated with new words and phrases as desired, such as to accommodate a new medical device 1250 operating with the medical data translator 1200. Non-verbal sounds, such as melodies and tones, can also be stored and used by the user interface 1294 to provide alerts, indicators, and other information to the user.

The user interface can also provide/receive information to a user in a machine-readable format. In one exemplary embodiment of the present invention, for example, the user interface 1290 of a medical data translator 1200 includes a fixed or retractable USB port to communicate with a thumb drive, memory stick, portable hard drive, an external computer system, or other USB-compatible device. This allows doctors and other healthcare providers to directly access the medical data translator 1200 directly, without having to retrieve the data from a medical data server. In this exemplary embodiment, the medical data translator 1200 can be configured to send, receive, and process machine-readable data can in any standard format (such as a MS Word document, Adobe PDF file, ASCII text file, JPEG, or other standard format) as well as any proprietary format. Machine-readable data to or from the user interface may also be encrypted to protect the data from unintended recipients and/or improper use. In an alternate embodiment, a user must enter a passcode to enable use of the USB port, and optionally, after a period of time of non-use, the USB port is automatically disabled. Any other user interface feature may be utilized to allow a human or non-human user to interact with one or more devices operating in conjunction with the present invention.

Power Saving Features

A medical data translator, intermediary device, medical device, or other system operating in accordance with aspects of the present invention may include any other suitable features, components, and/or systems. For example, the data translator 200 or other device may be configured to preserve the life of its battery by shutting off or going into a low-power mode when it, and/or the medical device it monitors, experiences a predetermined period of non-use, or a change in a measured parameter such as indication that a case holding the translator 1200 has been actuated to a closed position. Such devices can also be configured to become active in response to any suitable event, such as receiving a signal from a device (such as a sensor).

In one non-limiting embodiment of the present invention, referring now to FIG. 6, a medical data translator 1200 communicates with a motion sensor 1610 and a light sensor 1620 to determine when a container 1630 holding the data translator 1200 and the medical device 1250 it monitors is open or closed. In this exemplary embodiment, the data translator 1200 can preserve the life of its battery by shutting off or going into a low-power mode when the container 1630 is closed and, therefore, the medical device 1250 held in the container 1630, is not in use. Any type of motion sensor can be used in accordance with the present invention, such as an accelerometer, tilt switch, or other device that generates a signal in response to movement. Similarly, any type of light sensor may be used in conjunction with the present invention. The light sensor can be used to detect the amount of light entering a container 1630 holding the medical device 1250, medical data translator 1200, or other device to activate the device when the sensed amount of light exceeds a predetermined threshold, or if an increase in the amount of incident light exceeds a predetermined threshold. In an alternate embodiment, a microphone may receive audible signals that are analyzed by the medical data translator 1200 to determine that a command has been uttered, and such a command may include instructions that the medical data translator 1200 should be shut down or activated from a quiescent or low-power state.

Figure 15:
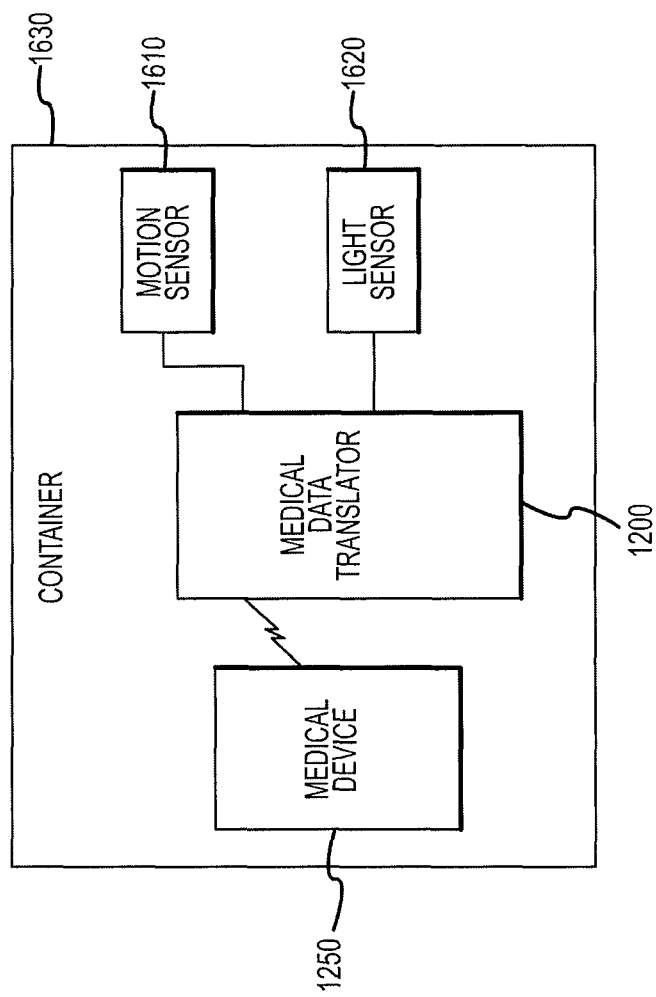
FIG. 15 is a block diagram depicting a container including light and motion sensors for activating a medical data translator in accordance with various aspects of the present invention.

A sensor may be integrated into the medical data translator 1200, or operate externally to the data translator 1200, communicating with the data translator 1200 wirelessly or through a wired connection. For example, in the exemplary embodiment depicted in FIG. 15, the motion sensor 1610 and light sensor 1620 are integrated into the interior of the container 1630 and communicate with a medical data translator 1200 contained within to indicate when the container 1630 is actuated from a closed position to an open position.

Security Measures

Systems and devices operating in accordance with aspects of the present invention may implement one or more security measures to protect data, restrict access, or provide any other desired security feature. For example, any device operating in conjunction with the present invention may encrypt transmitted data and/or protect data stored within the device itself. Such security measures may be implemented using hardware, software, or a combination thereof. Any method of data encryption or protection may be utilized in conjunction with the present invention, such as public/private keyed encryption systems, data scrambling methods, hardware and software firewalls, tamper-resistant or tamper-responsive memory storage devices or any other method or technique for protecting data. Similarly, passwords, biometrics, access cards or other hardware, or any other system, device, and/or method may be employed to restrict access to any device operating in conjunction with the present invention.

Exemplary Method for Medical Data Collection and Transmission

Figure 16:
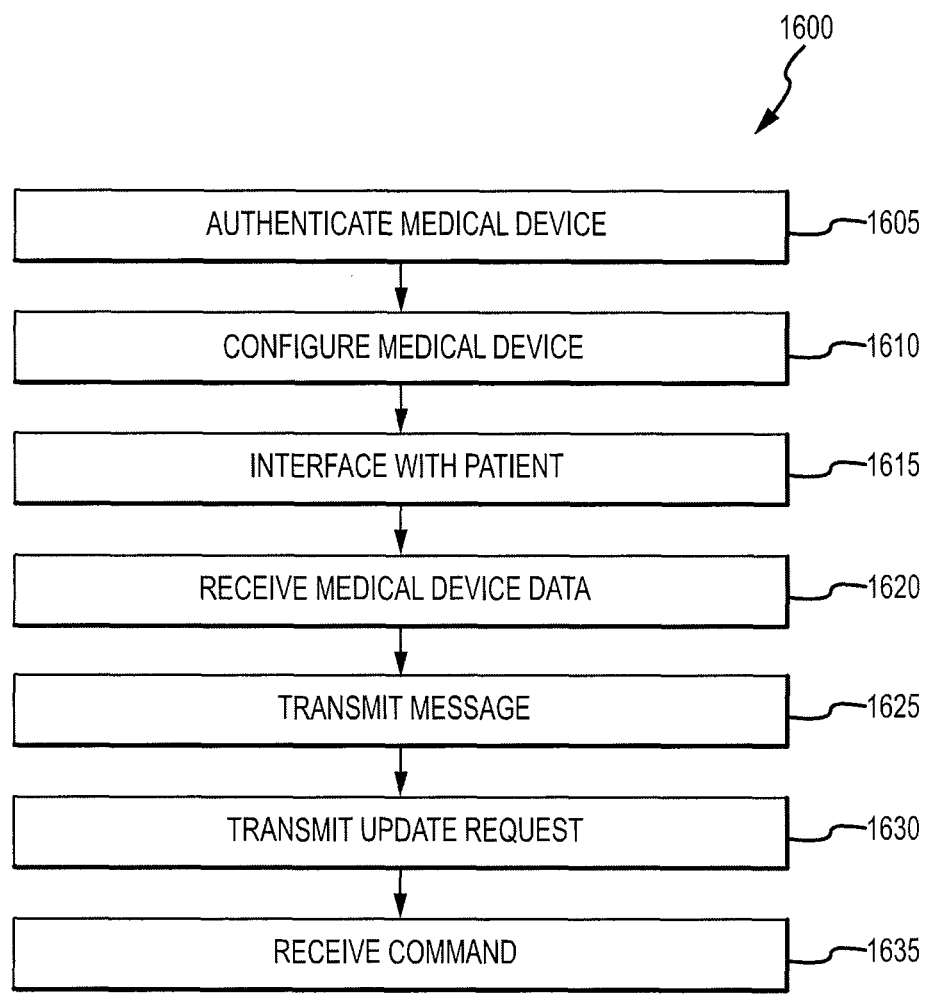
FIG. 16 is a flow diagram illustrating an exemplary method in accordance with various aspects of the present invention.

FIG. 16 illustrates an exemplary method 1600 for medical data collection and transmission according to various aspects of the present invention. In method 1600, a medical device is authenticated (1605) and configured (1610). An interface with the patient may be established (1615) and data is received from the medical device (1620). A message including some or all of the medical device data is transmitted (1625). A request for a software or firmware update may also be transmitted (1630) and a command received (1635).

A medical device can be authenticated or authorized in any suitable manner, including the authentication methods described above. In one exemplary embodiment, the system 1700 is configured to automatically connect to, and communicate with, a medical device (either directly or through an intermediary device) with little or no action required by a user. The system 1700 can also be configured to automatically change settings on the medical device, as well as to download firmware or software updates to the medical device from a medical data server or other source. In this manner, the present invention allows medical devices to be quickly configured to upload data to the system 1700 without requiring a user (such as a patient or caregiver) to manually set up the medical device to communicate with the system 1700.

Information can be provided to, or received from, a user (such as a patient or healthcare worker) (1615). Information can be provided or received through a user interface of the medical device 1750, user interface 1790 of the system 1700, or user interface of another device operating in conjunction with the present invention. In one exemplary embodiment of the present invention, the user interface 1790 may provide information to a user such as an indicator as to whether a medical device is currently in communication with the system, an indicator that the system has received medical data from a medical device, a survey regarding a treatment for a patient, and/or an indicator regarding the status of an update to a software application operating on a medical device. Any other suitable information can also be provided to a user. A system operating in conjunction with the present invention may also receive any suitable information from a user, including information regarding a treatment for a patient, an indicator that a patient is in need of assistance, and/or a communication from a patient for delivery to a caregiver of the patient.

In the exemplary method 1600, data is received from one or more medical devices (1620). The data can be received by any suitable system or device, such as through the device interface 242, 1242, or 1742 of a medical data interchange device 200, medical data translator 1200, or medical data collection and transmission system 1700, respectively. The received data may include any suitable information for one or more patients, including a location for a patient, a patient identifier (such as the patient's name or a number associated with the patient), a health status indicator (e.g., an indicator that the patient's medical data is within or outside ordinary levels, the patient needs help, the patient is having a health emergency, the patient needs to take one or more medications, and/or the patient is outside a predetermined boundary), biological information for a patient, biometric information for a patient, behavioral information for a patient, and/or any other suitable information, including the environmental information and diagnostic data for a medical device discussed previously.

Data may be received from a plurality of medical devices. Each of a plurality of medical devices can be associated with a single respective patient, or each medical device can provide data regarding a plurality of patients. Data may be received from one or more medical devices in any desired manner. For example, the data interface 1742 of system 1700 may receive data from any type of wired or wireless connection, including those described above in conjunction with the adapter 240, device interface 242, and device interface 1242.

A message including at least a portion of the medical device data is transmitted to a medical data server (1625). A transmission method may be selected according to any suitable criteria, including those described above for steps 160 and 1160. The message can be transmitted to a medical data server and/or to an intermediary device configured to (e.g., using a software program) retransmit the message to the medical data server. Medical data servers and intermediary devices operating in conjunction with the present invention are described in detail above. The message can be transmitted to a medical data server and/or intermediary device in any suitable manner, such as through the data relay transceiver 230 or 1230 of a medical data interchange device 200 or medical data translator 1200, respectively. Additionally, the message can be transmitted through a wired or wireless connection using the data relay interface 1730 of the system 1700. The message may include some or all of the data received from one or more medical devices. Part or all of the message may be encrypted using, for example, the encryption mechanisms described above.

A request for an update may be transmitted to a medical data server or other system or device (1630). The update request may include any suitable information, including an identifier for a medical device to be updated and/or a current software or firmware version for the medical device. The update request may also be used to obtain an update for the system 1700 itself, as well as any other device that communicates with the system 1700 through the device interface 1742 or data relay interface 1730. The update request can be transmitted through any wired or wireless connection, including those described previously.

In method 1600, a command is received from a medical data server. The command can be transmitted by a medical data server in response to input from a user of the medical data server or a device in communication with the medical data server (e.g., system 1700), such as a request for an update (step 1630 above). The command may be provided for any purpose, including those described above in conjunction with steps 160 and 1160 above. In one exemplary embodiment, a command from the medical data server can be used to reconfigure a software application running on the system 1700, control one or more medical devices 1750, and/or reconfigure a software application on a medical device 1750.

Exemplary System for Medical Data Collection and Transmission

Any of the systems and devices depicted in FIGS. 2A-8 and FIGS. 11-15 can be used to collect and transmit medical data according to various aspects of the present invention, such as the method depicted in FIG. 16.

Figure 17:
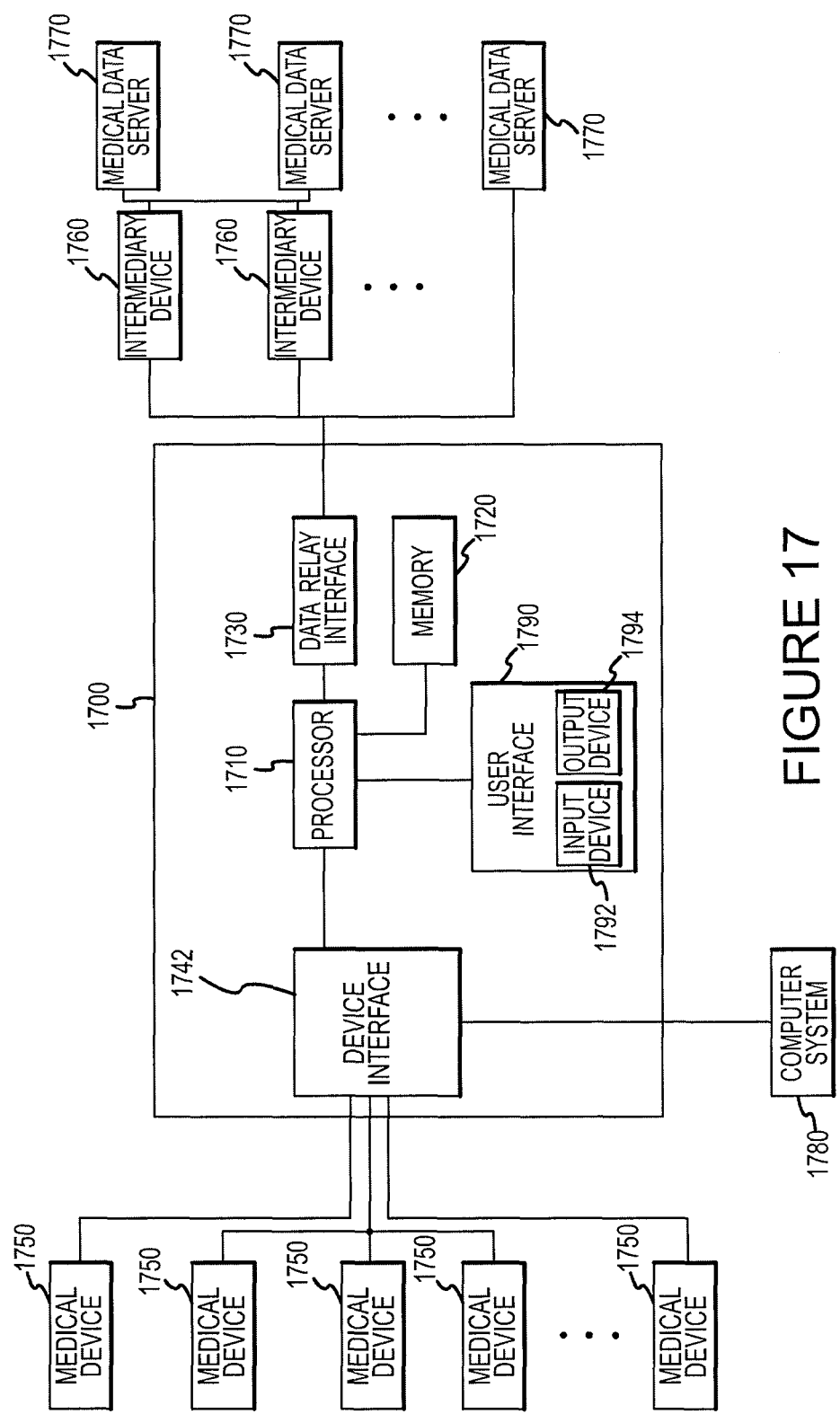
FIG. 17 is a block diagram depicting an exemplary system for medical data collection and transmission.

Additionally, an exemplary system for medical data collection and transmission is depicted in FIG. 17. In this exemplary embodiment, system 1700 includes a processor 1710 in communication with a memory 1720. A data relay interface 1730 communicates with one or more medical device servers 1770 (directly or through one or more intermediary devices 1760) through a wired and/or wireless protocol. A device interface 1742 communicates with one or more medical devices 1750. The device interface 1742 also communicates with any number of other external devices, such as a computer system 1780. The device interface 1742 may support any number of wired or wireless connections, including those described above for device interfaces 242 and 1242.

In one exemplary embodiment, the processor 1710 executes software instructions stored in the memory 1720 of system 1700 to perform the steps of the method in FIG. 16.

The device interface 1742 communicates with one or more medical devices 1750 while the data relay interface communicates with one or more intermediary devices 1760 and/or medical data servers 1770. In another exemplary embodiment, the steps of the method in FIG. 16 can be performed by software operating on a medical data interchange device 200 and/or medical data translator 1200.

The system 1700 may include any number and type of processor 1710 and memory 1720, including the processors and memories described above for components 210, 1210, 220, and 1220 above. Medical devices 1750 may include any type of medical device, including the devices described above for medical devices 250 and 1250. A medical device 1750 may communicate with the device interface 1742 in any desired manner, including the wired and wireless communication protocols described above for medical devices 250 and 1250 above.

The data relay interface 1730 communicates with one or more intermediary devices 1760 and/or medical data servers 1770. The intermediary devices 1760 and medical data servers 1770 may include any of the features and functionality described above for intermediary devices 260 and 1260, and medical data servers 270 and 1270, respectively. The data relay interface 1730 may communicate through a wired and/or wireless connection, including any of the wired and wireless connections described above.

A medical data server operating in conjunction with the present invention may include a memory storage device and a processor. The medical data server may include any number and type of processors to retrieve and execute instructions stored in the memory storage device of the medical data server to control its functionality. Any number and type of conventional computer, computer system, computer network, computer workstation, minicomputer, mainframe computer, or computer processor, such as an integrated circuit microprocessor or microcontroller in accordance with the present invention.

The message can be transmitted to, and received by, the medical data server or intermediary device in any suitable manner, including through a wired connection, such as a telephone line, fiber optic cable, and/or coaxial cable. The message may also be transmitted wirelessly using any suitable wireless system, such as a wireless mobile telephony network, General Packet Radio Service (GPRS) network, wireless Local Area Network (WLAN), Global System for Mobile Communications (GSM) network, Personal Communication Service (PCS) network, Advanced Mobile Phone System (AMPS) network, and/or a satellite communication network. The message may also be transmitted using any suitable combination of multiple wired and wireless communication methods. The transmission method selected to transmit the data to the medical data server can be chosen according to any desired criteria. For example, one or more transmission methods can be selected from a plurality of possible transmission methods to send the data based on each method's cost, time required to transmit, reliability, security, or any other suitable factor. The message may be received in any other manner, such as by an interactive voice response (IVR) system, a mobile computing device, a mobile telecommunication device, a computer system connected to a network, and/or a human operator.

An intermediary device 1760 or medical data server 1770 operating in conjunction with the present invention may include any combination of different memory storage devices, such as hard drives, random access memory (RAM), read only memory (ROM), FLASH memory, or any other type of volatile and/or nonvolatile memory. A medical data server or intermediary device may include an operating system (e.g., Windows NT, 95/98/2000/XP/Vista, OS2, UNIX, Linux, Solaris, MacOS, etc.) as well as various conventional support software and drivers typically associated with computers. Software applications stored in the memory may be entirely or partially served or executed by the processor(s) in performing methods or processes of the present invention.

The medical data server 1770 or intermediary device 1760 may also include a user interface for receiving and providing data to one or more users (such as a doctor, nurse, or patient). The user interface may include any number of input devices such as a keyboard, mouse, touch pad, touch screen, alphanumeric keypad, voice recognition system, or other input device to allow a user or patient to provide instructions and information to the medical data server. Similarly, the user interface may include any number of suitable output devices, such as a monitor, speaker, printer, or other device for providing information to one or more users.

The device interface 1742 communicates with, and receives data directly or indirectly from, one or more medical devices through wired and/or wireless connections, including those previously described. In one embodiment, the device interface 1742 includes an RJ11 connector for connecting to a telephone line. The device interface 1742 can communicate with different medical devices 1750 (or devices relaying/transmitting medical device data) through different connections to allow medical device data to be quickly and efficiently collected by the system 1700. The device interface 1742 can also communicate with other devices, such as one or more computer systems 1780. The system 1700 can track the status of multiple medical devices it is in communication with, and report this information in a message transmitted to a medical data server 1770. The medical data server 1770 can, in turn, provide a command to the system 1700 to configure one or more medical devices according the specific requirements for one or more patients.

In one exemplary embodiment, the device interface 1742 delivers software and/or firmware updates to medical devices 1750 and/or computer systems 1780 in communication with system 1700. The system 1700 can receive such updates and store them in the memory 1720 (or other storage device in communication with the system 1700) until the appropriate device(s) is in communication with the system 1700 to receive the update. The device interface 1742 may communicate with a device through any of the wired or wireless connections described above for device interface 242, 1242, and adapter 240 or 1240. Additionally, the device interface 1742 may communicate with a medical device 1750 or other device through a docking connection. A docking connection operating in conjunction with the present invention may be used to supply power to the medical device (e.g., to recharge its battery), establish data and user-interface connections, or provide any other desired function. In one exemplary embodiment, the docking connection is a 30-pin interface configured to connect with a mobile device (e.g., IPOD, IPHONE, IPAD, and other devices). Any other type of docking connection may also be used in conjunction with the present invention.

In one exemplary embodiment, the device interface 1742 includes an interface for communicating with a flash memory card, such as a SECURE DIGITAL (SD) memory card. The SD card can be used to upload information (including software or firmware updates for the system 1700 or a medical device 1750), as well as to store data (including data from one or more medical devices 1750). Similarly, the device interface 1742 may also be configured to load data from, and store data to, a portable hard drive or other storage device through a Universal Serial Bus (USB) connection or other suitable connection. Among other things, this allows a nurse or other healthcare provider to load data from one or more systems 1700 and generate reports based on the medical data for one or more patients.

Information can be provided to, or received from, a user (such as a patient or healthcare worker) through the user interface 1790, which may include any number and type of input devices 1792 and/or output devices 1794, including any of the input and output devices described previously. In one embodiment, the user interface 1790 includes one or more lights and/or a display to convey information to a user, such as an indicator as to whether a medical device is in communication with (e.g., secured in a docking port of the device interface 1742) the system 1700, and/or an indicator that a command (e.g., including a software update) is waiting for retrieval by a medical device and/or user.

A plurality of medical interchange devices 200 (receiving medical data through wired connections), medical data translators 1200 (receiving medical data through wireless connections), and medical data collection and transmission systems 1700 can be used (e.g., either stand-alone or networked together) in a healthcare-related facility, such as a hospital or nursing home, to retrieve data from multiple medical devices and from multiple patients to help monitor groups of patients. Among other things, the present invention allows a patient to upload his or her data from a medical device with little or no action required by the patient. This simplifies the collection of medical data and allows for health care providers to deliver treatments to patients more quickly and efficiently.

Electronic Device Software Provisioning and Configuration

It is desirable to be able to remotely update devices with embedded processors and/or microcontrollers in the field—often referred to as "Firmware Over The Air" (FOTA). The program memory in microcontrollers today almost always includes nonvolatile memory such as FLASH memory or the like. For FOTA to be possible, microcontrollers must be able to re-load software into its nonvolatile memory (or "re-flash itself"). Several microcontrollers from multiple vendors have this capability. As an illustrated non-limiting embodiment, there is presented an 8051 microcontroller series from Silicon Labs, and the PIC24F series from Microchip Technology Inc. Although Over the Air (OTA) implies a wireless connection, the techniques described here are not limited to wireless updates; for example in the case of updating the code in a docking station, the software and/or firmware file might be downloaded by the mobile device that is docked/connected to the docking station, and transferred over a data bus (such as a serial bus) from the docked device to the docking station. Alternatively, a mobile device might be connected to a computer via a USB cable and software/firmware automatically downloaded and configured. Method consistent with embodiments of the present invention for providing FOTA downloads and configuration as described herein have advantages such as: (a) an embedded system program includes two independently compiled programs (boot and application), which maybe run separately for testing purposes; (b) code may be written in high level languages such as "C" without necessarily having to resort to assembly code, or use special higher-language startup code; (c) generally the application code can be modified during development much more often than the boot code, and in various embodiments of the present invention it is not necessary to flash the boot program in order to test the application program since the latter is self-booting when run standalone; (d) once the boot program is written to nonvolatile memory, it can be "locked down" (inhibiting further writes) since loading and flashing the application programming does not require anything in the boot program space to be modified; (e) if there is a problem with a downloaded program, for instance if it is corrupted or it causes a watch-dog timer reset within a few minutes of starting up, then the boot code can revert back to an earlier version of the application code automatically, and a user of the mobile device can revert back to the factory-installed version of the application manually.

In a preferred embodiment of the present invention, the linker or compiler of the software development environment supports absolute placement of functions and data, and is able to determine the end of the program. The fixed program locations are used to locate subroutines at fixed addresses that do not change from one build of the program to the next, which can be called by interrupt service routines ("ISR's"). The fixed data locations are used to locate global variables that can be shared between the application and boot code across a hardware reset. Preferably, they should also be declared persistent (i.e., not initialized by the higher level language startup routine such as a C-startup routine). These features are not part of the standard C language, but are generally provided by C compilers targeted for embedded systems use. An assumption about the compiler is that the microcontroller's reset vector jumps to the C-startup routine, which in turn calls the main function of the program. Neither the C-startup routine or main function need to be at fixed locations in either the boot or application code. The memory map varies slightly depending on whether the underlying microcontroller has one or multiple sets of interrupt vectors. In the case of the Silicon Labs 8051 series, which has one set of interrupt vectors, the configurations shown in FIGS. 18-20 apply. In the case of the Microchip PIC24F microcontroller series, which has two sets of interrupt vectors, the configurations shown FIGS. 21-23 apply. Both of these sets of examples have interrupt vectors located at the "bottom" (starting at address 0) in the microcontroller's address space, which is typical of microcontrollers using Harvard architecture (separate address space for program and data). Similar concepts described in accordance with the preferred embodiments would also apply to alternate embodiments if the reset and interrupt vectors were at the top of the microcontroller's address space, such as may be the case with processors such as the Freescale HCS08 series, which uses Von Neumann architecture (combined address space for program and data). In either architecture, one portion of the program (e.g. boot) should be able to re-flash another portion of the program space (the application) in place.

Single Set of Interrupt Vectors

Figure 18:
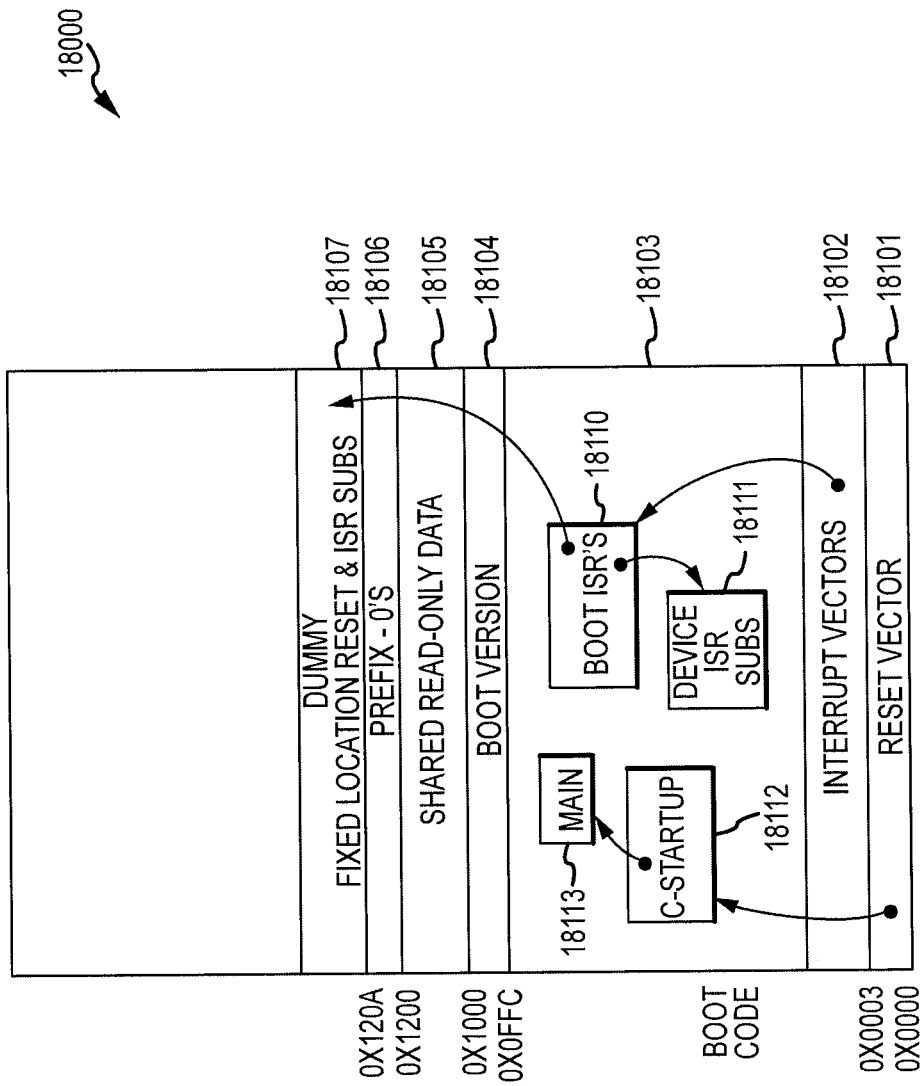
FIG. 18 is an illustration of a boot image of a single set of interrupt vectors.

FIG. 18 shows a boot portion of code after it is compiled and linked. The specific addresses discussed are only examples and could vary, both due to different microcontrollers and/or different relative sizes of the boot and application code on the same microcontroller. The reset vector, which gets control whenever there is a hardware or software reset, is located at address 0x0000 in this example (18101). In the case of the 8051, it implemented as a jump instruction to the beginning of the C startup code (18112). This code (which may be part of a library included with a compiler, and may be hidden from the program) initializes the microcontroller's stack pointer, initializes all global variables, and then calls the main( ) function (18113) in the boot program. Since in preferred embodiments shown in FIGS. 18-20 there may be two separately compiled programs, "boot" and "app," there are two C-startup sections (20312, 20315) and two main( ) functions (20313, 20316), where one of each respectively occurs in each image. In the exemplary 8051 architecture, interrupt vectors start at address 0x0003 and repeat every eight bytes (18102) allowing room for either a very small interrupt service routine (ISR) or a jump to one. In this exemplary embodiment, the ISRs are located within the body of the code ("boot ISRs," block 18110) which can be located anywhere in the boot image 18000, so each vector 18102 contains an interrupt jump to its associated ISR in block 18110. As will be explained, steps of the method are performed via subroutines called within each boot ISR; the corresponding subroutines for the boot ISR code is contained in block 18111 ("device ISR subs") which can be located anywhere in the boot image.

In an exemplary embodiment, the size of the boot code is less than a particular desired boundary, such as less than 4092 (0x1000-4) bytes in length, so a virtual "fence" may be placed at address 0x0FFC where there is a four-byte block to hold the version number of the boot code (e.g. 1.0.1.3 would be stored as the separate bytes 0x01, 0x00, 0x01, 0x03). This version number, being at a fixed location, will be available to the application program. At a fixed address such as address 0x1000 (block 18105), a read-only data section is shared by both the boot and application programs for reasons such as to save space. In this example, the shared data space 18105 is 512 bytes long, but may be any length depending on the particular needs of the embodiment. At another fixed address such as address 0x1200 (block 18106), a prefix area such as a 10-byte prefix is defined in the boot image as a placeholder. At another fixed location, for example 0x102A (block 18107) a set of subroutines is defined, each containing a call to another subroutine. In the boot image, this area (18107) contains "dummy calls" not generally intended to be used by the boot image; in the application image, which may overlay this same fixed address space, these calls will be to the device ISR subroutines for the application. The code generated will preferably be the same size in both images, so the addresses will preferably be fixed for each vector. All of the exemplary fixed addresses (0xFFC, 0x1000, 0x1000, 0x120A) are just examples and would vary depending on the particulars of the program being developed.

Figure 19:
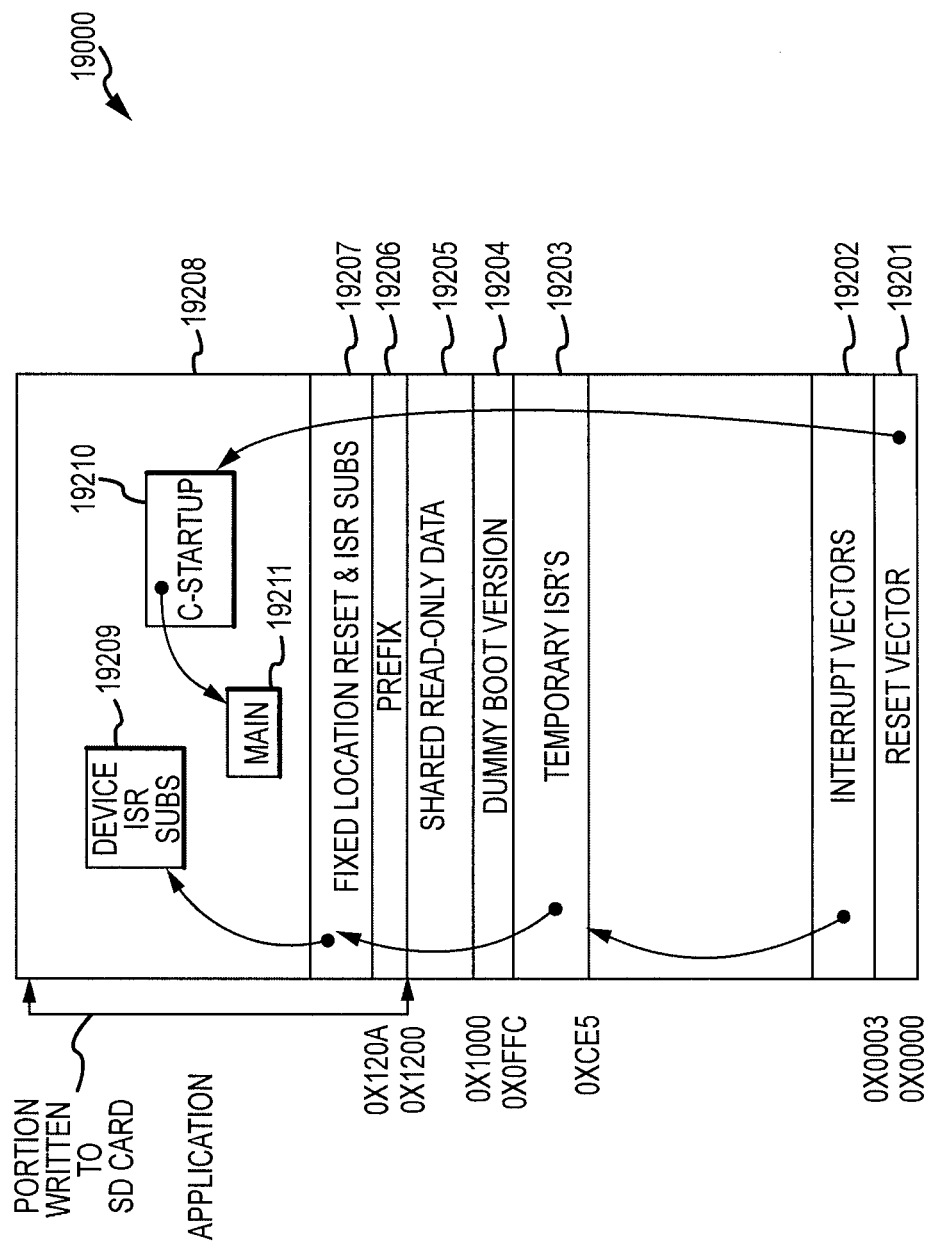
FIG. 19 is an illustration of an application image of a single set of interrupt vectors.

FIG. 19 shows the application portion 19000 of the code after it is compiled and linked. Again, the addresses discussed are only examples and could vary, both due to different microcontrollers and/or different relative sizes of the boot and application code on the same microcontroller; however for a particular embodiment the fixed addresses in the application image should match those in the boot image. The reset vector is located at address 0x0000 in this example (item 19201). In the case of the 8051 microprocessor, it implemented as a jump instruction to the beginning of the C startup code (19210). As before, this code initializes the microcontroller's stack pointer, initializes all global variables, and then calls the main( ) function (19211) in the application program. As before, the generated interrupt vectors (19202) will be located at a fixed address such as address 0x0003, and repeat every eight bytes, so each vector in block 19202 contains a jump to its associated ISR, which in this case resides in block 18203. When the application image 19000 is executed by itself, it needs a temporary set of ISR routines 18203, which are placed beneath the exemplary "fence" at address 0xFFC. As before, steps of the present method are actually performed via subroutines called within each ISR; for example, the corresponding subroutines for the application code 19000 is contained in block 19209 (device ISR subs) which can be located anywhere in the application image. In this example, the temporary ISRs start at address 0xCE5. This address will change depending on the number of interrupt vectors implemented. Note this address is placed approximately in the middle of the boot code, and will be overlaid when the boot image 18000 is programmed. This does not create a problem, as the boot code will also rewrite the interrupt vectors to point to its own ISRs (block 18110 in FIG. 18). In the exemplary embodiment, the space between the end of the interrupt vectors (block 19202) and the start of the temporary ISRs (block 19203) is not used.

Once again, we can put an exemplary "fence" at address 0x0FFC where there is a four byte block (19204) to hold the version number of the boot code. In the application image 19000, this is only a placeholder which will be overwritten with the actual boot version number when the boot program is overlaid. At a fixed address such as 0x1000 (block 19205) is a read-only data section which is shared by both the boot and application programs (shown as 18105 in FIG. 18) to save space. In this example, it is 512 bytes long, but may be any length depending on the needs of the particular implementation. At fixed address such as address 0x1200 (block 19206) a 10-byte prefix area is defined which in the application image is a placeholder in the C code (initialized to zeroes, for instance), but is filled in by a utility before generating the FOTA image which will be discussed below. At a fixed location such as address 0x102A (block 19207) a set of subroutines is defined, each containing a call to a corresponding subroutine in the device ISR subroutines block 19209.

Figure 20:
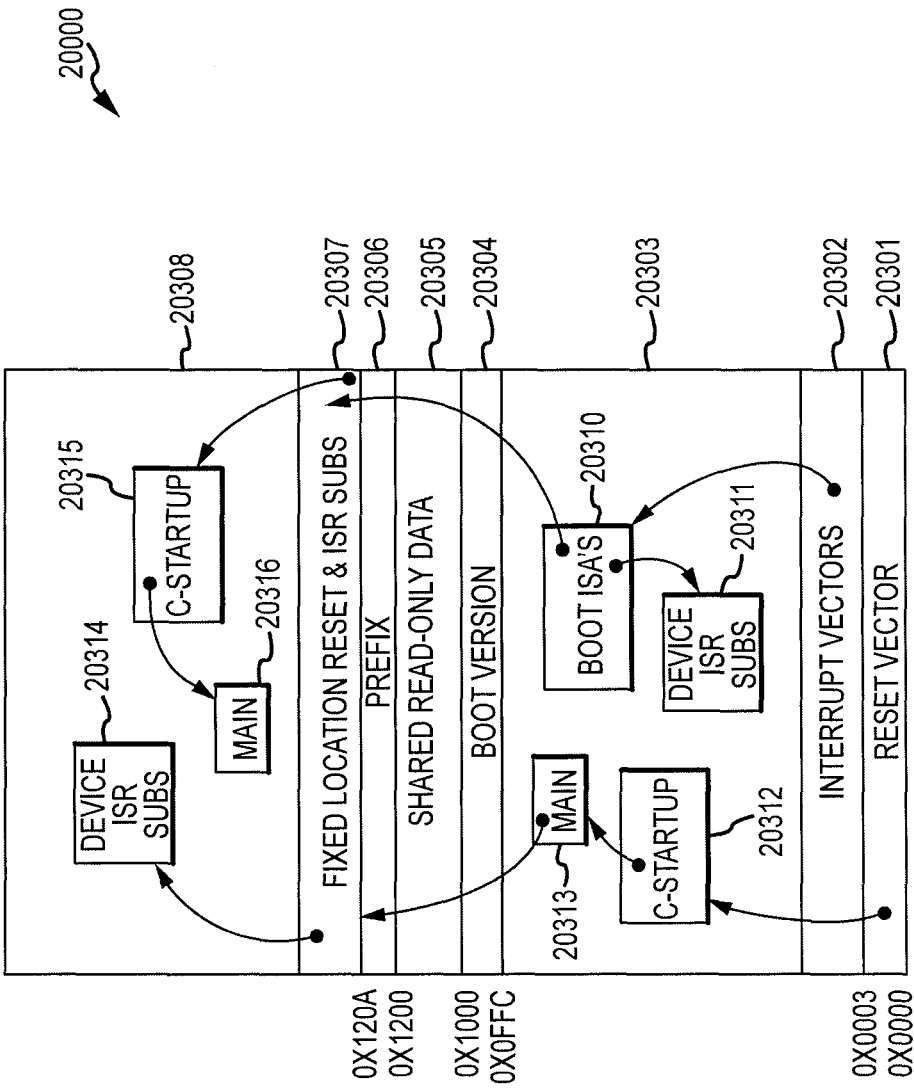
FIG. 20 is an illustration of combined boot and application code image of a single set of interrupt vectors.

FIG. 20 shows the combined boot and application image 20000, which will be described in more detail in the usage discussion below. For testing purposes, both the boot or application code may be complete standalone C programs, and can be tested individually. The full application image as generated by the linker consists of blocks 19201 through 19208, with a gap between blocks 19202 and 19203 as already described. (The FOTA image as defined herein consists of just blocks 19206 through 19208, which will be discussed in more detail below.) If the full application image 19000 is downloaded into the microcontroller and executed by itself, the reset vector (block 19201) will jump to the C-startup routine in block 19210, which will initialize the stack pointer and global variables, and then call the main( ) function block 19211. Any interrupts will be handled via the interrupt vectors in block 19202 starting at an exemplary address such as 0x0003, which will call the temporary ISRs in block 19203, which in turn will call the fixed location ISR subroutines in block 19207. These in turn will call the actual device ISR subroutines in block 19209 which may located at any convenient location in the application image. The dummy boot version shown at address 0xFFC (block 19204) and the shared data at exemplary address 0x1000 (block 19205) will be available to the application program.

The main routine in the application program, noting that prefix area (block 19206) is all zeroes, will be able to determine that it is running in standalone mode, and will write a copy of its image starting at exemplary address 0x1200 (start of block 19206) to a predetermined memory area to store a FOTA image, such as to a nonvolatile memory device such as an SD card. As it is writing out this image to the nonvolatile memory (or SD card, for example), the application code will initialize a predetermined number of initial bytes representing the prefix area and the reset vector, and in the preferred embodiment there are 13 such bytes. In the preferred embodiment, the first 13 bytes are initialized with the following data: Byte 0-0 (could be used for high 8 bits of code length if >16 MB); Byte 1-0 (could be used for low 8 bits of high word of code length if >64K); Byte 2—high 8 bits of low word of code length; Byte 3 -low 8 bits of code length; Byte 4—firmware version—major digit; Byte 5—firmware version—minor digit; Byte 6—firmware version—revision digit; Byte 7—firmware version—build digit; Byte 8—high 8 bits of address of prefix area (e.g. 0x12); Byte 9 -low 8 bits of address of prefix area (e.g. 0x00); Byte 10—copy of boot vector at address 0; Byte 11—copy of boot vector at address 1; Byte 12—copy of boot vector at address 2.

The code length in bytes 2 and 3 is calculated using a special symbol representing the end of the program. Bytes 0 and 1 are assumed 0 for the 8051 since its address space is 64K. The boot code is assumed to be less than 64K in length so a 16-bit address for the beginning address of the prefix area (Bytes 8 and 9) is adequate in the preferred embodiment. This value is used when the image is read from the SD card, to determine where to begin writing the image.

Note that bytes 10-12 will overlay the three bytes of the fixed reset subroutine at address 0x120A. These three bytes (copied from program addresses 0 through 2) will contain the address of the application's C-startup routine. Thus a call to the subroutine at address 0x102A will call the application's C-startup routine even after the reset vector has been overwritten by the boot code.

All bytes after the first 13 will be copied from the current program flash memory starting at 0x120D (in this example) and running to the end of the program. Two final bytes will be added representing the 16-bit cyclical redundancy check (CRC) calculated over all of the previous bytes. This application image written out to the SD card is the same format as any images downloaded over the air using FOTA. In addition to being used for testing, this copying of the image out to the SD card is the normal method to create a new "master" SD card or other nonvolatile memory after the code is updated. The master SD card or other removable nonvolatile memory can then be duplicated in a copier, and each copy installed in devices during the manufacturing process, without having to program each one (only the boot image, which is much shorter, has to be flashed).

The SD card (or other removable nonvolatile memory) is set up to have multiple slots for images of the storing application code (in the case of the 8051, each of these are 64K long). Slot 1 is always the factory-programmed default image. Slots 2 and 3 in this example are used in a ping-pong basis to hold the latest and the next to last copies of the application code downloaded over the air. Two sets of variables defined in a global memory block on the SD card or removable nonvolatile memory keep track of which slot is the latest. If a problem occurs with a downloaded image, this information is used to revert back to the next most recent copy of the code. The scheme could of course be extended to hold more images than just the three (factory, latest, and next to last).

If the boot image 18000 is downloaded into the microcontroller and executed by itself, the reset vector will jump to the C-startup routine in block 18112, which will initialize the stack pointer and global variables, and then call the main( ) function block 18113. Any interrupts will be handled via the interrupt vectors starting at address 0x0000 which will call the boot ISRs in block 18110. Any boot ISR for an interrupt which is used by both the boot and application code has an "if" statement which steers it to either the boot or application ISR subs depending on which one is active.

Since the boot code is running in this case, the ISRs will call the device ISR subroutines in block 18111. The boot version at address 0xFFC (block 18104) and the shared data at address 0x1000 (block 18105) will be available to the boot program. When the main( ) routine in the boot code (block 18113) runs, determining that prefix area (block 18106) is all zeroes, it will assume it has just been programmed into the microcontroller. It will set a variable app_code_running to 0, and will download the application program from slot 1 of the SD card (or other removable nonvolatile memory) FOTA image area. It will start flashing the program starting at the address given in Bytes 8 and 9 of the prefix area located in the first block read from the SD card—0x1200 in this example.

The variable app_code_running is shared between the application and boot code, by placing it at a fixed location known to both (e.g. at the end of RAM). It is also not initialized by either the boot or application C-startup code.

Once the entire application program is read from the SD card and flashed into the microcontroller's memory, the memory image will look like FIG. 20 (combined boot and application image 20000).

As the image is downloaded, a CRC (cyclic redundancy check value) is calculated. This is then compared with another CRC stored at the end of the image 20000, and if they match, the boot code then calls the reset subroutine at fixed address 0x120A (in this example) in block 20307. Since the application code has now been overlaid on top of the boot image starting at address 0x1200, the reset subroutine will point to the C-startup routine for the application code (20315), which will reset the stack pointer and global variables for the application, and call the main( ) routine block 20316. One of the first things the application main function does is to set the variable app_code_running to the value ENABLE_BOOT_VECTOR_SWITCH.

Now as interrupts come in to the interrupt vectors in block 20302, they will still call subroutines in the boot ISR block 20310, since the interrupt vectors were not rewritten when the application code was flashed. However now the app_code_running variable will be set to ENABLE_BOOT_VECTOR_SWITCH, which will cause the boot ISR's routine IF statement to call the one of the fixed ISR subroutines in block 20307 instead of one of the boot device ISR subroutines in block 20311. Since each ISR subroutine in block 18107 of the boot code matches address for address those in block 19207 of the boot code, these calls go to the right place. The ISR subroutine in block 20307 will then call one of the application device ISR subroutines in block 20314. After the interrupt is serviced, the program will resume somewhere in the application code block 20308 depending on the particular application code.

If a hardware reset occurs, the boot code will get control since the reset vector at address 0 still points to the boot C-startup routine block 20312. After initializing the stack pointer and boot global variables, it will call the main( ) routine block 20313. Seeing that this was a hardware reset, the boot code will perform a CRC check of the entire application image starting at address 0x1200 (in this example) and going to the end of the program (determined by the length in the first four bytes in the prefix area at address 0x1200). It will compare the calculated CRC with the one at the end of the program image 20000. If the calculated and stored CRCs match, the boot code will jump to application code by calling the reset subroutine in the fixed reset and ISR area block 20307, which in turn will call the C-startup routine for the application block 20315, which in turns calls the main( ) function block 20316 of the application. If the computed and stored CRCs do not match, the boot code will reset the running_app_code variable to force re-flashing of the application program. If a software reset (SWR) occurs, this may result from one of four cases: (1) the application code was "asleep", and it has now woken up which generates an SWR; (2) the application was in an Administration menu, and the user has selected RESET; (3) a new firmware image has just been downloaded over the air (FOTA); or (4) the user has elected to revert to the original factory image of the firmware. There may be other implementations that may include other case types.

What action to take is determined by a shared RAM variable called download_num_pos (and a redundant shared variable called download_num_min which contains the 2's complement of download_num_pos). If download_num_pos is zero and the running_app_code variable is set to ENABLE_BOOT_VECTOR_SWITCH, then either case 1 or 2 above is assumed, and the application code is given control by calling the reset subroutine at fixed address 0x120A which in turn will jump to the C-startup routine for the application.

If download_num_pos is greater than zero, and the value matches 0-download_num_min, then either case 3 or 4 above is assumed, and the microcontroller will download the application program from slot given by download_num_pos in the SD card FOTA image area. In case 3, download_num_pos will be set representing the slot that the downloaded FOTA image was just written to. In case 4, download_num_pos will be 1 indicating the original factory image should be read and re-flashed.

If a watchdog timer (WDT) reset occurs, and the application code has been running a predetermined time period such as at least eight minutes (determined by the shared variable LongSeconds greater than some time period such as MINOPERATINGTIME), and the running_app_code variable is set to ENABLE_BOOT_VECTOR_SWITCH, then the application code is given control by calling the reset subroutine at fixed address 0x120A which in turn will jump to the C-startup routine for the application. In alternative embodiments, the jump to a startup routine occurs after any appropriate condition occurs, such as through measurement of a time period elapsing by any technique available to the preferred embodiments. Since the microcontroller's reset status has not been zeroed yet, the application code will know the reset was a result of a WDT reset and will handle it.

However if a WDT reset occurs and the application code has been running less than eight minutes, then it is assumed there is something wrong with the new image, and an attempt is made to revert to a previous one. The globals block of the SD card is read, which contains (among many other things) the most recent values of download_num_pos and download_num_min, and the previous values of the same variables. If the positive values match the 2's complement values of the negative variables, then the application code is reverted to the previous version by using setting download_num_pos equal to prev_download_num_pos, and preceding as before to use download_num_pos to re-flash the image off of the SD card. When a previous version is loaded, the variables in the SD globals block are updated, such that another WDT will cause the next older version to be flashed, all the way back to version 1 (which is the initial factory-programmed version).

Multiple Set of Interrupt Vectors

Figure 21:
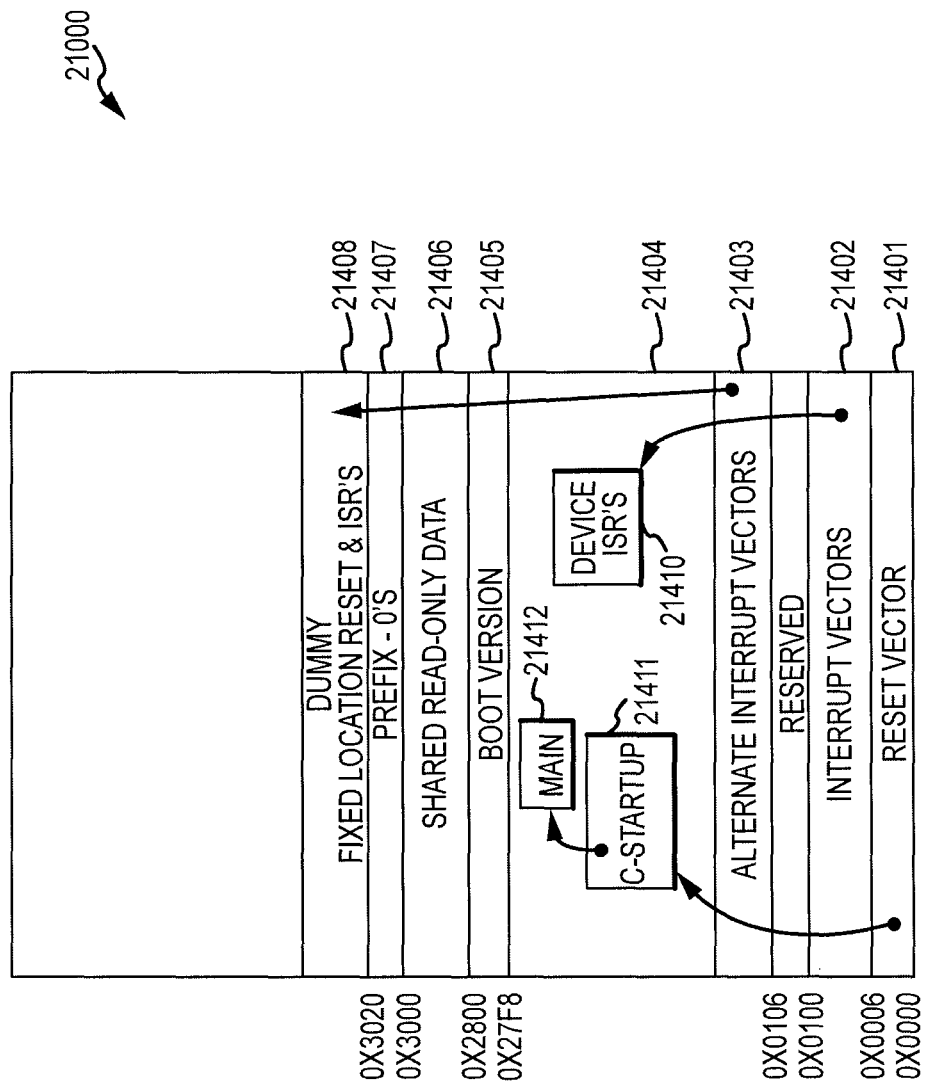
FIG. 21 is an illustration of a boot image of two sets of interrupt vectors.
Figure 22:
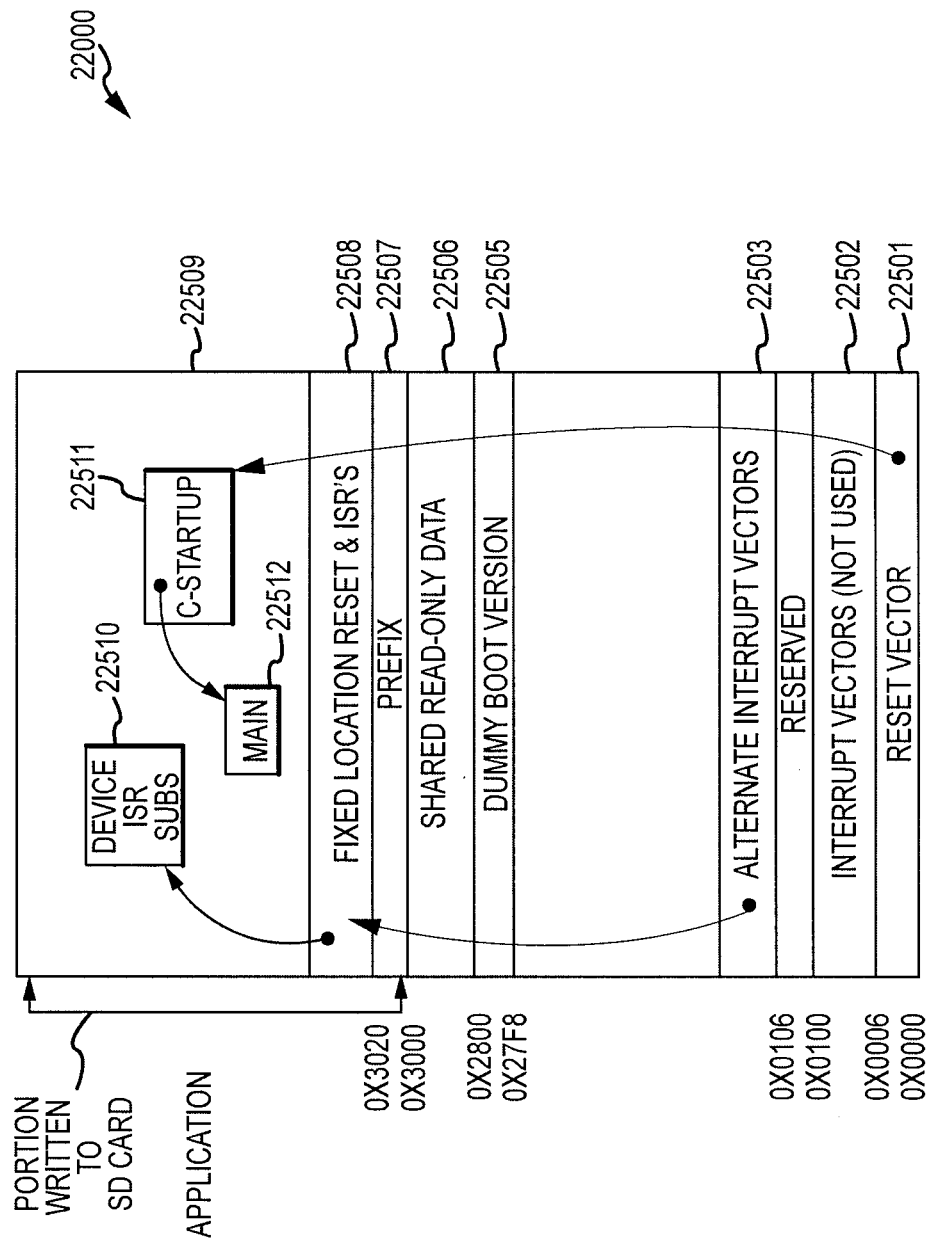
FIG. 22 is an application image of a two sets of interrupt vectors.
Figure 23:
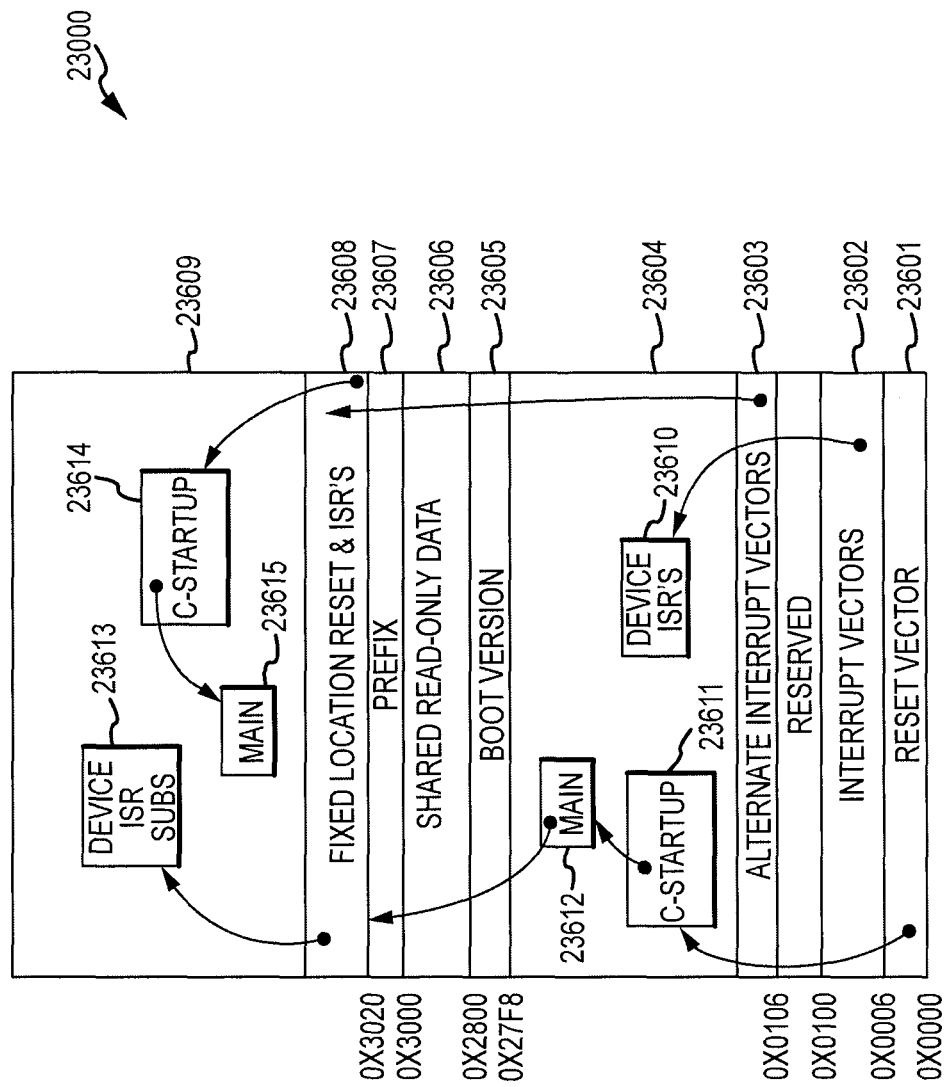
FIG. 23 is an illustration of combined boot and application code image of two sets of interrupt vectors.

Some embodiments of the present invention utilize microcontrollers that support more than one set of interrupt vectors, and the methods and systems described above in accordance with a single set of interrupt vectors is somewhat simplified as shown in FIGS. 21 through 23. In FIG. 21, which shows the standalone boot program image 21000, the primary set of interrupt vectors (block 21402) is used for the boot code. Therefore the vectors can jump directly to the device interrupt service routines (ISRs) (block 21410) without any code to switch between the boot and application ISR handlers. The reset vector (block 21401) still always points to the C-startup routine 21411 for the boot code. The alternate set of interrupt vectors (block 21403) jump to a set of ISR routines located at fixed locations in the application program space (block 21408), but in the boot image these are just used for linking purposes and are not actually active. Each consists of a subroutine call to a stub.

FIG. 22 shows the standalone application program image 22000. The regular set of interrupt vectors are not used. The alternate set of interrupt vectors jump to a set of ISR routines located at fixed locations (block 22508) which overlay the same addresses as the in the boot image 21408. Each consists of a subroutine call to handler in the device ISR subroutines block 22510. So that the application program can be run standalone, the reset vector points to the C-startup routine block 22511 (this is done by the linker by default), which calls the main function block 22512 after initializing the stack pointer and application global variables. The main routine sets a hardware bit so the alternate interrupt vectors (block 22503) will be used.

FIG. 23 shows the combined boot and application image 23000 as it is normally resides in the device. As before, the boot code will always get control on any hardware or software reset, with the reset vector block 23601 jumping to the boot C-startup routines block 23611, which in turn calls the main( ) function block 23612. The regular set of interrupt vectors block 23602 will be active by default, jumping to handlers in the boot device ISRs block 23604. When the main function block 23612 jumps to the application program, it disables all interrupts and then calls a subroutine at the beginning of block 23608 which in turn calls the application C-startup routine. After initializing the application stack pointer and global variables, the application C-startup routine calls the application main( ) function in block 23615 which immediately sets a hardware bit so the alternate interrupt vectors (block 23603) are now active, and then it enables interrupts once again. All interrupts will jump to the fixed location ISRs in block 23608 which will call the actual handlers in the application device ISR subs block 23613.

Exemplary FOTA Process

Figure 24:
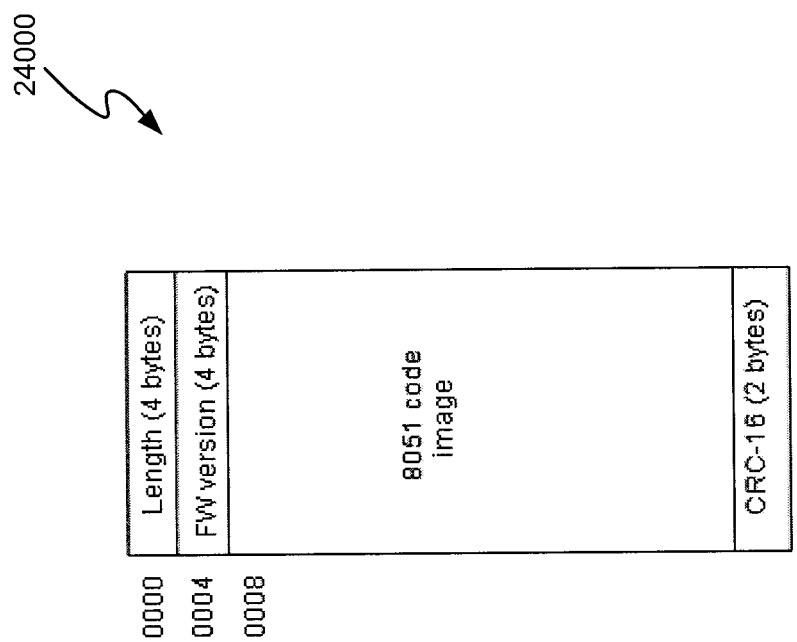
FIG. 24 is an illustration of a downloaded SD card application program image.

While various embodiments may provide for firmware updates in accordance with implementations of the present invention, one preferred embodiment is provided as follows, and describes an embodiment without limitation. A file to be loaded comprises an image 24000 of the application code space, with a 32-bit length indicator and four-byte firmware version at the beginning and a 16-bit CRC at the end as shown in FIG. 24. These eight bytes are in fact are the same as the first eight bytes of the prefix area described earlier. The firmware version consists of four bytes ranging from 0-99 representing major, minor, revision, and build number, e.g. 1.0.6.18. In a preferred embodiment, both the length and firmware version are stored in big-endian order, high-order byte first. The 16-bit CRC at the end of the file is part of the file data, and is not calculated or added by the server.

The binary image is created by a program running on a computer (or "PC," which for the purposes of the present invention may represent a personal computer or other general purpose computer), following the link step, which takes the output of the linker and strips off all of the program code prior to the prefix area (the offset of the prefix area, e.g. 0x1200, is given as a command line parameter to the PC program). The values for the 10 bytes of the prefix area are calculated by the PC program using the same method as the routine running on the device itself that writes out the image to slot 1 of the SD card. The first three bytes of the program are then copied to bytes 10-12 to generate the fixed location reset vector to be called from the boot program. Note that the full output of the linker is still kept active for downloading to the device for standalone testing as pictured in FIGS. 19 and 22. To accommodate limited buffer space available commonly used in the devices to be updated, the file may not be sent all at once but in segments. In a preferred embodiment, the file is downloaded in 1024-byte segments, each with its own stored length and CRC. The segments will be requested using the protocol shown in FIGS. 25A and 25B.

An "Enfora ID" field shown in FIG. 25B is a serial number is used to look up a database record for the remote device in the server's database as described below. The Number of Readings field is actually used as a flag to specify that either a file segment should be downloaded (Number of Readings=1), or that all segments have been downloaded and the server can disconnect (Number of Readings=0). This is needed because unlike other protocols in use by the device, the server does not automatically disconnect after sending a segment of the file—even the last one. Other protocols may also use aspects of the present method, and may not be limited to a FOTA process. This is to allow the remote device to check the received data using the calculated CRC for that segment, and request a retransmission if necessary. So when the remote device has received the last segment successfully, it will send one final request with Number of Readings=0 to indicate it is done.

The requested length for each segment is expected to be the predetermined length such as the exemplary embodiment of 1024 bytes, except for the last segment which will be for the number of bytes left. The remote device will know how many bytes are in the file after downloading the first segment which contains the length and firmware version fields.

In various embodiments, it is possible to have multiple versions of firmware for the same hardware (e.g. because a customer wants to freeze a specific implementation in the field, or a customer requires a special build because of custom features). The latest authorized version number for each device is maintained in a table referenced by the device's serial number.

In a preferred embodiment the remote device is programmed to check for a firmware update periodically, such as every night, by making a request to the server using the protocol just described. When the server receives the request for the first segment (offset 0 of the file) from the remote device, it compares the four-byte Firmware Version in the request with the four-byte Firmware Version in the database for that device. If they are equal or if the firmware in the device is greater it sends a response code to the remote device, indicating it is already up-to-date (for example, the response code could be designated as "U" to indicate that the device already up-to-date). If the firmware on the device is out of date, the server sends a response code indicating that an update is to be transmitted (such as a value of "0") followed by the binary data. Other response codes may be used for error conditions. In the case of an update (e.g., "0")

response, the entire packet looks like the image shown in FIG. 26 where the response code is the first byte, followed by the length and offset (same as provided in the request packet), followed by the binary data. The binary data is obtained by doing a seek into the binary image file 26000 based on the "offset", and reading for "length" number of bytes. The CRC is calculated by the server over the first "length"+7 bytes or the entire size if other methods are used. The last segment sent will have two CRCs—one which is already part of the binary file being downloaded, and the second one calculated just over this segment. The server is only responsible for the second one.

Additional Boot Code "Interim" Implementation

As discussed above in regards to various embodiments of the present invention new application code may be updated via a FOTA operation. Normally, the boot code is expected to remain stable. However, under certain circumstances it may be found that the boot code requires updating as well. This is also possible by using a similar FOTA method as discussed above, with the execution of a special interim application firmware as the firmware code previously described as being sent to the device. For purposes of the present invention, this application code is referred to as "interim" since it resides in the device long enough to perform its required function (e.g., flash the new boot code and possibly perform other "housekeeping" functions), then the routine exits such that only certain predetermined code sections such as the new boot code and the previous or even a new version of the application code remain resident in the device. In one embodiment, when its execution is successfully completed, the interim code is completely removed and not saved in storage such as the SD card.

In an implementation of the present invention, a server (or method that sends any new application via FOTA to the device) is configured to transmit the special interim code to the device. The interim code also includes an image of the new boot code. The image of the new boot code may be concatenated to the end of the interim code, but placed at a known address so the interim code can then copy (e.g., "flash") the image of the boot code to the proper storage area when the time is indicated. The interim code, in many embodiments, is expected to occupy less storage space (e.g., smaller byte-size) than the actual application code. Therefore in certain embodiments, it may reside along with the boot-code in the area typically used for the application-code.

The interim code is tranmsitted to the device via FOTA methods as described previously. Once flashed to the device as the application code (by the "old" boot code) the interim code sets out all steps required to load the new boot code. In some hardware implementations the device may become nonfunctional if the boot-code is stored or flashed improperly, or is otherwise corrupted (e.g., since all interrupt vectors and initial start-up is always executed via the boot code). Therefore it is important to provide for methods to verify correct software configuration before attempting to re-flash the boot code. For example, in various implementations, an additional CRC check can be provided for in the boot-code image. The interim code can read through the entire boot-code image, then check to ensure that the supplied CRC is consistent with the saved image. If not, the interim code will request a new FOTA and start over again. Other internal functions and conditions can also be checked for proper operation before proceeding with flashing of the new boot code.

When ready for execution, the interim code copies the image of the new boot code (currently saved in the application code area), and flashes or stores the new boot code image to the boot-code area. During this operation, all interrupts must be disabled to ensure the device does not attempt to access the interrupt vectors until the new boot-code is installed. When completed, a CRC may also be performed over the new "flashed" image, and the re-stored or re-flashed if an error is detected from a CRC mismatch.

The interim code is now ready to allow the new boot-code to re-flash the previous application code saved on the SD-card. The interim code does this by initializing so that the next software reset causes the boot-code to flash the application code, but with the application code "image number" set to that of the previous code saved on the SD card. In various embodiments, the interim code may be configured to download (e.g., via FOTA techniques) a new version of the application code if that is also desired to be updated. In this case, it will have already performed the FOTA download and saved the new application code to the next image location on the storage device or SD card. The interim code may also save the image to the first location so that the image is considered the "factory" programmed version. In any case, the interim code exits in such a manner to cause the boot-code to either re-flash the previous application code image, or to flash the "new" application code. In a preferred embodiment, the interim code after proper execution removes references to itself on the storage device (e.g., the SD card). The device is now configured in a normal operational state, but with the new boot code installed and executing using either the previous or new version of the application code.

System for Remote Device Configuration, Tracking, and Provisioning

The initial product release of any electronic device may offer limited functionality as defined by its initial hardware/software configuration, customization, or other factors that may require adjustment to achieve desired performance. For example an electronic device such as a health data communicator that is configured to interface with medical instruments or devices may include support for a limited set of medical devices when initially made available for purchase. Further, as new medical devices become available to the public, the health data communicator may require reconfiguration to be able to properly interface to the new medical devices. Additionally, it may be impractical for a health data communicator to include sufficient configuration information to support every medical device that may be made available in the marketplace, so customization of a particular medical data communicator to a particular patient allows the patient's medical data communicator to include the necessary information to support that patient's needs without requiring the storage of ungainly amounts of interface information.

There is provided a firmware system architecture that allows medical data communicators to be configured to meet any particular purpose. Embodiments of the present system enables update and interoperation between a medical data communicator and a docking station through a defined, device independent, interface. In various embodiments, this architecture provides for (a) common system functionality separated from device specific implementations; (b) hardware specific implementation of the medical data communicator and its docking station is encapsulated in common host firmware, while individual driver firmware components mayl handle any device specific functionality; (c) a drivers do not need to communicate with any hardware components directly while the host is uninvolved in the processing of any device specific data; (d) the host communicates with drivers through a common defined interface, allowing the host to load and interact with drivers without dependency on any particular driver or device implementation; (e) host firmware is device and modality agnostic, for example, the host firmware may provide generic services to drivers but may not contain any device or modality specific code; (f) Individual drivers may be loaded dynamically on an as-needed basis as the host firmware is able to detect and identify a device when it is plugged in and load the correct drivers for it dynamically; (g) when a device is disconnected, the host is able to remove the driver when the resources need to be reclaimed; and (h) all firmware components may be developed in a language independent manner, as a language resource module is maintained by the host and updated with additional downloadable resources when needed to support any particular language configuration without hard-coded voice or visual output.

Figure 27:
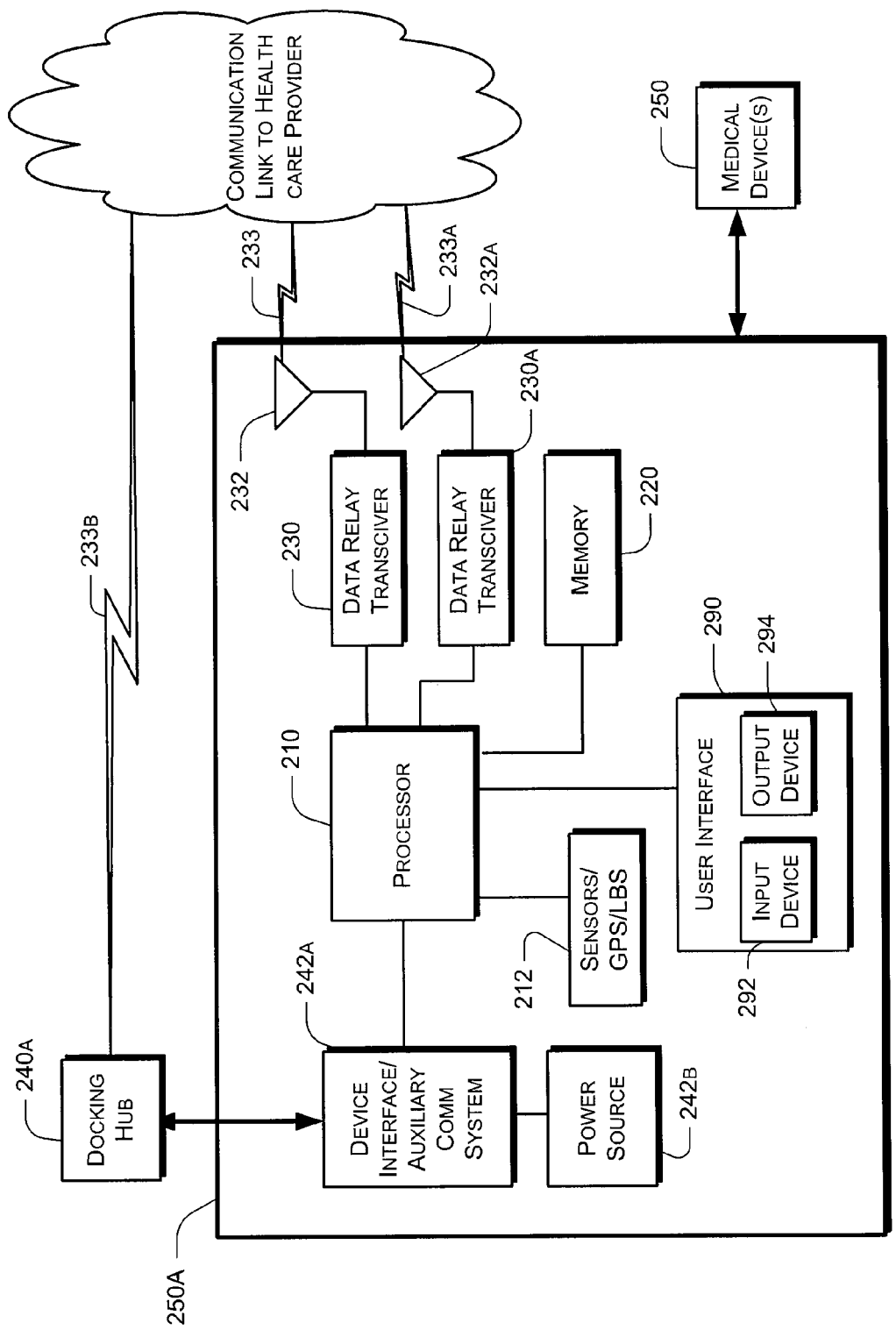
FIG. 27 shows a block diagram of a medical data communicator of the present invention in the context of an illustrative embodiment of the system of the present invention.
Figure 28:
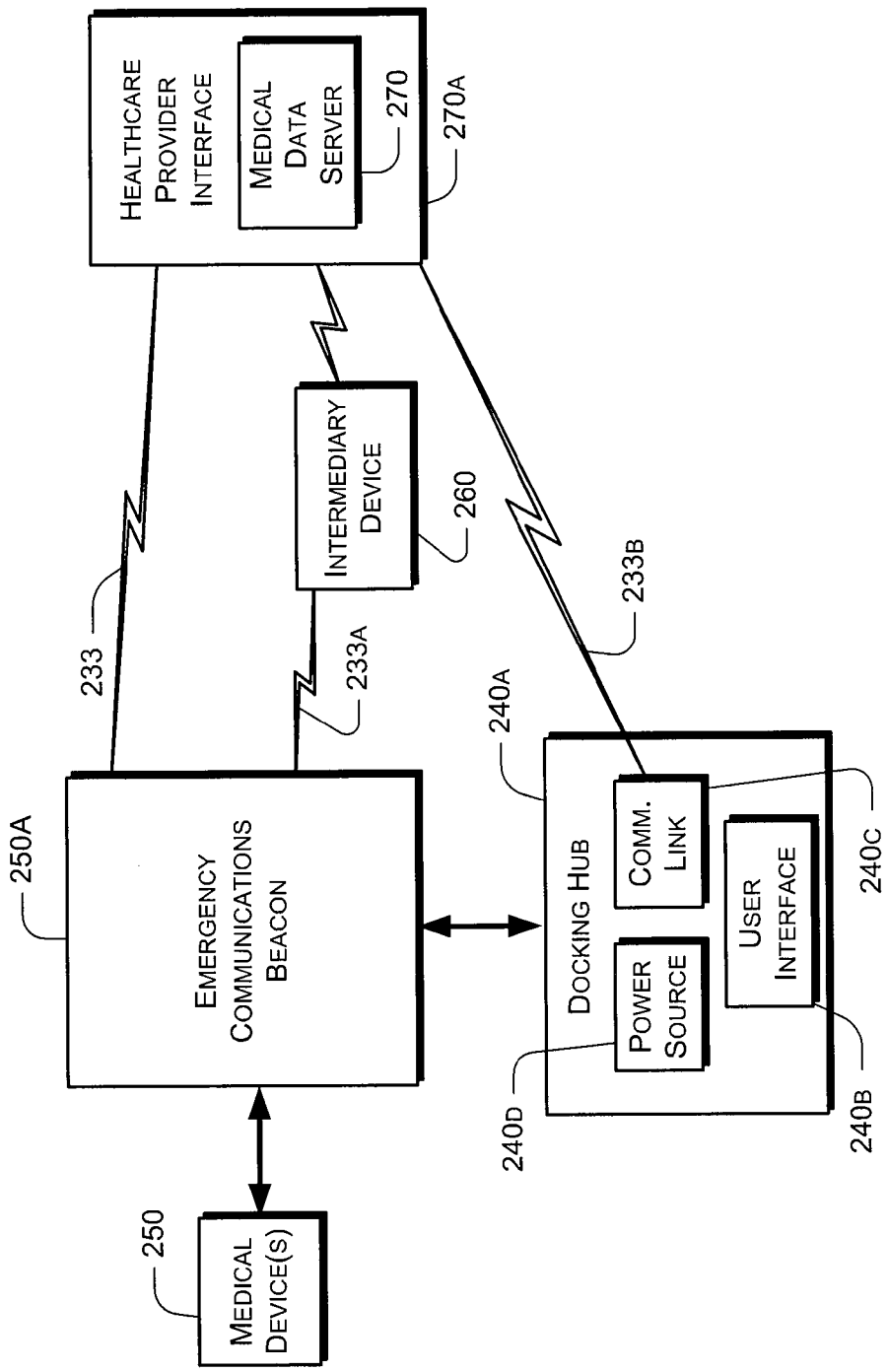
FIG. 28 shows a block diagram of a medical data communicator of the present invention configured as an emergency communications beacon in the context of an illustrative embodiment of the system of the present invention.

Referring to the block diagrams shown in FIGS. 27-28, there is provided a medical data communicator 250A that includes a processor 210, a device auxiliary interface and communication system 242A, a power source 242B, sensors such as GPS or LBS location-based sensors 212, a user interface 290 with at least an input device 292 and an output device 294, memory 220 coupled to the processor 210, and data relay transceivers 230, 230A, that manage communications to a heath care provider. One or more medical devices 250 may be interfaced to the medical data communicator 250A, where medical data may be obtained by the medical data communication device, and may be relayed to any appropriate location such as a health care provider or monitoring service. An alternative communications path 233B is provided through the medical communicator device connection to a docking hub 240A. The medical data communicator 250A may comprise any device capable of receiving, tracking and communicating data from health care devices, and may be configured to receive information from a medical data server 270. In one embodiment, the medical data communicator may comprise an emergency communications beacon allowing a patient to establish two-way communications with a healthcare provider or monitoring service.

Figure 29:
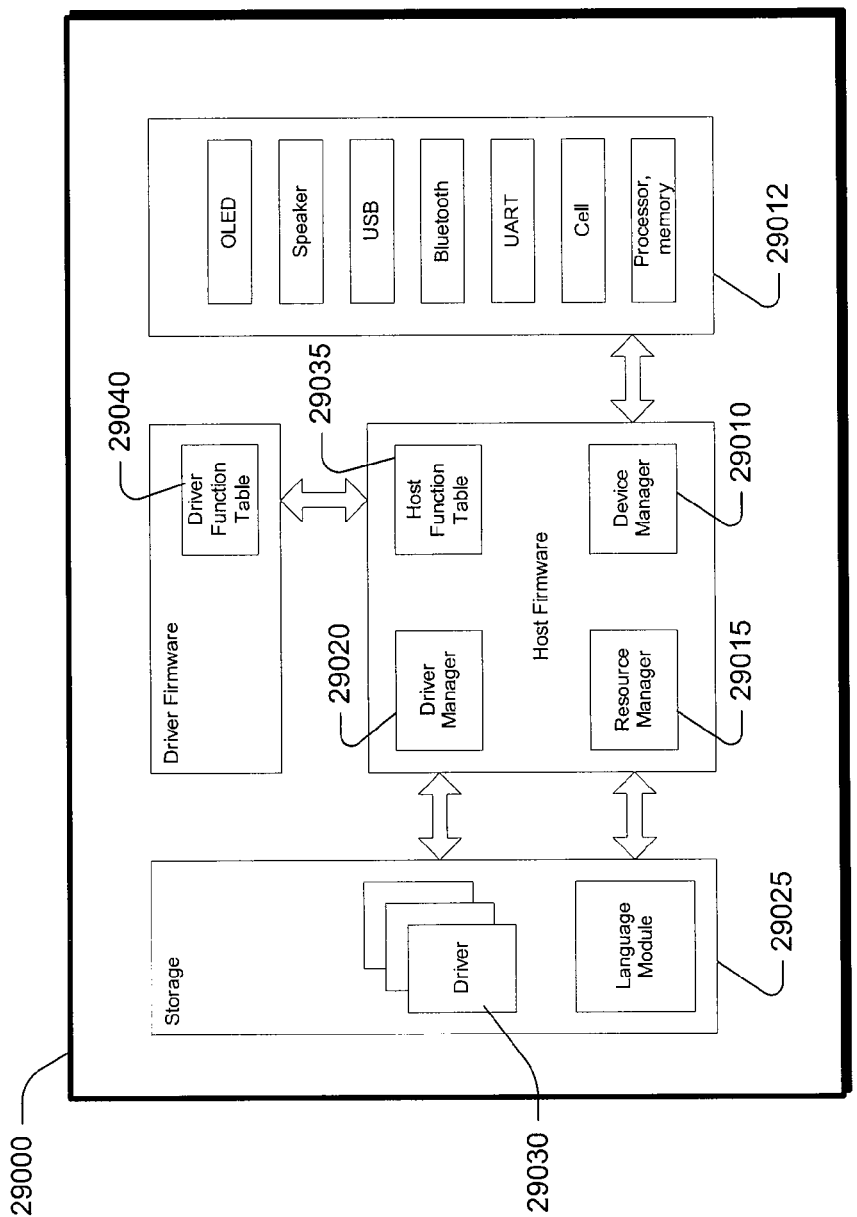
FIG. 29 illustrates a block diagram of an exemplary architecture of the present invention.

A block diagram depicting an architecture 29000 embodiment of the present invention is shown in FIG. 29. The illustrated architecture 29000 may be implemented within the medical data communicator 250A, docking hub 240A, a combination thereof, or any other component of embodiments of the present invention, where in various embodiments, the device 29102 may correspond to any external device such as medical devices 250.

The device manager component 29010 detects and identifies external devices 29012 and provides functions that allow drivers to communicate with them. The device manager 29010 detects when a device connects or disconnects through any of the integrated hardware modules. When connecting, the device manager 29010 will attempt to produce an ID that uniquely identifies the connected device based on the vendor and product model. For Bluetooth and USB devices, Vendor and Product IDs are part of the interface standard. For serial-based products such of those interfacing via a UART component, the present invention may create a custom identification tag or utilize other appropriate means to track identification. Alternatively, smart cables that interface serial devices to the medical data communicator may provide a unique ID as part of the smart cable's integrated electronics. Additionally, sending probe commands and analyzing the response provided by the device provides another approach to obtaining identification information.

Once a device connection/disconnection event has been detected, the device manager 29010 will notify a driver manager 29020 and provide the identifier of the device involved. For connection events, the driver manager 29020 will scan the storage medium 29025 to locate a matching driver 29030 based on the identifier. When found, the manager 29020 will load the driver into memory and activate it. If not found, the manager will contact a remote server and provide the device identifier to request a driver download. When downloaded successfully, the new driver will be added to the drivers 29030 on the storage medium 29025, loaded into memory and activated. When a device is disconnected, the driver manager 29020 may remove the driver from memory if and when resources need to be reclaimed and reused for other purposes. The driver manager may also contact remote servers periodically to check for available driver updates.

The resource manager 29015 maintains language and region dependent resources. It is notified by the driver manager 29020 whenever a new driver is loaded into memory to allow it to determine if this driver requires additional language resources not yet available on the storage medium 29025. If additional resources are needed, the manager will contact a remote server and download the missing items. Since most devices of the same device type need similar voice and text phrases, resources are grouped primarily by device type. The manager will ask the driver what type of device is connected and request the remote server to download the associated resources as one language set. If the driver requires additional resources specific to that driver, the manager will determine which resources are missing and download them individually when needed. The resource manager may contact the remote server periodically to check for available resource updates.

In various embodiments, a driver typically does not allocate resources or interacts with hardware components directly. The host provides the driver with a host function table 29035 instead. This table contains a list of pointers to functions that the driver can use to handle memory allocation, to communicate with the actual device and to interact with the user through output text and voice messages and receive key input.

Some functions may require the driver to provide a device parameter to indicate the target device. This parameter may be provided to the driver when the host has detected the device and requests the driver to open it by calling the Open function as specified in the driver function table.

In various embodiments, a driver is implemented as a separate binary object that can be downloaded, stored, loaded/unloaded and activated individually by the host firmware when needed. Drivers may implement the same interface, data structures and parameter constants, and an exemplary embodiment is shown in a C-compliant header file which is provided in appendix A-4. In various embodiments, driver binary objects start with a standard header structure that contains information such as the following: (a) the driver type; (b) version information indicating the major and minor version, the current revision and the build number of the driver; (c) maximum data size (in bytes) required by the driver, which may be used by the driver manager to reserve enough data space before the driver is activated; (d) list of device types supported by the driver, which may be used by the resource manager to ensure language sets are available on the storage medium for each device type; (e) list of supported device IDs, which may be used by the driver manager to select the proper driver based on the unique device identifier provided by the device manager when a device is connected; (f) list of driver specific language resources, which may be used by the resource manager to determine if all required language resources are present on the storage medium and to download additional items from remote servers if needed; (g) list of driver function offsets, which may be used by the driver manager to build the driver function table which is subsequently used by all host components to interact with the driver.

For the host firmware to interact with loadable drivers, each driver provides a predefined set of functions, shown as a Driver Function Table 29040 in FIG. 29. This function set is often standard in most driver architectures implemented in other systems, including Windows and Unix. These functions will be called by the host during the various stages of the driver's life cycle.

In preferred embodiments, both the host and driver firmware is implemented in a language and region independent manner. Instead of hardcoded text strings or audio files, the driver only needs to refer to user output by reference IDs. The resource manager in the host will access the language modules found on the storage medium to retrieve the corresponding text or voice data that is appropriate for the current language and region settings. Since proper feedback to the user is also an important function of the driver, the host provides a reasonable amount of functionality to allow the driver to format the screen, produce text output and generate a voice response, without the driver accessing any related hardware directly.

Figure 30:
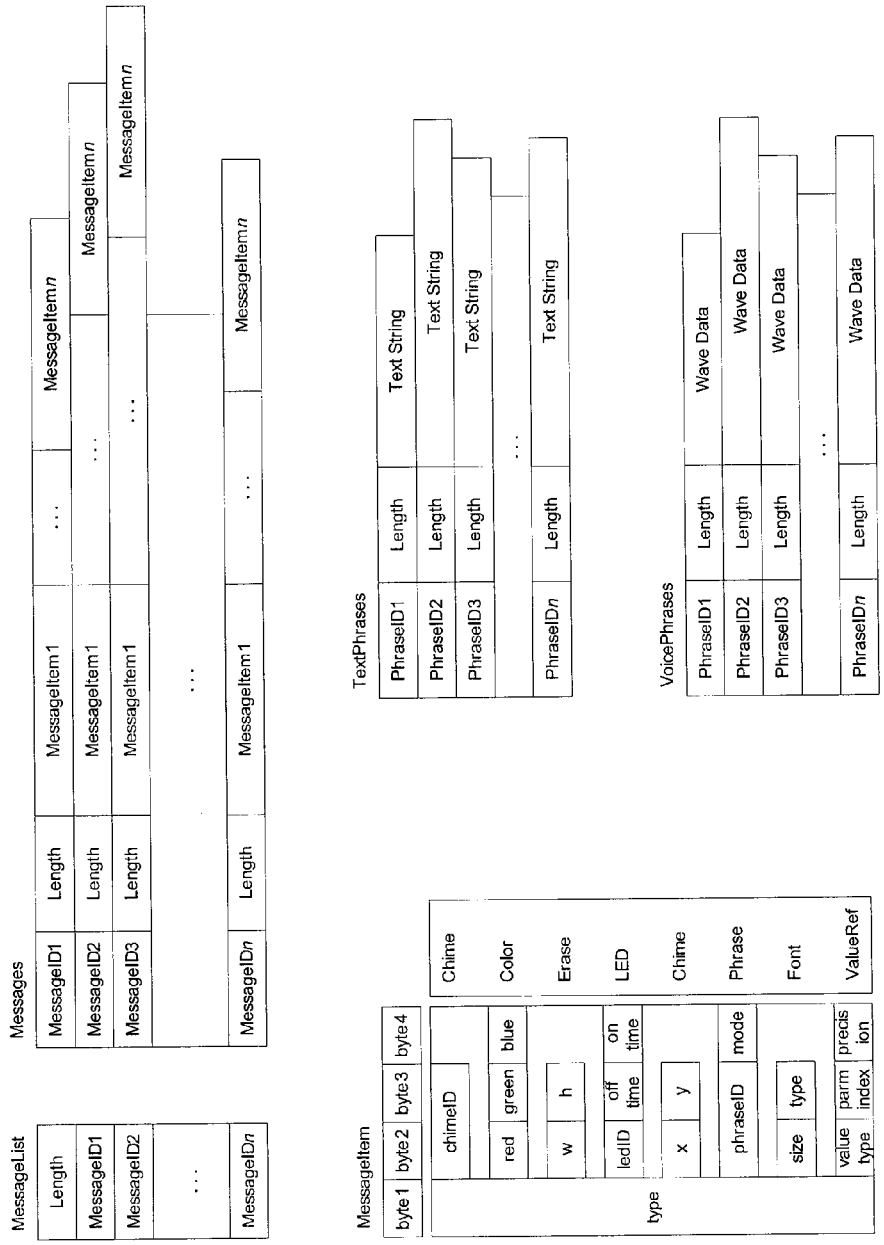
FIG. 30 illustrates a block diagram of an exemplary localization architecture of the present invention.

In one aspect of the present invention, a localization architecture is defined (an illustrative embodiment of which is shown in FIG. 30) that contains the following elements. Text or voice output is organized in Messages. Messages convey a particular self-contained piece of information to the user, like a blood pressure reading or a diagnostic status, but also basic items such as a status bar or menu options. A Message includes a sequence of one or more MessageItems. Each MessageItem includes one particular part of the message. A MessageItem may identify a particular text or voice phrase that should be output to the user, and may also contain instructions to clear the screen or define the text position. A MessageItem may also refer to a variable that contains some value that has been retrieved at runtime, like a blood glucose level, together with instructions that determine how the value should be interpreted and presented to the user. When all MessageItems are processed in sequence, the user should be presented with a complete visual and/or audible message.

The host maintains a list of messages on the storage medium where each message is identified by a unique messageID. The host also maintains a database of available text and/or voice phrases that are identified by a unique PhraseID. If a text phrase and voice phrase convey the same message but only use a different medium, both phrases should be identified by the same PhraseID.

Each driver header contains a MessageList that identifies all the messages that are specific to that driver. After a new driver is downloaded, the resource manager in the host firmware will retrieve this list and compare it with the list of messages already present on the storage medium, and request a download from the remote server for each individual message that is missing. The MessageList in the driver header may exclude messages that are considered standard for a particular device type. Since most devices with the same device type will typically need to convey the same type of information to the user, predefined MessageLists are already assembled by device type and are available on the remote server as one downloadable list. The resource manager can determine if resources for additional device types should be downloaded by comparing the list of supported devices in the driver header with the list of device types already present on the storage medium.

A Message contains MessageItems which may refer to a voice and/or text phrase but a message never contains the actual phrase itself. After a message has been downloaded, the resource manager will scan all MessageItems used in the message to identify any PhraseIDs that refer to phrases that are not found in the text or voice database on the storage medium and request a download from the remote server.

As noted above, a MessageItem may represent a wide array of instructions that both the host and driver can use to manipulate how a message is presented to the user. All message items consists of 4 bytes and are implemented in C as a union (see OutputModel.h header file in Appendix A-5).

Remote Server Monitoring (Listening)

An embodiment of a remote server used in accordance with embodiments of the present invention includes a monitoring, or "listening" function. Installed on an externally accessible server, the listening function monitors incoming traffic from remote devices such as medical data communicators, ensures the received data is properly processed, and sends a response back to the device if appropriate.

Various embodiments of the listening function provide for features that support the remote monitoring, configuration, and provisioning of medical data communicators, interfacing hubs, and other devices. In one embodiment, the listening function is fully configurable through a single XML file. This file specifies a broad range of configuration information, and includes, for example, packet layout definitions and routing of packets to proper handlers on local and remote servers. In this embodiment, every packet can be described entirely in XML. The routing of packets to the correct handlers can be precisely regulated by defining routing filters.

Routing filters include one or more filter expressions. The listening function may include a built-in compiler that supports an array of macros, arrays, field descriptors and all major mathematical operators. The contents of the XML file can be modified on-the-fly without the need to stop and restart the listening service before changes come into effect.

The listening functionality may be treated separate from actual packet processing logic. The listening function accepts raw binary data from a device, reformats the data into structures optimized for processing (such as by C# code), and then passes the structure to a separate handler module for actual processing. It provides the handler with both private and global stateful environments in case the handler needs to keep state. Once the handler completes processing, the listening function converts results returned by the handler back to the proper raw data format and submits it to the device. This functionality simplifies the development and integration of new handlers needed to introduce new features. Extended functionality is implemented by defining new packet types in the XML file and routing them to the new handler.

The listening function can route incoming packets to handlers installed locally on the same system, and fully supports .NET remoting to route packets to remote servers as well. This allows for a scalable design where processing tasks can be offloaded to other systems based on the incoming packet type. This feature is supports load balancing and to allows the integration of specialized servers that are highly optimized for one or more particular tasks. The listening function may also be fully multi-threaded, which allows processing of multiple incoming packets simultaneously without any predefined limits.

The listening function is highly optimized for maintainability. Most packet definitions, routing and packet handlers can be added, removed or modified while the listener is operational and without requiring the live listener to stop or restart. Maintenance required for one handler can be performed without affecting any other handlers installed in the system. The listening function may supports routing of packets to debuggers on remote development systems. This allows software programmers to develop new handlers and step through code without affecting operation of the listening function itself or the ability to process packets designated for other handlers.

Figure 31:
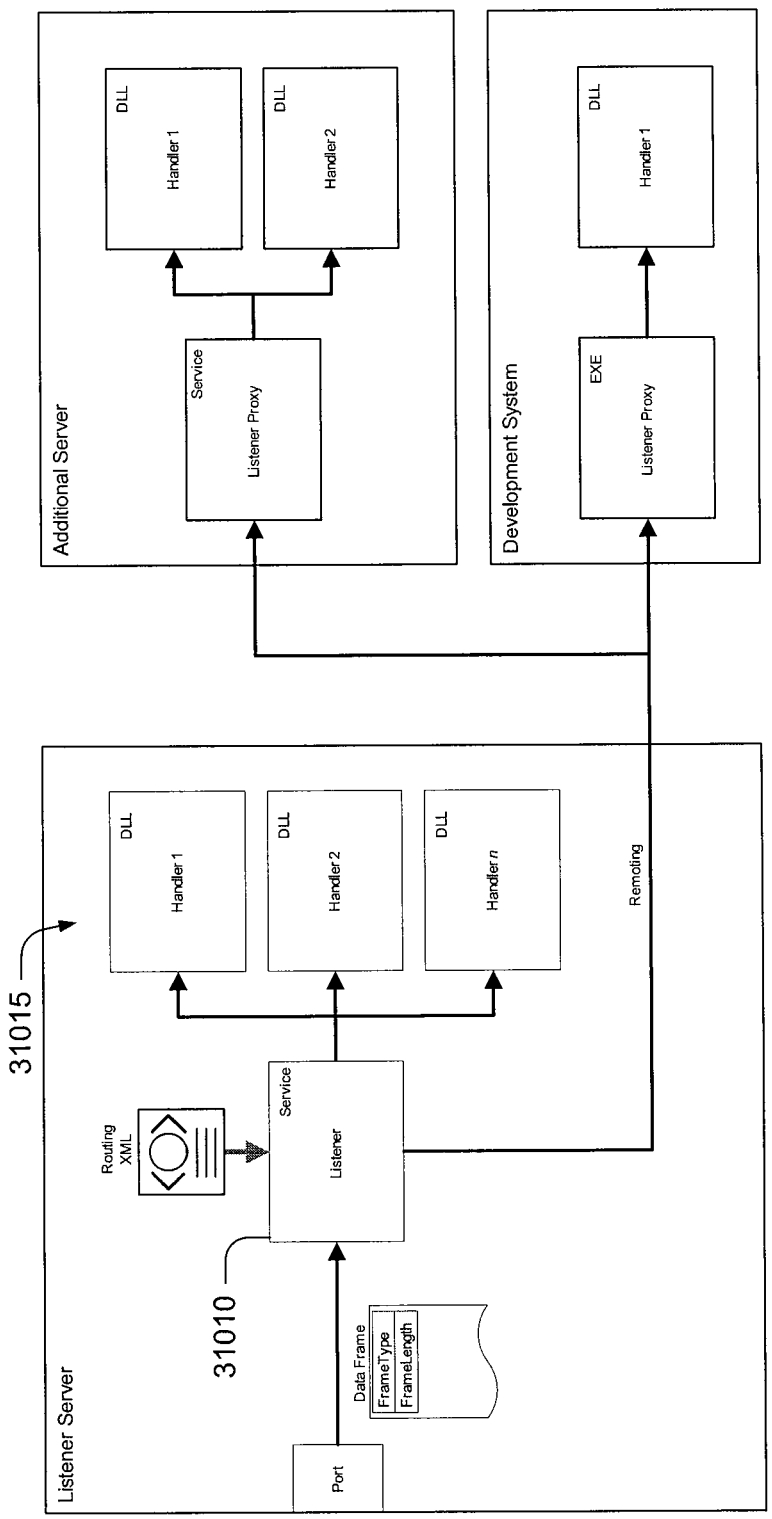
FIG. 31 depicts a block diagram of an exemplary listening function in a system of the present invention.

An embodiment of the listening function of the present invention is depicted in FIG. 31. As the figure shows, the listener 31010 is separated from the handler modules 31015 that perform the data processing. This allows the listener 31010 to focus only on socket communication, packet reformatting and routing to and from the proper packet handlers. The listener 31010 is able to perform this responsibility entirely based on packet descriptions and routing information defined in the routing XML file. This allows future implementations of yet unknown protocols and data handlers with minimal or no changes to the listener software.

In a preferred embodiment, the listener 31010 is implemented as a service running on a dedicated server. It monitors the port specified in the routing XML file for any incoming traffic received from an external devices such as medical data communicators. When a packet is received, the listener 31010 will match the content with all packet descriptions found in the XML file to select the correct packet type and convert the raw data into a type-safe high-level data structure that is optimized for processing by managed code (such as C# code). It will then apply the filters found in the routing section of the XML file to determine which handler should process the packet and locate this handler based on definitions found in the handler section. The listener 31010 will subsequently invoke the handler through a predefined and common handler API. For handlers that need to maintain state information between subsequent invocations or share state data with other handlers, the listener 31010 provides private and global stateful environments on both the session and application level. Once the handler completes its functions, the listener 31010 will convert result data from managed code back to a raw data response packet and send the packet through the port back to the remote device (such as a medical data communicator). In a preferred embodiment, communication between listener and handlers is performed asynchronously. This allows the listener to handle many incoming packet simultaneously, limited only by the resources available on the server and the multi-processing capabilities provided by the handlers.

The listener 31010 fully supports remoting to communicate with handlers installed on remote servers. A listener proxy is installed on the remote server to intermediate between the listener and the handler.

Packet routing is one of the prime responsibilities provided by the listening function. The listener 31010 monitors a specific port for incoming traffic received from an external device such as a medical data communicator. After converting this packet to a high level data structure, the listener will then determine which handler should receive the data for further processing, based on the packet content. Since it is anticipated that new or modified packet types will be introduced on a regular basis, together with new handlers to process them, described embodiments of the listener provide a highly flexible means to configure this routing process.

The listening function provides this functionality by supporting the use of routing filters. Routing filters are fully defined in the routing element of the configuration XML file. It consists of a collection of route child elements that each assign a certain condition to a packet handler. When the listener receives a new packet, it will evaluate all conditions in the order they appear in the XML file. This allows handlers to be prioritized as the listener will offer the packet to the first handler that produced a match. If that handler rejects the packet, filtering will continue until a matching handler is found that accepts the packet.

Conditions are specified by means of one or more filter expressions. The content of a packet is analyzed using the filter expressions which result in a Boolean value with true indicating a match. More complex filters can be produced by combining the results of multiple expressions through nesting. Filters expressions at a deeper nesting level form more restrictive (AND) conditions for the direct parent expression, while multiple expressions at the same nesting level produce widening (OR) conditions.

The particular implementations shown and described above are illustrative of the invention and its best mode and are not intended to otherwise limit the scope of the present invention in any way. Indeed, for the sake of brevity, conventional data storage, data transmission, and other functional aspects of the systems may not be described in detail. Methods illustrated in the various figures may include more, fewer, or other steps. Additionally, steps may be performed in any suitable order without departing from the scope of the invention. Furthermore, the connecting lines shown in the various figures are intended to represent exemplary functional relationships and/or physical couplings between the various elements. Many alternative or additional functional relationships or physical connections may be present in a practical system.

Changes and modifications may be made to the disclosed embodiments without departing from the scope of the present invention. These and other changes or modifications are intended to be included within the scope of the present invention, as expressed in the following claims.

What is claimed is:

1. A system comprising
a processor;
   a device interface;
   a nonvolatile storage medium coupled to the processor, the nonvolatile storage medium including a stored application image;
   a data relay transceiver; and
   a memory coupled to the processor, wherein:
     the memory includes at least a shared memory space, a boot portion, and an application portion;
     the boot portion includes code that when executed by the processor may modify the application portion, wherein:
       the boot portion includes a boot startup executable code, a boot main executable code, and a boot interrupt service routine code; and
       the application portion includes an initial application image comprising application startup executable code, an application main executable code, and an application interrupt service routine code; and the memory stores instructions that, when executed by the processor, cause the processor to:
- execute code within the boot main executable code to determine that the initial application image requires updating;
- retrieve the stored application image from the nonvolatile memory;
- overlay the application portion with the retrieved application image; and
- transfer execution control from the boot main executable code to the overlaid application startup code in the application portion wherein said transfer execution control further comprises overlaying a starting address for a boot reset routine to an address for the application startup executable code within the overlaid application image.

2. The system of claim 1, wherein retrieving the stored application image from the nonvolatile memory further comprises:
- computing a CRC code for the stored application image; and
- comparing the computed CRC code to a CRC code previously stored within the stored application image.

3. The system of claim 2, further comprising determining that the computed CRC code and the CRC code previously stored within the application image do not match, and thereupon:
- retrieving the stored application image from the nonvolatile memory; and
- re-overlaying the application portion with the retrieved application image.

4. The system of claim 2, further comprising determining that the computed CRC code and the CRC code previously stored within the application image do not match, and thereupon:
- retrieving a second application image stored within the nonvolatile memory; and
- overlaying the application portion with the second application image stored in the
- nonvolatile memory.

5. The system of claim 4, wherein the second application image corresponds to a previous version of the initial application image.

6. The system of claim 4, wherein the second application image corresponds to a first release version of the initial application image.

7. The system of claim 1, further comprising:
- detecting that a reset condition has occurred;
- determining that a device is running in standalone mode; and
- copying an application image stored in the application portion to the nonvolatile storage medium.

8. The system of claim 1, further comprising: setting an indicia to indicate that execution of interrupt service routines (ISRs) should be switched from an address within the boot interrupt service routine code within the boot portion to an address for the application interrupt service routine code within the application portion.

9. The system of claim 1, wherein executing code within the boot main executable code to determine that the initial application image requires updating further comprises:
- computing a CRC code for the initial application image;
- comparing the computed CRC code to a CRC code previously stored within the initial application image; and
- determining that the computed CRC code and the previously stored CRC code do not match.

10. The system of claim 1, wherein executing code within the boot main executable code to determine that the initial application image requires updating further comprises:
- obtaining a current version of the initial application image upon bootup;
- determining that the current version of initial application image is out of date.

11. The system of claim 1, wherein executing code within the boot main executable code to determine that the initial application image requires updating further comprises determining that a watchdog timer has expired.

12. The system of claim 1, wherein executing code within the boot main executable code to determine that the initial application image requires updating further comprises determining that a new version of the initial application image is available.

* * * * *